US007674831B2

(12) United States Patent
Atwal et al.

(10) Patent No.: US 7,674,831 B2
(45) Date of Patent: Mar. 9, 2010

(54) HETEROCYCLIC COMPOUNDS AS SWEETENER ENHANCERS

(75) Inventors: Karnail S. Atwal, Pennington, NJ (US); Anita B. Atwal, legal representative, Pennington, NJ (US); Robert W. Bryant, Princeton, NJ (US); Ivona Bakaj, Cranbury, NJ (US); Roy Kyle Palmer, Cranbury, NJ (US); Rok Cerne, Lawrenceville, NJ (US)

(73) Assignee: Redpoint Bio Corporation, Ewing, NJ (US)

( * ) Notice: Subject to any disclaimer, the term of this patent is extended or adjusted under 35 U.S.C. 154(b) by 88 days.

(21) Appl. No.: 11/843,411

(22) Filed: Aug. 22, 2007

(65) Prior Publication Data

US 2008/0249189 A1 Oct. 9, 2008

Related U.S. Application Data

(60) Provisional application No. 60/839,118, filed on Aug. 22, 2006.

(51) Int. Cl.
*A01N 25/00* (2006.01)
*A61K 31/515* (2006.01)
*A01N 43/52* (2006.01)
*A23L 1/22* (2006.01)
*A23L 2/56* (2006.01)
*A23G 3/00* (2006.01)

(52) U.S. Cl. ................ 514/772; 426/534; 426/660; 514/270; 514/387; 514/393

(58) Field of Classification Search ............... 426/660, 426/534; 514/270, 387, 393, 772; 544/139
See application file for complete search history.

(56) References Cited

U.S. PATENT DOCUMENTS

| 2,978,405 | A | * | 4/1961 | Bowers | 208/206 |
|---|---|---|---|---|---|
| 4,056,108 | A | * | 11/1977 | Schumacher et al. | 131/278 |
| 4,684,534 | A | | 8/1987 | Valentine | |
| 5,011,678 | A | | 4/1991 | Wang et al. | |
| 5,196,224 | A | * | 3/1993 | Van den Heuvel et al. | 426/535 |
| 6,060,078 | A | | 5/2000 | Lee | |
| 6,187,332 | B1 | | 2/2001 | Gern et al. | |
| 6,316,029 | B1 | | 11/2001 | Jain et al. | |
| 6,368,625 | B1 | | 4/2002 | Siebert et al. | |
| 6,403,142 | B1 | | 6/2002 | McDaniel, III et al. | |
| 6,649,186 | B1 | | 11/2003 | Robinson et al. | |
| 6,773,716 | B2 | | 8/2004 | Ream et al. | |
| 2005/0084506 | A1 | * | 4/2005 | Tachdjian et al. | 424/400 |
| 2006/0045953 | A1 | | 3/2006 | Tachdjian et al. | |

OTHER PUBLICATIONS

Avenet, P. and Lindemann, B., "Perspectives of Taste Reception," *J. Membrane Biol.* 112:1-8, Springer-Verlag (1989).

Doty, R.L., et al., "Influences of antihypertensive and antihyperlipidemic drugs on the senses of taste and smell: a review," *J. Hypertens.* 21:1805-1813, Lippincott Williams & Wilkins (2003).

Herness, M.S. and Gilbertson, T.A., "Cellular Mechanisms of Taste Transduction," *Annu. Rev. Physiol.* 61:873-900, Annual Reviews (1999).

Hofmann, T., et al., "TRPM5 Is a Voltage-Modulated and $Ca^{2+}$-Activated Monovalent Selective Cation Channel," *Curr. Biol.* 13:1153-1158, Cell Press (2003).

Huang, Y-J., et al., "The role of pannexin 1 hemichannels in ATP release and cell-cell communication in mouse taste buds," *Proc. Natl. Acad. Sci. U.S.A.* 104:6436-6441, National Academy of Sciences (Apr. 2007).

Kinnamon, S.C., "Taste transduction: a diversity of mechanisms," *Trends Neurosci.* 11:491-496, Elsevier Applied Science Publishing (1988).

Liu, D. and Liman, E.R., "Intracellular $Ca^{2+}$ and the phospholipid $PIP_2$ regulate the taste transduction ion channel TRPM5," *Proc. Natl. Acad. Sci. U.S.A.* 100:15160-15165, National Academy of Sciences (2003).

Margolskee, R.F., "Molecular Mechanisms of Bitter and Sweet Taste Transduction," *J. Biol. Chem.* 277:1-4, The American Society for Biochemistry and Molecular Biology (2002).

Pérez, C.A., et al., "A transient receptor potential channel expressed in taste receptor cells," *Nat. Neurosci.* 5:1169-1176, Nature Publishing Group (2002).

Prawitt, D., et al.,"TRPM5 is a transient $Ca^{2+}$-activated cation channel responding to rapid changes in $[Ca^{2+}]_i$," *Proc. Natl. Acad. Sci. U.S.A.* 100:15166-15171, National Academy of Sciences (2003).

Schiffman, S.S., "Taste and Smell Losses in Normal Aging and Disease," *J. Am. Med. Assoc.* 278:1357-1362, American Medical Association (1997).

(Continued)

*Primary Examiner*—Shengjun Wang
*Assistant Examiner*—Sarah Pihonak
(74) *Attorney, Agent, or Firm*—Sterne, Kessler, Goldstein & Fox PLLC

(57) ABSTRACT

The present invention is directed to the use of a compound of Formula I

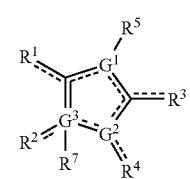

and physiologically acceptable salts thereof wherein $G^1$, $G^2$, $G^3$, $R^1$, $R^2$, $R^7$, $R^3$, $R^4$, and $R^5$ are defined herein. Compounds according to Formula I can be used to enhance a sweet taste produced by a tastant. The invention is also directed to compositions comprising a compound according to the above formula. Other aspects of the invention provide methods, compounds, and compositions for improved food products wherein the food product comprises a compound according to Formula I and a reduced amount of a sweet tastant.

20 Claims, 7 Drawing Sheets

OTHER PUBLICATIONS

Sørensen, L.B., et al., "Effect of sensory perception of foods on appetite and food intake: a review of studies on humans," *Int. J. Obes.* (Lond) 27:1152-1166, Nature Publishing Group (2003).

Ullrich, N.D., "Comparison of functional properties of the $Ca^{2+}$-activated cation channels TRPM4 and TRPM5 from mice," *Cell Calcium* 37:267-278, Churchill Livingstone (Mar. 2005).

Vissink, A., et al., "Prevention and Treatment of the Consequences of Head and Neck Radiotherapy," *Crit. Rev. Oral. Biol. Med.* 14:213-225, International Association for Dental Research (2003).

Zhang, Y., et al., "Coding of Sweet, Bitter, and Umami Tastes: Different Receptor Cells Sharing Similar Signaling Pathways," *Cell* 112:293-301, Cell Press (2003).

Bundgaard, H., ed., *Design of prodrugs*, Elsevier, Amsterdam, BE, pp. 7-9, 21-24 (1985).

International Search Report for International Application No. PCT/US07/18511, mailed on Sep. 12, 2008, United States Patent Office, Alexandria, VA.

\* cited by examiner

US 7,674,831 B2

HETEROCYCLIC COMPOUNDS AS SWEETENER ENHANCERS

The application claims the benefit of U.S. Provisional Application No. 60/839,118, filed Aug. 22, 2007, which is herein incorporated by reference in its entirety.

BACKGROUND OF THE INVENTION

1. Field of the Invention

The present invention relates to the use of compounds of Formula I for enhancing a sweet taste, masking an unpleasant taste by creating a sweet taste, and related uses. The invention is also directed to, among other things, compositions comprising a compound of Formula I that can be used in pharmaceutical, food, and other products as a sweetener enhancer or as a taste masking agent. In certain aspects, the invention provides methods and compositions for enabling one to prepare consumable products, such as food and pharmaceutical products, which retain a desired sweetness but contain lower amounts of sweetener, such as sugar, and in some cases fewer calories.

2. Background Art

Taste perception plays a critical role in the nutritional status and survival of both lower and higher animals (Margolskee, R. F., *J. Biol. Chem.* 277:1-4 (2002); Avenet, P. and Lindemann, B., *J. Membrane Biol.* 112:1-8 (1989)). The ability to taste has significance beyond providing people with pleasurable culinary experiences. For example, the ability to taste allows us to identify tainted or spoiled foods, and provides satisfying responses that may be proportionate to caloric or nutritive value.

There are generally considered to be only four or five categories of basic taste: sweet, sour, bitter, acid, and "umami" (the Japanese word describing the taste of monosodium glutamate; Hemess, M. S. & Gilbertson, T. A., 1999, Annu. Rev. Physiol. 61:873-900). These can be sub-classified as the appetitive tastes, such as salty, sweet and umami, which are associated with nutrient-containing foods, and the bitter and sour tastes elicited by toxic compounds.

The anatomic basis for the initial events of taste is the taste receptor cell ("TRC"), located in clusters referred to as "taste buds" (Lindemann, supra). Taste buds are distributed throughout the oral cavity, including the tongue as well as extra-lingual locations (see Hemess and Gilbertson). In the human tongue, taste buds are organized into three specialized types of specialized structures, namely fungiform, foliate, and circumvallate papillae. Each taste bud comprises between about 50 and 100 individual cells grouped into a cluster that is between 20 and 40 microns in diameter. Nerve fibers enter from the base of the taste bud and synapse onto some of the taste receptor cells. Typically, a single TRC contacts several sensory nerve fibers, and each sensory fiber innervates several TRCs in the same taste bud (Lindemann, supra).

When a subject ingests a tastant, and that tastant encounters a taste receptor cell in the appropriate concentration, an action potential is produced which, via synapses with primary sensory neurons, communicates the signal registered by the receptor, via afferent nerves, to the appropriate region of the sensory cortex of the brain, resulting in the perception of a particular taste by the subject.

Although taste perception is a vital function, sometimes it is useful to modify certain tastes. For example, many active pharmaceutical ingredients of medicines produce undesirable tastes, such as a bitter taste. Masking the bitter taste produced by the medicine by adding a sweetener enhancer may lead to improved acceptance by the patient.

Traditionally, sweeteners and flavorants have been used to mask the bitter taste of pharmaceuticals. The sweetener or flavorant is known to activate other taste pathways and at sufficiently high concentration this serves to mask the bitter taste of the pharmaceutical. Using large concentrations of sweeteners such as table sugar (sucrose) is undesirable because of the high number of calories and because it cannot be administered to diabetics. Artificial sweeteners such as aspartame and saccharin do not have these drawbacks but can have an undesirable aftertaste or present safety concerns if used in large quantities.

A number of other methods have been suggested to inhibit, alter, or mask unwanted tastes. However, the presently available compounds are lacking in desirable characteristics.

Another area in which enhancing sweet taste would be useful is in encouraging food intake in subjects who have an impaired ability to taste or in patients who have lost their appetites. Studies have shown increased food intake as palatability increased. Sorensen, et al., *Int. J. Obes. Relat. Metab. Disord.* 27(10):1152-66 (2003). For instance, certain drugs, such as antihypertensives and antihyperlipidemics, have been reported to produce untoward alterations in taste and may result in decreased food intake. Doty, et al., *J. Hypertens.* 21(10):1805-13 (2003). Taste impairment has also been associated with radiation treatments for head and neck cancer and this taste impairment has been considered to be one of the factors associated with reduces appetite and altered patterns of food intake. Vissink, et al., *Crit. Rev. Oral Biol. Med.* 14(3):213-25 (2003). Decreased food consumption has also been correlated with loss of taste sensations in the elderly. Shiffman, S. S., *J. Am. Med. Ass'n* 278(16):1357-1362 (1997). Enhancing the sweet taste of food could lead to increased consumption of foods containing these enhancers.

Therefore, there exists a need for compounds that can effectively enhance a sweet taste, preferably without exhibiting one or more of the limitations of the prior art sweetening agents.

BRIEF SUMMARY OF THE INVENTION

A first aspect of the present invention is directed to a method of enhancing a sweet taste, comprising administering to a subject a sweet tastant and one or more compounds of Formula I, or a physiologically acceptable salt thereof.

In certain aspects of the invention, as described further below, the methods and compositions of the present invention allow one to create food products with sufficient sweetness but with reduced levels of known sweet tastants, such as sugar. These methods also enable one to prepare an improved food product with the same level of sweetness as the original food product but with reduced calories from the caloric sweetness.

An additional aspect of the present invention is directed to a method of enhancing a sweet taste of a food product, comprising administering to a subject a food product comprising a sweet tastant and one or more compounds of Formula I, or a physiologically acceptable salt thereof.

An additional aspect of the present invention is directed to a method of enhancing a sweet taste of a pharmaceutical, comprising administering to a subject a pharmaceutical comprising a sweet tastant and one or more compounds of Formula I, or a physiologically acceptable salt thereof.

An additional aspect of the present invention is directed to a method of increasing the palatability of food and its intake comprising administering to a subject a food product comprising a sweet tastant and one or more compounds of Formula I to a subject in need of such treatment.

An additional aspect of the present invention is directed to a method of masking an undesirable taste of a food product, comprising administering to a subject a food product comprising a sweet tastant and one or more compounds of Formula I, or a physiologically acceptable salt thereof.

An additional aspect of the present invention is directed to a method of masking an undesirable taste of a pharmaceutical, comprising administering to a subject a pharmaceutical comprising a sweet tastant, one or more compounds of Formula I, or a physiologically acceptable salt thereof.

An additional aspect of the present invention is directed to a food product comprising a sweet tastant and one or more compounds according to Formula I or a physiologically acceptable salt thereof.

An additional aspect of the present invention is directed to a pharmaceutical composition comprising an active agent, optionally one or more pharmaceutically acceptable carriers, a sweet tastant, and one or more compounds of Formula I or a physiologically acceptable salt thereof.

These and additional aspects of the present invention are described in detail below.

BRIEF DESCRIPTION OF THE DRAWINGS/FIGURES

The accompanying drawings, which are incorporated herein and form a part of the specification, serve to explain the principles of the invention and to enable a person skilled in the pertinent art to make and use the invention.

FIG. 2 demonstrates that only TRPM5-transfected cells generate a membrane potential response while all cells, both sham and transfected, generate $Ca^{2+}$ signals.

Figure 3:
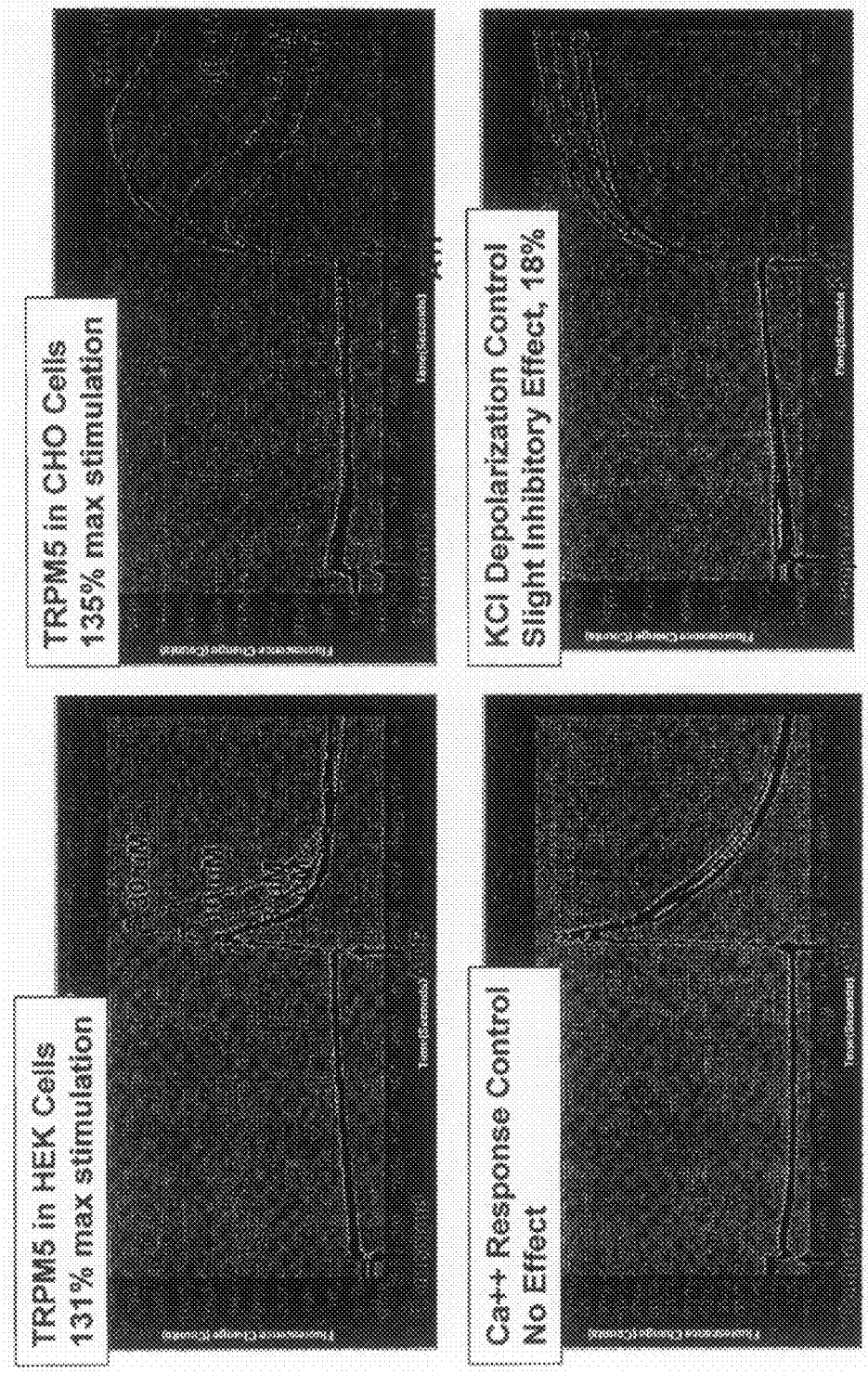

FIG. 3 illustrates the selective enhancement of TRPM5 activity by three different concentrations of the compound of Example 8. The upper left graph of FIG. 3 shows the effect of 1, 3, 10, and 30 micromolar ($\mu M$) of the compound of Example 8 on TRPM5 activity in hTRPM5-HEK293 cells, as measured in the fluorescent assays described herein. The upper right graph of FIG. 3 shows the effect of 1, 3, 10, and 30 $\mu M$ of the compound of Example 8 at on TRPM5 activity in CHO cells as measured in the fluorescent assays described herein. The lower left graph of FIG. 3 illustrates a calcium counterscreen assay, in which the hTRPM5-HEK293 cells were loaded with a calcium sensitive dye and stimulated by ATP to check to see if the compound of Example 8 blocks the GPCR-mediated calcium activated step. The lower right graph of FIG. 3 illustrates a KCl counterscreen, in which 1, 3, 10, and 30 $\mu M$ of the compound of Example 8 is added to hTRPM5-hTRPM5-HEK293 cells, stimulated by KCl instead of ATP to determine whether the compound was a specific ion channel enhancer. In these experiments TRPM5 was stimulated by another GPCR present in HEK and CHO cells using ATP as agonist.

Figure 4:
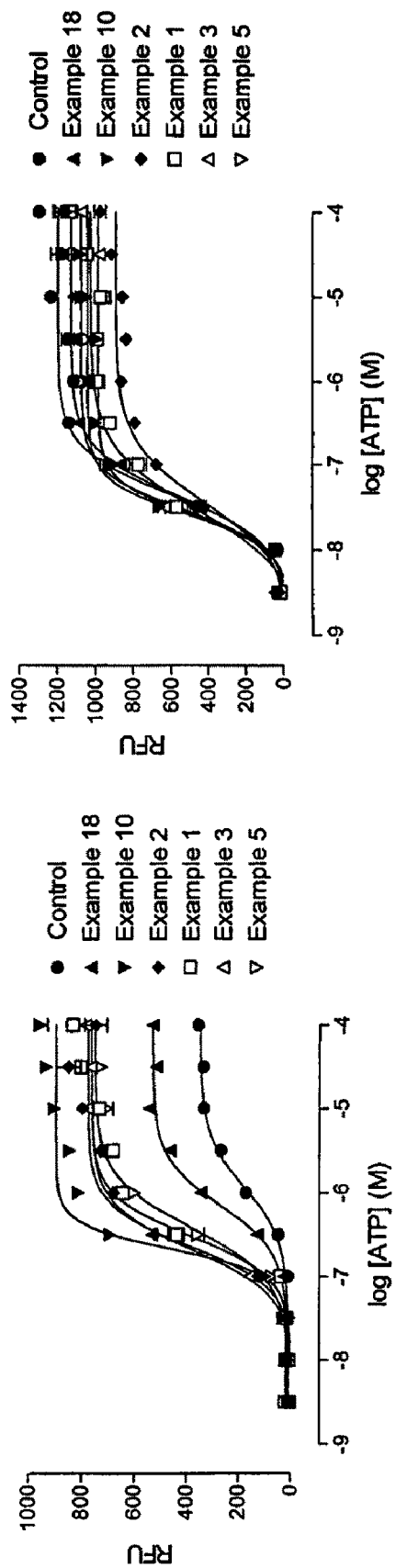

FIG. 4 illustrates the enhancement of TRPM5 activity (membrane potential response) as a function of ATP concentration with several different compounds. The compounds had little effect on calcium dye response to increasing ATP agonist levels. The results show selective enhancement of TRPM5 activity by the compounds of the invention at low concentrations of GPCR agonist ATP (a surrogate tastant). The left graph of FIG. 4 shows the effect of the addition of 30 micromolar of the compounds of Examples 1-3, 5, 10 and 18 on the ATP concentration-effect function for membrane potential in hTRPM5-HEK293 cells, as measured by the fluorescent assay described herein. The right graph shows the effect of the addition of a compound of the invention at 30 micromolar on ATP concentration-effect function for intracellular calcium in hTRPM5-HEK293 cells, as measured in the fluorescent assays described herein.

Figure 5:
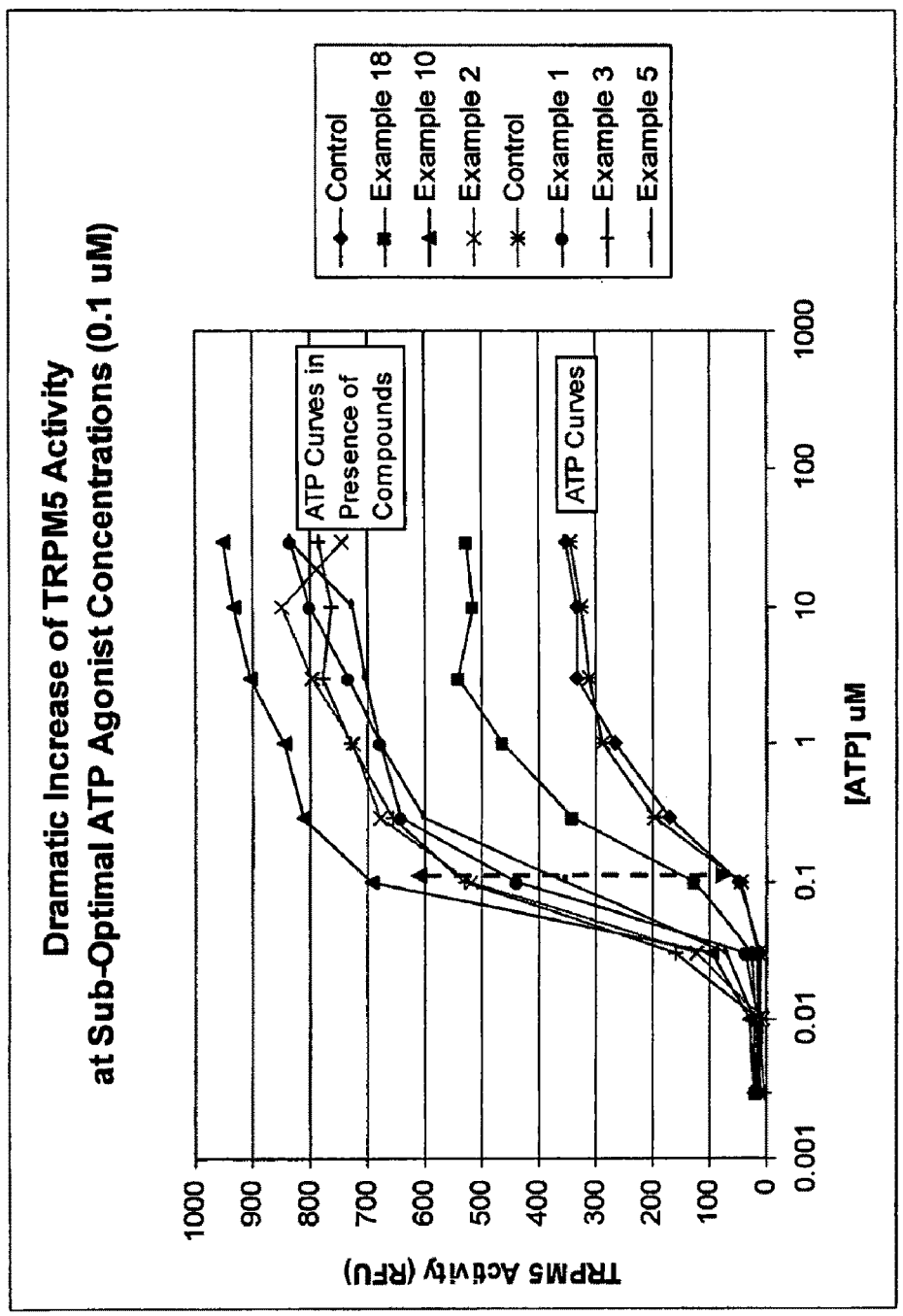

FIG. 5 illustrates the results of the selective enhancement of TRPM5 activity by the compounds of Examples 1-3, 5, 10, and 18. The results indicate a dramatic increase (>10×) of TRPM5 activity at sub-optimal ATP agonist concentrations (0.1 $\mu M$). At low ATP concentration, i.e. 0.1 uM, the ratio of ATP signal alone vs. the signal in the presence of the compounds in some cases is greater than 10 fold.

Figure 6:
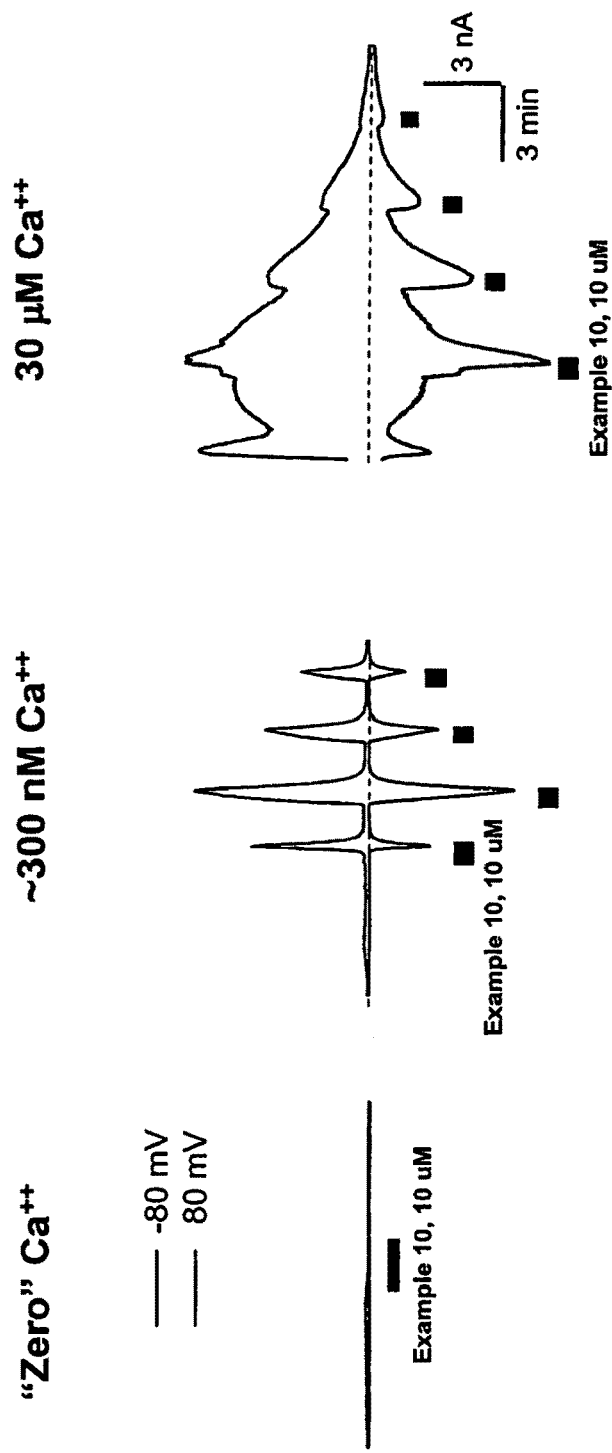

FIG. 6 illustrates stimulation of TRPM5 current when TRPM5 transfected HEK 393 cell are exposed to 10 $\mu M$ boluses (red bars) of the compound (Example 10) in a flow-through electrophysiological apparatus. The left graph of FIG. 6 shows no activation by compound in the absence of calcium. The central graph of FIG. 6 show a large >5 nA current (+80 mV) pulses in response to boluses of the compound at a calcium concentration of 300 nm. Note that the current drops off when the exposure of compound is stopped, i.e. the compound is washed away. The far right graph shows a stimulation of current by compound at 30 $\mu m$ calcium. While there is further stimulation of the TRPM5 current by compound at 30 uM, it is not as dramatic as at 300 nn Ca++. Note that no significant current was seen in non-transfected, sham HEK cells (not shown).

Figure 7:
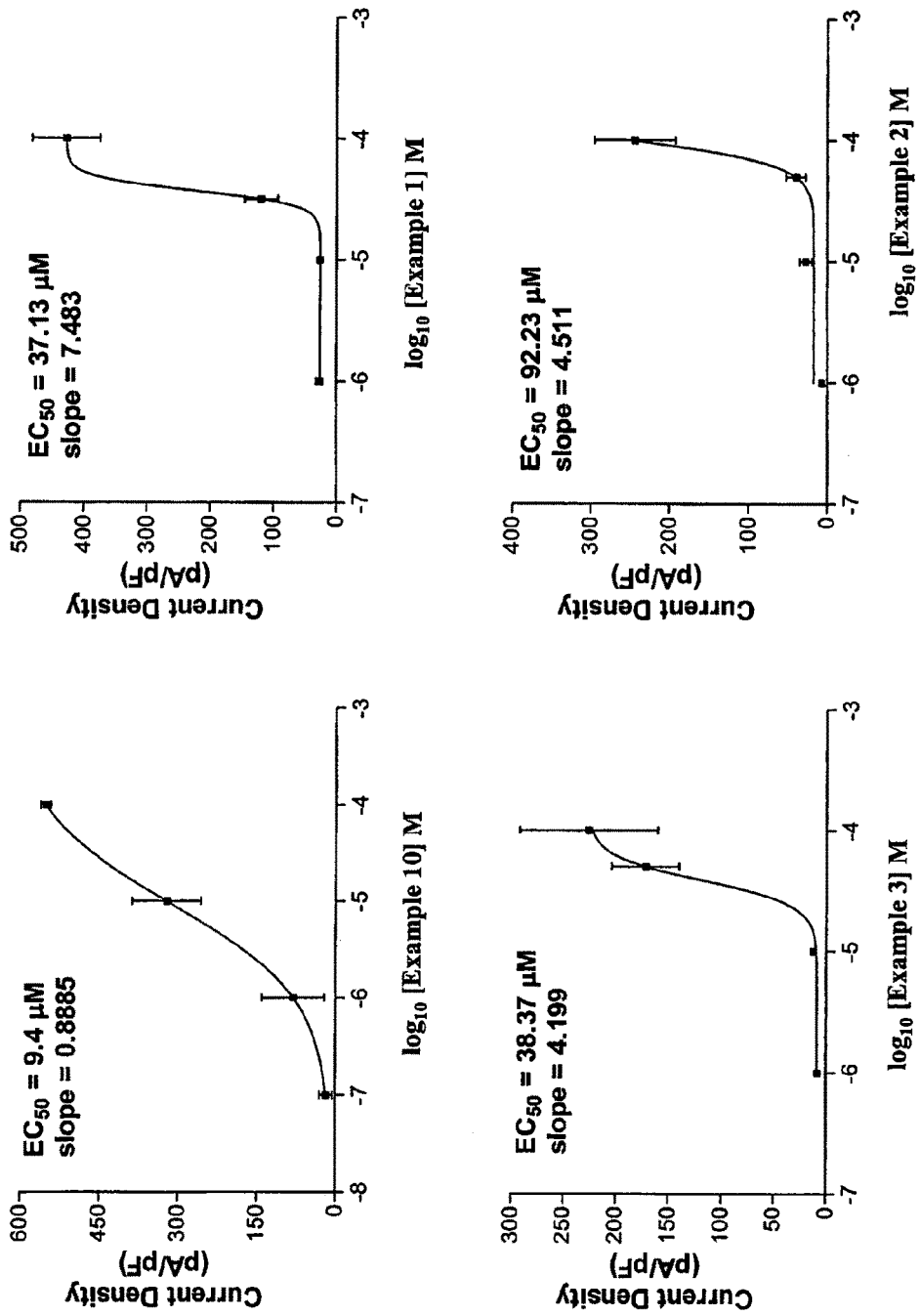

FIG. 7 shows dose-respose curve for enhancing the activity of TRPM5 protein in hTRPM5-HEK293 cells. The graphs show the effects of the compounds of Examples 1, 2, 3, and 10.

DETAILED DESCRIPTION OF THE INVENTION

The present invention provides compounds and compositions that are useful, for example, for enhancing sweet tastes. The methods of the present invention enable one to use a known sweetening agents, or sweet tastants, in a reduced amount combined with a compound according to Formula I, or any of the specific subgroups or specific compounds described herein, in order to achieve the same level of sweetness when the known sweet tastant is used alone in the traditional amount. By way of brief example, a common carbonated cola beverage may contain about 20 to 30 grams of sugar (e.g., fructose) and about 100 calories per 8 ounce serving. The present invention enables one to prepare a similar cola beverage with substantially reduced sugar and caloric content but with the same level of sweetness. The compounds identified in here, e.g., according to Formula I, enhance the sweet taste produced by the reduce sugar content, thereby creating an enhanced sweet taste based on the reduced level of sweet tastant, e.g., table sugar.

Other aspects of the present invention are described in detail herein.

Methods of Use

A first aspect of the present invention is directed to a method of enhancing a sweet taste, said method comprising administering to a subject a sweet tastant and a compound of Formula I or a physiologically acceptable salt thereof,

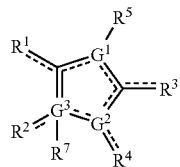

I wherein

G¹, G², and G³ are independently selected from N, S, and C;

R¹ and R² are independently absent or selected from hydrogen, $C_{1-6}$ alkyl, halogen, nitro, optionally substituted $C_{6-14}$ aryl, optionally substituted 5-14 membered heteroaryl, optionally substituted 5- and 14-membered heteraryloxy, optionally substituted 5-14 membered heterarylthio, Ar-Q, optionally substituted $(CH_2)_nC(\!=\!O)\!-\!O\!-\!R^{2a}$, and optionally substituted $(CH_2)_nC(\!=\!O)$aryl, or R¹ and R², together with the G³ and the carbon atom to which R¹ is attached, form a $C_{6-14}$ aryl or 5- to 14-membered heterocycle, each of which is optionally substituted; or if the bond to R¹ and/or R² is a double bond, then R¹ and R² are independently selected from =NH and =O;

R³ is selected from H, $C_{1-6}$ haloalkyl, $C_{1-6}$ alkyl, oxo, =NH, optionally substituted $C_{6-14}$ aryl, and optionally substituted 5-14 membered heterocycle, or R³ is $L^1$-$R^{31}$, such as $=Z^1$-$(CH_2)_n$-$Z^2$-$R^{31}$ or;

R⁴ is absent or is selected from the group consisting of H, $C_{1-6}$ alkyl, $C_{1-6}$ alkenyl, $C_{1-6}$ alkoxy, $C_{1-6}$ hydroxyalkyl, optionally substituted $C_{6-14}$ aryl, and optionally substituted $(CH_2)_nC(\!=\!O)$aryl, or when the bond to R⁴ is a double bond, R⁴ is =O; and R⁵ is either absent or is selected from hydrogen, $C_{1-6}$ alkyl, and optionally substituted phenyl amide;

R⁷ is either absent or selected from H and $C_{1-6}$ alkyl;

$R^{2a}$ is $C_{1-6}$ alkyl;

$R^{31}$ is H, $C_{1-6}$ alkyl, $C_{1-6}$ alkenyl, optionally substituted phenyl, amino, $C_{1-6}$ alkylamino, or $C_{1-6}$ dialkylamino;

$Z^1$ is selected from =N, —NH, O, and S;

$Z^2$ is O, S, C(=O), C(=S), —C(=O)—O, C(=S)—O, —C(=O)—NH—, or —C(=S)—NH;

$L^1$ is linker containing 1 to 30 carbon and/or heteroatoms;

Q is $CH_2$, O, NH, or S;

Ar is optionally substituted aryl or optionally substituted heteroaryl; and n is 0 to 10.

Preferred groups of compounds within Formula I to be used in the methods of the present invention include

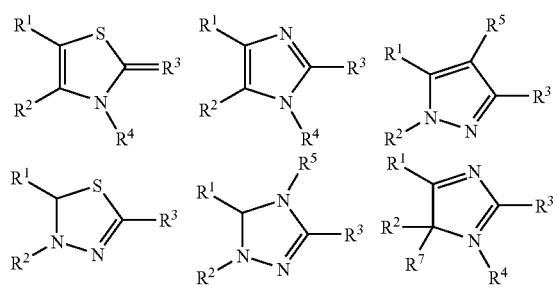

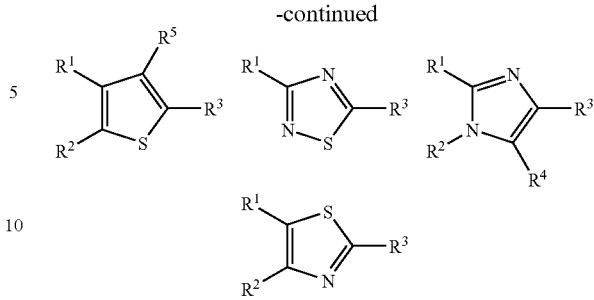

wherein R¹-R⁵ are defined as above.

Each of the bonds in the five-membered ring of Formula I may be a single or double bond. In one embodiment, the ring formed from G¹, G², and G³ contains only single bonds. In another embodiment, the ring formed from G¹, G², and G³ contains one or two double bonds.

In one embodiment, one of G¹, G², and G³ is carbon, and the others are selected from N or S. In a further embodiment, G³ is carbon, and G¹ and G² are selected from N or S. In a further embodiment, G³ is carbon, one of G¹ and G² is N, and the other is S. In a further embodiment, G³ is carbon, and both G¹ and G² are N. In a further embodiment G² is carbon, and G¹ and G³ are selected from N or S In another embodiment, one of G¹, G², and G³ is S, and the others are N. In another, G¹, G², and G³ are N. In another, G¹ is S, and G² and G³ are carbon.

In another embodiment, G¹, G², and G³ are selected to form one of the following groups:

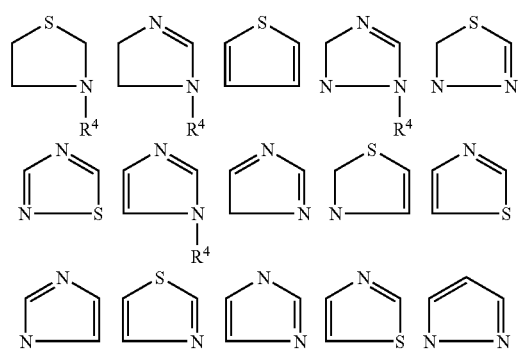

In one embodiment, R¹ and R² are independently optionally substituted $C_{6-10}$ aryl, such as phenyl or naphthyl. In another embodiment, R¹ and/or R² are an optionally substituted 5-10 membered, preferably 5-7 membered, heteroaryloxy or heteroarylthio. The heteroaryl includes but is not limited to pyridyl, pyrimindinyl, imidazolyl, tetrazolyl, furanyl, thienyl, indolyl, azaindolyl, quinolinyl, pyrrolyl, benzimidazolyl, and benzothiazolyl, each of which is optionally substituted. In other instances, the heteroaryl group is a 5-10 membered, preferably 5-7 membered, nitrogen-containing heteroaryl.

Another subset of R¹ and R² includes a substituted aryl or heteroaryl group having 1-3 substituents independently selected from the group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy $(C_{1-6})$alkyl, $C_{1-6}$ aminoalkyl, $C_{1-6}$ hydroxyalkyl, $C_{2-6}$ hydroxyalkoxy, mono$(C_{1-4})$alkylamino, di$(C_{1-4})$alkylamino, $C_{2-6}$ alkylcarbonylamino, $C_{2-6}$ alkoxycarbonylamino, $C_{2-6}$alkoxycarbonyl, carboxy, $C_{2-6}$ carboxyalkoxy, and $C_{2-6}$ carboxyalkyl.

In another embodiment, $R^1$ and $R^2$ are independently a $C_{3-10}$ ester or $C_{1-6}$ alkyl-C(=O)—Ar, wherein Ar is an optionally substituted phenyl. In a further embodiment, Ar is optionally substituted by 1-3 substituent selected from the group consisting of amino, hydroxy, nitro, halogen, $C_{1-6}$ alkyl, $C_{1-6}$ haloalkyl, and $C_{1-6}$ alkoxy.

In another embodiment, the bond to $R^1$ and/or $R^2$ is a double bond, and $R^1$ and $R^2$ are independently selected from =NH and =O. More specifically, both the bond from the ring to $R^1$ or $R^2$ can be either a single bond or a double bond. When the bond to $R^1$ is a single bond, $R^1$ is selected from hydrogen, $C_{1-6}$ alkyl, halogen, nitro, optionally substituted $C_{6-14}$ aryl, optionally substituted 5- to 14-membered heteroaryloxy, optionally substituted 5-14 membered heteroarylthio, optionally substituted $CH_3(CH_2)_nC(=O)$—O—R, and optionally substituted $CH_3(CH_2)_nC(=O)$aryl. When the bond to $R^1$ is a double bond, $R^1$ is either NH or O. $R^2$ is defined likewise.

In another embodiment, $R^1$ and $R^2$, together with the $G^3$ and the carbon atom to which $R^1$ is attached, form an optionally substituted $C_{6-14}$ aryl, such as phenyl or naphthyl, or an optionally substituted 5-14 membered heterocycle, such as but not limited to pyridyl, pyrimindinyl, imidazolyl, tetrazolyl, furanyl, thienyl, indolyl, azaindolyl, quinolinyl, pyrrolyl, benzimidazolyl, diazole, triazole, thiazole, thiadiazole, thiatriazole, benzothiophene, benzothiopyran, and benzopyran. In other instances, the heterocycle group is a nitrogen-containing and/or sulfur-containing heterocycle.

In another subset of $R^1$ and $R^2$, $R^1$ and $R^2$, together with the $G^3$ and the carbon atom to which $R^1$ is attached, form a $C_{6-14}$ aryl or a 5-14 membered heterocycle having 1-3 substituents independently selected from the group consisting of amino, hydroxy, nitro, halogen, cyano, thiol, oxo, $C_{1-6}$ alkyl, $C_{2-6}$ alkenyl, $C_{1-6}$ haloalkyl, $C_{1-6}$ alkoxy, $C_{1-6}$ alkenyloxy, and optionally substituted $C_{6-14}$ aryl. In a further embodiment, the ring formed from $R^1$ and $R^2$ together with the $G^3$ and the carbon atom to which $R^1$ is attached is substituted by a $C_{6-14}$ aryl, optionally containing one or more $C_{1-6}$ alkyl, halo, $C_{1-6}$ haloalkyl or nitro groups.

Alternatively, $R^1$ and $R^2$ may be independently Ar-Q, wherein Q is $CH_2$, O, NH, or S, and Ar is optionally substituted aryl or optionally substituted heteroaryl. Preferably, Ar is optionally substituted $C_{6-14}$ aryl or optionally substituted 5-14 membered heteroaryl. Suitable Ar-Q groups include optionally substituted 5- to 14-membered heteroaryloxy and optionally substituted 5-14 membered heteroarylthio.

In another embodiment, $G^1$, $G^2$, and $G^3$ along with $R^1$, $R^2$, form a heterocycle ring system selected from:

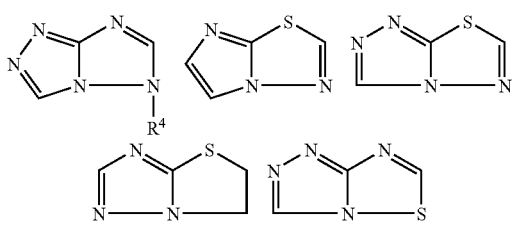

In one embodiment, $R^3$ is optionally substituted $C_{6-10}$ aryl, such as phenyl or naphthyl. In another embodiment, $R^3$ is optionally substituted 5-10 membered, or preferably 5-7 membered, heterocycle, such as, but not limited to pyrrolidyl, piperidyl, diazacyclopentyl, triazacyclopentyl, azacyclohexyl, diazacyclohexyl, triazacyclohexyl, azacycloheptyl, diaazacycloheptyl, triazacyclohepyl, azacyclopentenyl, diazacyclopentenyl, triazacyclopentenyl, azacyclohexenyl, diazacyclohexenyl, triazacyclohexenyl, azacycloheptenyl, diazacycloheptenyl, and triazacycloheptenyl. In a further embodiment, $R^3$ is selected from a diazacycheptyl and a diazacyclohexenyl. In a further embodiment, $R^3$ is either 1,4-diazacycloheptyl or 1,5-diazacyclohex-2-en-3-yl.

Another subset of $R^3$ includes a substituted aryl group having 1-3 substituents independently selected from the group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, and $C_{3-6}$ alkenyloxy. In a further embodiment $R^3$ is substituted by one or more of nitro, halogen, $C_{1-6}$ alkyl, and $C_{1-6}$ alkoxy.

Another subset of $R^3$ includes a substituted heterocycle group having 1-4 substituents independently selected from the group consisting of amino, hydroxy, nitro, oxo (i.e. =O), halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkyl-Ar, Ar, and —C(=O)—NH—Ar, wherein Ar is an optionally substituted phenyl. In a further embodiment, Ar is optionally substituted by 1 to 3 substituents selected from the group consisting of nitro, halogen, $C_{1-6}$ alkyl, and $C_{1-6}$ alkyloxy.

In another embodiment, $R^3$ is $L^1$-$R^{31}$, wherein $L^1$ is a linker containing 1 to 30 carbon atoms and/or heteroatoms and $R^{31}$ is selected from the group consisting of H, $C_{1-6}$ alkyl, $C_{1-6}$ alkenyl, optionally substituted phenyl, amino, $C_{1-6}$ alkylamino, or $C_{1-6}$ dialkylamino.

The linker $L^1$ can comprise various carbon- and/or heteroatom-containing moieties. The size of the linker can be from 1 (e.g., $CH_2$, O, NH, etc.) to 30 carbon atoms and/or heteroatoms. The number of carbon atoms and/or heteroatoms does not, of course, include hydrogen atoms. In certain instances, the linker is an alkylene linker containing only carbon and hydrogen atoms. In other instances, the linker is a heteroalkylene linker containing carbon and hydrogen atoms and also one or more heteroatoms, such as nitrogen, oxygen, and sulfur. The linker can be straight-chained or branched. The linker may comprise one or more cyclic groups, either as the whole linker or as part of the linker group. The cyclic group may be carbocyclic or heterocyclic. The linker may be optionally substituted.

The linker group of $L^1$ may saturated or unsaturated. Certain linker groups may contain one or more double bonds.

In a preferred embodiment, the linker contains at least one heteroatom, and contains 2-15, preferably 2-10, carbon atoms and heteroatoms. Other suitable linker groups for $L^1$ include =N—$CH_2$C(O)O$CH_2$—, —S$CH_2$$CH_2$O—, =NC(S)NH$CH_2$CH=, —C(O)NH—, and —NHC(O)$CH_2$—. Alternatively, $L^1$ may be -Het-C(O)—NH— wherein Het is a 5- to 7-membered nitrogen-containing heterocycle In other instances, the linker group comprises a 5-7 membered cyclic, preferably heterocyclic moiety. The linker group may contain 1-4, preferably 1-2 heteroatoms.

In another instance, $L^1$ is one of the following linker groups:

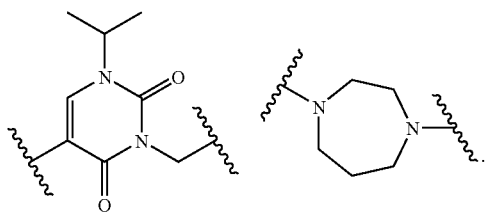

In another embodiment, $L^1$-$R^{31}$ is $=Z^1$-$(CH_2)_n$-$Z^2$-$R^{31}$ wherein:

$Z^1$ is N, NH, O, or S;

n is 0 to 4, preferably 1 or 2;

$Z^2$ is O, S, C(=O), C(=S), —C(=O)—O, C(=S)—O, —C(=O)—NH— or —C(=S)—NH; and $R^{31}$ is selected from $C_{1-6}$ alkyl, $C_{1-6}$ alkenyl, optionally substituted phenyl, and —(CH$_2$)—NR'R" wherein R' and R" are selected from H and $C_{1-6}$ alkyl.

In a further embodiment, $R^{31}$ is a substituted aryl, such as substituted phenyl containing 1 to 3 substituents independently selected from the group consisting of nitro, halogen, hydroxy, $C_{1-6}$ haloalkyl, $C_{1-6}$ alkyl, and $C_{1-6}$ alkyloxy.

Another preferred compound of Formula I for use in the methods of the present invention is a compound according to the formula:

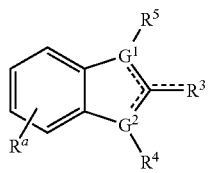

wherein $R^3$ is $L^1$-$R^{31}$; $R^4$ is absent, H, $C_{1-6}$ alkyl, or $C_{1-6}$ hydroxyalkyl; $R^5$ is absent, H, or $C_{1-6}$ alkyl; $R^a$ is H or $C_{1-6}$ alkyl; and $G^1$ and $G^2$ are independently C, N, or S.

A preferred compound of Formula I for use in the methods of the present invention is a compound according to the formula:

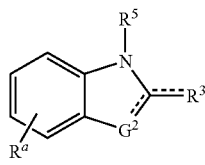

wherein $R^3$ is $L^1$-$R^3$; $R^5$ is H or $C_{1-6}$ alkyl; G is N or S; and $R^a$ represents H or $C_{1-6}$ alkyl.

Another preferred compound for use in the methods of the present invention is a compound according to the formula:

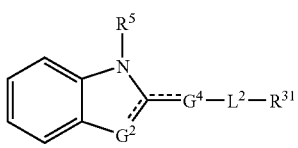

wherein $G^2$ is N or S; $R^5$ is H or $C_{1-6}$ alkyl; $G^4$ is N, S, or O; $L^2$ is a linker containing 1-10 carbon and/or heteroatoms; and $R^{31}$ is H or optionally substituted phenyl.

Another preferred compound of Formula I for use in the methods of the present invention is a compound according to the formula:

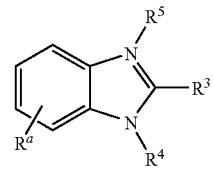

wherein $R^3$ is $L^1$-$R^{31}$; $R^4$ is H, $C_{1-6}$ alkyl, or $C_{1-6}$ hydroxyalkyl; $R^5$ is absent; and $R^a$ is H or $C_{1-6}$ alkyl.

Another preferred compound of Formula I for use in the methods of the present invention is a compound according to the formula:

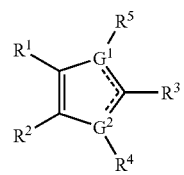

wherein $R^1$ and $R^2$ are independently selected from the group consisting of H, $C_{1-6}$ alkyl, $C_{1-6}$ alkoxycarbonyl, and Ar-Q, wherein Q is O, NH, S, or $CH_2$, and Ar is an optionally substituted aryl or optionally substituted heteroaryl; $R^3$ is H or $C_{1-6}$ alkyl; $R^4$ is absent, H, or $C_{1-6}$ alkyl; $R^5$ is absent, H, or $C_{1-6}$ alkyl; and $G^1$ is C or N; and $G^2$ is N or S.

Another preferred compound of Formula I for use in the methods of the present invention is a compound according to the formula:

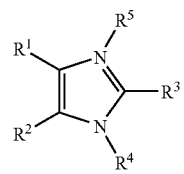

wherein $R^1$ and $R^2$ are independently selected from the group consisting of H, $C_{1-6}$ alkyl, $C_{1-6}$ alkoxycarbonyl, and Ar-Q, wherein Q is O, NH, S, or $CH_2$, and Ar is an optionally substituted aryl or optionally substituted heteroaryl; $R^3$ is H or $C_{1-6}$ alkyl; $R^4$ is H or $C_{1-6}$ alkyl; and $R^5$ is absent.

Another preferred compound of Formula I for use in the methods of the present invention is a compound according to the formula:

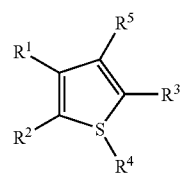

wherein $R^1$ and $R^2$ are independently selected from the group consisting of H, $C_{1-6}$ alkyl, $C_{1-6}$ alkoxycarbonyl, and Ar-Q, wherein Q is O, NH, S, or $CH_2$, and Ar is an optionally substituted aryl or optionally substituted heteroaryl; $R^3$ is H or $C_{1-6}$ alkyl; $R^4$ is absent; and $R^5$ H or $C_{1-6}$ alkyl.

Another preferred compound of Formula I for use in the methods of the present invention is a compound according to the formula:

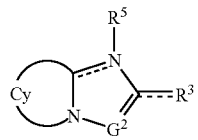

wherein $R^3$ is $L^1$-$R^{31}$; $R^5$ is H or $C_{1-6}$ alkyl; $G^2$ is C, N, or S; and Cy represents an optionally substituted fused ring comprising 5-10, preferably 5-7, carbon atoms and/or heteroatoms.

Another preferred compound of Formula I for use in the methods of the present invention is a compound according to the formula:

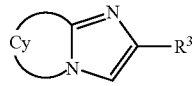

wherein $R^3$ is $L^1$-$R^{31}$; and Cy represents an optionally substituted fused ring comprising 5-10, preferably 5-7, carbon atoms and/or heteroatoms. Alternatively, $R^3$ represents optionally substituted aryl, such as phenyl, and the Cy group contains one or more nitrogen and/or sulfur atoms.

Another preferred compound of Formula I for use in the methods of the present invention is a compound according to the formula:

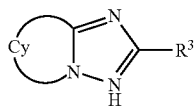

wherein $R^3$ is $L^1$-$R^{31}$; and Cy represents an optionally substituted fused ring comprising 5-10, preferably 5-7, carbon atoms and/or heteroatoms.

Another preferred compound of Formula I for use in the methods of the present invention is a compound according to the formula:

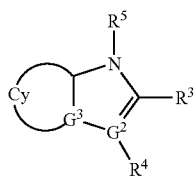

wherein $R^3$ is $L^1$-$R^{31}$; $R^5$ is H or $C_{1-6}$ alkyl; $G^2$ is C, N, or S; $G^3$ is C or N; $R^4$ is H or absent; and Cy represents an optionally substituted fused ring comprising 5-10, preferably 5-7, carbon atoms and/or heteroatoms.

Another preferred compound of Formula I for use in the methods of the present invention is a compound according to the formula:

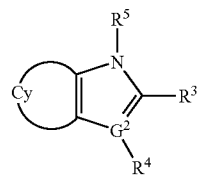

wherein $R^3$ is $L^1$-$R^{31}$; $R^4$ is H or absent; $R^5$ is H or $C_{1-6}$ alkyl; $G^2$ is C or N; and Cy represents an optionally substituted fused ring comprising 5-10, preferably 5-7, carbon atoms and/or heteroatoms.

Another preferred compound of Formula I for use in the methods of the present invention is a compound according to the formula:

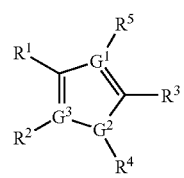

wherein $R^1$ is $C_{1-6}$ alkyl or optionally substituted $C_{6-10}$ aryl; $R^2$ is H or absent; $R^3$ is $L^1$-$R^{31}$; $R^4$ is H or absent; $R^5$ is H or absent; $R^{31}$ is a linker, preferably comprising 2 to 20 carbon atoms and/or heteroatoms; $G^1$ is N or C; $G^2$ is N or S; and $G^3$ is N or C.

Another preferred compound of Formula I for use in the methods of the present invention is a compound according to formula:

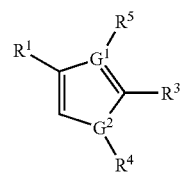

wherein $R^1$ is $C_{1-6}$ alkyl or optionally substituted $C_{6-10}$ aryl; $R^3$ is $L^1$-$R^{31}$; $R^4$ is H or absent; $R^5$ is H or absent; $G^1$ is N or C; and $G^2$ is N or S.

Another preferred compound of Formula I for use in the methods of the present invention is a compound according to formula:

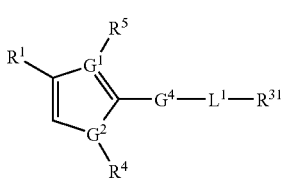

wherein $R^1$ is $C_{1-6}$ alkyl or optionally substituted $C_{6-10}$ aryl; $R^4$ is H or absent; $R^5$ is H or absent; $G^1$ is N or C; $G^2$ is N or S; $G^4$ is NH, S, or O; $L^1$ is a linker containing 1-10 carbon atoms and/or heteroatoms; and $R^{31}$ is H, $NR^aR^b$ or optionally substituted phenyl, wherein $R^a$ and $R^b$ are independently H or $C_{1-6}$ alkyl.

In a first subclass, the present invention is directed to a method of enhancing a sweet taste, said method comprising utilizing a compound of Formula II

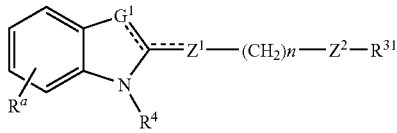

II wherein: $R^4$ is H, $C_{1-6}$ alkyl, or $C_{1-6}$ hydroxyalkyl;
$R^{31}$ is H, $C_{1-6}$ alkyl, $C_{1-6}$ alkenyl, or optionally substituted phenyl, preferably optionally substituted by one or more of $C_{1-6}$ alkyl, $C_{1-6}$ alkoxy and hydroxyl;
$R^a$ is H or $C_{1-6}$ alkyl, preferably H;
$G^1$ is S or N;
$Z^1$ is S or N;
$Z^2$ is $-C(=O)-O-$, $-C(=S)-O-$, $-O-$, $-S-$, $-C(=O)-NH-$, or $-C(=S)-NH-$; and
n is 0 to 4, preferably 1 or 2.

In one embodiment within the first subclass, the compound of Formula II is selected from a compound of Formula III:

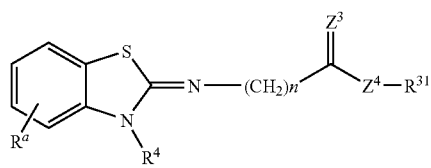

III wherein $R^4$ is H, $C_{1-6}$ alkyl, or $C_{1-6}$ hydroxyalkyl;
$R^{31}$ is selected from H, $C_{1-6}$ alkyl, and $C_{1-6}$ alkenyl;
$R^a$ is H or $C_{1-6}$ alkyl, preferably H;
$Z^3$ is O or S;
$Z^4$ is O, S, or NH; and
n is 0 to 3.

In a further embodiment within the first subclass, the compound of Formula III is selected from a compound of Formula IV:

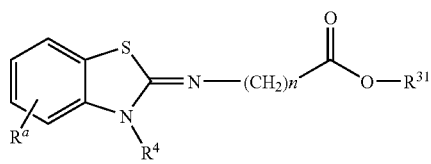

IV wherein $R^4$ is selected from H and $C_{1-6}$ alkyl;
$R^{31}$ is H or $C_{1-6}$ alkyl;
$R^a$ is H or $C_{1-6}$ alkyl; and
n is 0 to 3.

In a further example of this embodiment, $R^{31}$ is alkyl, preferably ethyl. In another example, $R^4$ is alkyl, preferably methyl. In another, n is 1. In another, $R^a$ is hydrogen In a further embodiment within the first subclass, the compound of Formula III is selected from a compound of Formula V:

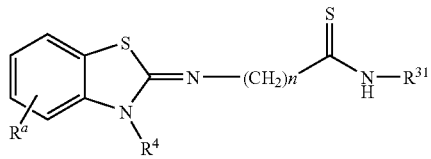

V wherein $R^2$ is H or $C_{1-6}$ alkyl;
$R^3$ is H, $C_{1-6}$ alkyl, or $C_{1-6}$ alkenyl;
$R^4$ is selected from H and $C_{1-6}$ alkyl; and
n is 0, 1, 2, or 3.

In one example of this embodiment, $R^4$ is alkyl, preferably methyl. In another example, $R^a$ is hydrogen. In another, n is zero. In another, $R^{31}$ is alkenyl, preferably 2-propenyl.

In a further embodiment within the first subclass, the compound of Formula II is selected from a compound of Formula VI

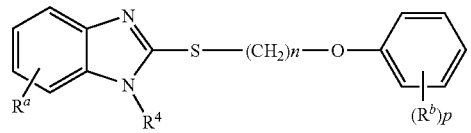

VI wherein $R^4$ is selected from H, $C_{1-6}$ alkyl, and $C_{1-6}$ hydroxyalkyl;
$R^a$ is H or $C_{1-6}$ alkyl;
$R^b$ is $C_{1-6}$ alkyl, $C_{1-6}$ alkyloxy, or hydroxy;
n is 0 to 3; and
p is 0 to 5.

In one example of this embodiment within the first subclass, $R^a$ is hydrogen. In another, $R^4$ is hydroxyalkyl, preferably 2-hydroxyethyl. In another, $R^4$ is hydrogen. In another, n is 2 or 3. In another embodiment, $R^b$ is alkyloxy, preferably methoxy. In another, the phenyl ring containing $(R^b)_p$ is 2,6-dimethoxyphenyl or 2-methoxyphenyl.

In a second subclass, the present invention is directed to a method of enhancing a sweet taste, said method comprising utilizing a compound of Formula VIII:

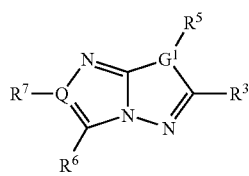

VIII wherein $G^1$ is N or S;
Q is N or C;
$R^3$ is H or optionally substituted phenyl, preferably optionally substituted by one or more selected from the group consisting of $C_{1-6}$ alkyl, $C_{1-6}$ alkoxy, hydroxyl, halogen, and nitro;
$R^5$ is H when $G^1$ is N, or otherwise is absent;
$R^6$ is selected from H and $C_{1-6}$ alkyl; and $R^7$ is selected from H, $C_{1-6}$ alkyl, and optionally substituted phenyl, preferably optionally substituted by one or more of $C_{1-6}$ alkyl, $C_{1-6}$ alkoxy, halogen, hydroxyl or nitro, or, when Q is N, $R^7$ is absent.

In one embodiment within this second subclass, $R^3$ is hydrogen. In another embodiment, $R^3$ is an optionally substituted phenyl, preferably optionally substituted by one or more of halogen or nitro. In another, $R^7$ is hydrogen or tolyl.

In another embodiment within this second subclass, the compound of Formula VIII is selected from a compound of Formula IX,

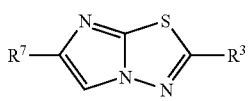

IX wherein $R^3$ is H, $C_{1-6}$ alkyl, or optionally substituted phenyl, preferably optionally substituted by one or more of $C_{1-6}$ alkyl, $C_{1-6}$ alkoxy, halogen, hydroxyl, or nitro; and $R^7$ is selected from H, $C_{1-6}$ alkyl, and optionally substituted phenyl, preferably optionally substituted by one or more of $C_{1-6}$ alkyl, $C_{1-6}$ alkoxy, halogen, hydroxyl or nitro.

In a further example of this embodiment, $R^3$ is hydrogen. In another, $R^7$ is an optionally substituted phenyl, preferably optionally substituted by one or more of $C_{1-6}$ alkyl, $C_{1-6}$ alkoxy, halogen, hydroxyl or nitro; or $R^7$ is a tolyl group.

A further embodiment within this second subclass is a compound of Formula IX, wherein: $R^3$ is H or $C_{1-6}$ alkyl, preferably H; and $R^7$ is selected from H, $C_{1-6}$ alkyl, and optionally substituted phenyl, preferably optionally substituted by one or more of $C_{1-6}$ alkyl, $C_{1-6}$ alkoxy, halogen, hydroxyl or nitro, or preferably $R^7$ is an optionally substituted phenyl. In one embodiment, $R^7$ is a tolyl group.

In a further embodiment within this second subclass, the compound of Formula VIII is selected from a compound of Formula X:

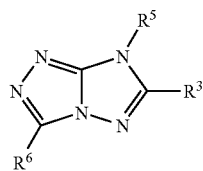

X wherein $R^3$ is selected from H, $C_{1-6}$ alkyl, and $C_{6-10}$ aryl, preferably optionally substituted phenyl, preferably optionally substituted with one or more of $C_{1-6}$ alkyl, $C_{1-6}$ alkoxy, halogen, hydroxyl, or nitro; $R^5$ is H; and $R^6$ is selected from H and $C_{1-6}$ alkyl.

In a further embodiment within this second subclass, the compound of Formula VIII is selected from a compound of Formula X, wherein $R^3$ is $C_{6-10}$ aryl, preferably phenyl, optionally substituted with one or more of $C_{1-6}$ alkyl, $C_{1-6}$ alkoxy, halogen, or nitro; and $R^6$ is H or $C_{1-6}$ alkyl. In one embodiment, $R^3$ is substituted by one or more halogen and/or a nitro groups. In another embodiment, $R^3$ is 3-nitro-4-chlorophenyl or $C_{1-6}$ alkyl, preferably ethyl.

In a third subclass, the present invention is directed to a method of enhancing a sweet taste, said method comprising utilizing a compound of Formula XI:

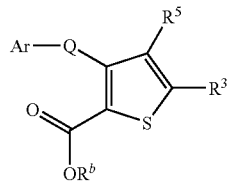

XI wherein $R^3$ is H or $C_{1-6}$ alkyl, preferably hydrogen;

$R^5$ is H or $C_{1-6}$ alkyl, preferably hydrogen;

Ar is a 5- to 10-membered aryl or heteroaryl group, preferably a 5- or 6-membered nitrogen containing heteroaryl group, optionally substituted with one or more groups independently selected from the group consisting of $NO_2$, halogen, $C_{1-6}$ alkyl, and $C_{1-6}$ hydroxyalkyl;

Q is O or NH;

$R^b$ is H or $C_{1-6}$ alkyl; and n is 0 to 3.

In one embodiment of this third subclass, $R^1$ is a $C_{1-6}$ alkyl, preferably methyl. In another embodiment Q is oxygen. In another, Ar is a 5- or 6-membered nitrogen containing heteroaryl group, preferably pyridyl. In another, $R^2$ is nitro. In another, n is one.

In another embodiment within this third subclass, the present invention is directed to a method of enhancing a sweet taste, said method comprising utilizing a compound of Formula XII:

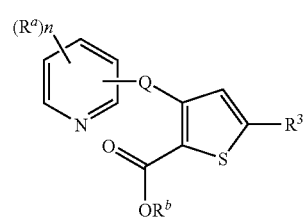

XII wherein $R^3$ is H or $C_{1-6}$ alkyl;

each occurrence of $R^a$ is independently selected from the group consisting of $NO_2$, halogen, $C_{1-6}$ alkyl, or $C_{1-6}$ hydroxyalkyl;

$R^b$ is H or $C_{1-6}$ alkyl; and n is 0 to 3.

In one example of this embodiment, $R^1$ is $C_{1-6}$ alkyl, preferably methyl. In another, $R^3$ is hydrogen. In another, n is 1. In another, $R^2$ is nitro. In another, the pyridine ring is attached to the oxygen atom at the 2-position.

In a fourth subclass, the present invention is directed to a method of enhancing a sweet taste, said method comprising utilizing a compound of Formula XIII

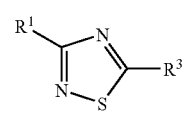

XIII wherein $R^1$ is an optionally substituted phenyl, preferably optionally substituted by one or more substituents independently selected from the group consisting of $C_{1-6}$ alkyl, $C_{1-6}$ alkyloxy, halogen, hydroxyl and nitro;

$R^3$ is Het—C(O)—NH—$R^{31}$;

Het is a 5- to 7-membered nitrogen-containing heterocycle; and $R^{31}$ is an optionally substituted phenyl, preferably optionally substituted by one or more substituents independently selected from the group consisting of $C_{1-6}$ alkyl, $C_{1-6}$ alkyloxy, halogen, and $NO_2$.

In one embodiment of this fourth subclass, $R^1$ is unsubstituted phenyl.

The Het group can be any 5- to 7-membered nitrogen-containing heterocycle, including heteroaryl groups. The Het group, in certain embodiments, contains 1 to 4, preferably 1 or 2 nitrogen atoms in the ring. Suitable Het groups include, but are not necessarily limited to, piperidine, piperizine, pyrrolidine, azepine, and morpholine.

By way of example, a suitable group of compounds for use within this fourth subclass is a compound of Formula XIII

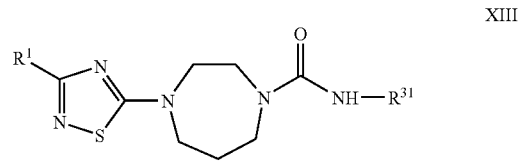

XIII wherein $R^1$ is phenyl optionally substituted, for example, by one or more of $C_{1-6}$ alkyl, $C_{1-6}$ alkyloxy, halogen, and/or $NO_2$, preferably $R^1$ is phenyl; and $R^{31}$ is phenyl optionally substituted, for example, by one or more of $C_{1-6}$ alkyl, $C_{1-6}$ alkyloxy, halogen, hydroxyl and/or $NO_2$, preferably $R^{31}$ is unsubstituted phenyl.

In a fifth subclass, the present invention is directed to a method of enhancing a sweet taste, said method comprising utilizing a compound of Formula XIV:

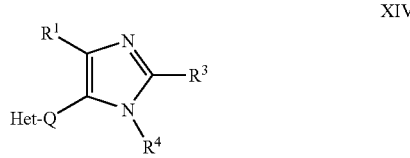

XIV wherein $R^1$ is H, $C_{1-6}$ alkyl, halogen, or $NO_2$;

$R^3$ and $R^4$ are independently H or $C_{1-6}$ alkyl;

Q is S, N, or O, preferably S; and

Het is a 5- to 6-membered heteroaryl, preferably a nitrogen-containing heteroaryl, optionally substituted with one or more substituents selected from the group consisting of nitro and halogen.

Suitable Het groups include pyridinyl, pyrrolyl, and pyrimindyl. For example, Het can be a pyridyl group and, in particular, wherein the pyridyl group is attached to Q at the 2-position. In one embodiment, the Het group is substituted with a halogen, preferably chlorine. In one embodiment, n is 1. In another embodiment, Het is a 5-chloropyridyl group attached to Q at the 2-position. In another embodiment, $R^1$ is nitro. In another embodiment, $R^3$ is alkyl, preferably methyl. In another embodiment, $R^4$ is alkyl, preferably ethyl.

In a sixth subclass, the present invention is directed to a method of enhancing a sweet taste, said method comprising utilizing a compound of Formula XV:

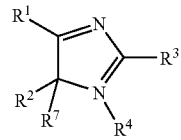

XV wherein $R^1$ and $R^3$ are independently optionally substituted phenyl, preferably optionally substituted by one or more of $C_{1-6}$ alkyl, $C_{1-6}$ alkoxy, halogen, hydroxyl, or nitro;

$R^4$ is absent, O, or $C_{1-6}$ alkyl; and $R^2$ and $R^7$ are independently $C_{1-6}$ alkyl.

In a further embodiment within the sixth subclass, the present invention is directed to a method of enhancing a sweet taste, said method comprising utilizing a compound of Formula XVI:

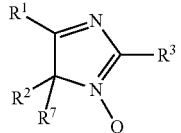

XVI wherein $R^1$ and $R^3$ are independently optionally substituted phenyl, preferably optionally substituted by one or more of $C_{1-6}$ alkyl, $C_{1-6}$ alkoxy, halogen, hydroxyl, or nitro; and $R^2$ and $R^7$ are independently is H or $C_{1-6}$ alkyl.

In a further embodiment within the sixth subclass, the present invention is directed to a method of enhancing a sweet taste, said method comprising utilizing a compound of Formula XVI wherein: $R^1$ and $R^3$ are phenyl; and $R^2$ and $R^7$ are independently H or $C_{1-6}$ alkyl.

In a seventh subclass, the present invention is directed to a method of enhancing a sweet taste, said method comprising utilizing a compound of Formula XVII:

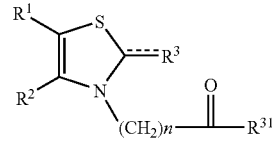

XVII wherein $R^1$ is H or $C_{1-6}$ alkyl;

$R^2$ is H;

$R^3$ is $C_{1-6}$ alkyl, H, oxo, or =NH;

$R^{31}$ is optionally substituted phenyl, preferably optionally substituted by one or more of $C_{1-6}$ alkyl, $C_{1-6}$ alkoxy, halogen, hydroxyl, and nitro; and n is 0 to 3.

In one embodiment, $R^{31}$ is a phenyl substituted by a nitro group, preferably $R^{31}$ is 3-nitrophenyl. The bond between $R^3$ and the ring can be either a single or double bond, as indicated by the dashed line. In certain embodiments, the bond must be double bond, e.g., when $R^3$ is =NH. In other instances, the bond must be a single bond, e.g., when $R^3$ is H.

In a further embodiment within this seventh subclass, the present invention is directed to a method of enhancing a sweet taste, said method comprising utilizing a compound of Formula XVI:

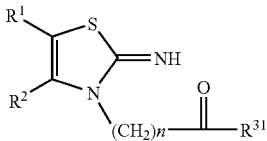

XVI wherein $R^1$ is H or $C_{1-6}$ alkyl; $R^2$ is H; $R^{31}$ is optionally substituted phenyl, preferably optionally substituted by one or more of $C_{1-6}$ alkyl, $C_{1-6}$ alkoxy, halogen, hydroxyl, or nitro; and n is 0 to 3. In one example within this embodiment, $R^1$ is hydrogen. In another, n is 1. In another, $R^{31}$ is phenyl substituted by a nitro group, and preferably $R^{31}$ is 3-nitrophenyl.

In an eighth subclass, the present invention is directed to a method of enhancing a sweet taste, said method comprising utilizing a compound of Formula XVIII:

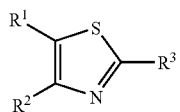

XVIII wherein $R^1$ is H or $C_{1-6}$ alkyl;

$R^2$ is H, $C_{1-6}$ alkyl, or optionally substituted phenyl, preferably optionally substituted by one or more substituents independently selected from the group consisting of $C_{1-6}$ alkyl, $C_{1-6}$ alkoxy, halogen, hydroxyl, and nitro; and $R^3$ is NH—C(=O)—(CH$_2$)$_n$—$R^a$, wherein, n is 0 to 3 and $R^a$ is selected from (a) optionally substituted phenyl, preferably optionally substituted by one or more substituents independently selected from the group consisting of $C_{1-6}$ alkyl, $C_{1-6}$ alkoxy, halogen, hydroxyl, and nitro, and (b) $NR^{31}R^{32}$, wherein $R^{31}$ and $R^{32}$ are independently selected from H or $C_{1-6}$ alkyl and n is 0 to 3, or $R^3$ is

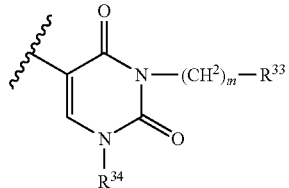

wherein $R^{33}$ is optionally substituted phenyl, preferably optionally substituted by one or more of $C_{1-6}$ alkyl, $C_{1-6}$ alkoxy, halogen, hydroxyl, or nitro; $R^{34}$ is H or $C_{1-6}$ alkyl; and m is 0 to 3.

In one embodiment within this eighth subclass, $R^2$ is phenyl substituted by a halogen, preferably chlorine. In another embodiment, $R^2$ is 4-chlorophenyl. In another, $R^2$ is $C_{1-6}$ alkyl, preferably methyl.

In a further embodiment within the eighth subclass, the present invention is directed to a method of enhancing a sweet taste, said method comprising utilizing a compound of Formula XIX:

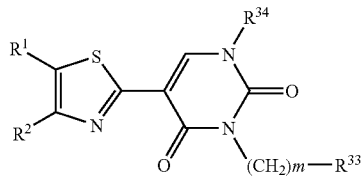

XIX wherein $R^1$ is H or $C_{1-6}$ alkyl;

$R^2$ is H or $C_{1-6}$ alkyl;

$R^{33}$ is optionally substituted phenyl, preferably optionally substituted by one or more of $C_{1-6}$ alkyl, $C_{1-6}$ alkoxy, halogen, hydroxyl, or nitro;

$R^{34}$ is H or $C_{1-6}$ alkyl; and m is 0 to 3.

In one embodiment within this eighth subclass, $R^1$ is hydrogen. In another embodiment, $R^2$ is $C_{1-6}$ alkyl, preferably methyl. In another, $R^{34}$ is an isopropyl group. In another, $R^{33}$ is phenyl.

In a further embodiment within the eighth subclass, the present invention is directed to a method of enhancing a sweet taste, said method comprising utilizing a compound of Formula XIX wherein:

$R^1$ is H or $C_{1-6}$ alkyl;

$R^2$ is H or $C_{1-6}$ alkyl;

$R^{33}$ is optionally substituted phenyl, preferably optionally substituted by one or more of $C_{1-6}$ alkyl, $C_{1-6}$ alkoxy, halogen, hydroxyl, or nitro;

$R^{34}$ is H or $C_{1-6}$ alkyl; and m is 1.

In one example within this embodiment, $R^1$ is hydrogen. In another example, $R^2$ is $C_{1-6}$ alkyl, preferably methyl. In one, $R^{34}$ is an isopropyl group. In another, $R^{33}$ is phenyl.

In further embodiment within the eighth subclass, the present invention is directed to a method of enhancing a sweet taste, said method comprising utilizing a compound of Formula XX:

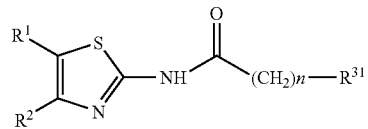

XX wherein:

$R^1$ is H, $C_{1-6}$ alkyl, or optionally substituted phenyl, preferably optionally substituted by one or more substituents independently selected from the group consisting of $C_{1-6}$ alkyl, $C_{1-6}$ alkoxy, halogen, hydroxyl, and nitro;

$R^2$ is H, $C_{1-6}$ alkyl, or optionally substituted phenyl, preferably optionally substituted by one or more substituents independently selected from the group consisting of $C_{1-6}$ alkyl, $C_{1-6}$ alkoxy, halogen, hydroxyl, and nitro;

$R^{31}$ is either an optionally substituted phenyl, preferably optionally substituted by one or more substituents independently selected from the group consisting of $C_{1-6}$ alkyl, $C_{1-6}$ alkoxy, halogen, hydroxyl, and nitro, or is $NR^{5a}R^{6a}$, wherein $R^{5a}$ and $R^{6a}$ are independently selected from H or $C_{1-6}$ alkyl; and n is 0 to 3.

In further embodiment within the eighth subclass, the present invention is directed to a method of enhancing a sweet taste, said method comprising utilizing a compound of Formula XX wherein $R^1$ is hydrogen or $C_{1-6}$ alkyl; $R^2$ is an optionally substituted phenyl, preferably optionally substituted by one or more of $C_{1-6}$ alkyl, $C_{1-6}$ alkoxy, halogen, hydroxyl, or nitro; $R^{31}$ is $NR^{5a}R^{6a}$; and n is 0 to 3. In a further embodiment, $R^2$ is substituted by a halogen, preferably chlorine. In another embodiment, $R^2$ is 3-chlorophenyl. In another embodiment, $R^1$ is hydrogen. In another embodiment, $R^{5a}$ and $R^a$ are both alkyl groups, preferably methyl.

In further embodiment within the eighth subclass, the present invention is directed to a method of enhancing a sweet taste, said method comprising utilizing a compound of Formula XX wherein $R^1$ is hydrogen or $C_{1-6}$ alkyl; $R^2$ is H, $C_{1-6}$ alkyl, optionally substituted phenyl, preferably optionally substituted by one or more of $C_{1-6}$ alkyl, $C_{1-6}$ alkoxy, halogen, hydroxyl, or nitro; n is 0 to 3; $R^{31}$ is optionally substituted phenyl, preferably optionally substituted by one or more of $C_{1-6}$ alkyl, $C_{1-6}$ alkoxy, halogen, hydroxyl, or nitro; and n is 0 to 3. In one embodiment, $R^2$ is an optionally substituted phenyl, preferably $R^2$ is substituted by one or more alkyl groups. In a further embodiment, $R^2$ is a ethyl-substituted phenyl, preferably 3-ethylphenyl. In one embodiment, $R^{31}$ is substituted by one or more methyl groups, preferably $R^{31}$ is 3,5-dimethyoxyphenyl. In one embodiment, n is zero.

In a ninth subclass, the present invention is directed to a method of enhancing a sweet taste, said method comprising utilizing a compound of Formula XXI:

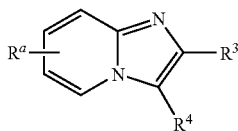

XXI wherein $R^3$ is optionally substituted phenyl, preferably optionally substituted by one or more substituents independently selected from the group consisting of $C_{1-6}$ alkyl, $C_{1-6}$ alkoxy, halogen, hydroxyl, and nitro; $R^4$ is H; and $R^a$ is H or $C_{1-6}$ alkyl. In an embodiment of this ninth subclass, the present invention is directed to a method of enhancing a sweet taste, said method comprising utilizing a compound of Formula XXI wherein $R^a$ is H or $C_{1-6}$ alkyl; and $R^3$ is a disubstituted phenyl containing $C_{1-6}$ alkyl, halogen, or $NO_2$, or preferably is a disubstituted phenyl containing a $C_{1-6}$ alkoxy substituent and a halogen substituent.

In a further embodiment of the ninth subclass, the present invention is directed to a method of enhancing a sweet taste, said method comprising utilizing a compound of Formula XXI wherein $R^a$ is H or $C_{1-6}$ alkyl; and $R^3$ optionally substituted phenyl, preferably optionally substituted by one or more of $C_{1-6}$ alkyl, $C_{1-6}$ alkoxy, halogen, hydroxyl, or nitro. In one embodiment, $R^3$ is a phenyl substituted with a halogen and a $C_{1-6}$ alkyloxy group, preferably $R^3$ is 2-methoxy-3-chlorophenyl.

In a tenth subclass, the present invention is directed to a method of enhancing a sweet taste, said method comprising utilizing a compound of Formula XXII wherein:

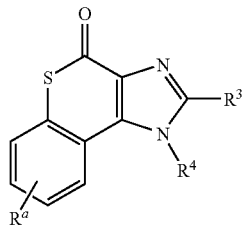

XXII wherein $R^3$ is H or $C_{1-6}$ alkyl; $R^a$ is H or $C_{1-6}$ alkyl; and $R^4$ is optionally substituted phenyl, preferably optionally substituted by one or more substituents independently selected from the group consisting of $C_{1-6}$ alkyl, halogen, and nitro. In an embodiment of this tenth subclass, the present invention is directed to a method of enhancing a sweet taste, said method comprising utilizing a compound of Formula XXII wherein $R^3$ is H or $C_{1-6}$ alkyl; $R^4$ is phenyl; and $R^a$ is H or $C_{1-6}$ alkyl.

In a eleventh subclass, the present invention is directed to a method of enhancing a sweet taste, said method comprising utilizing a compound of Formula XXIII:

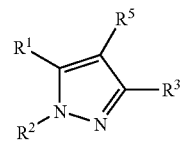

XXIII wherein $R^1$ is H, $C_{1-6}$ alkyl, or halogen;

$R^2$ is H or $C_{1-6}$ alkyl;

$R^3$ is H, halogen, $C_{1-6}$ haloalkyl, preferably trifluoromethyl, or $C_{1-6}$ alkyl;

$R^5$ is phenylamide (i.e., C(O)NH-Ph) optionally substituted with one or more substituents selected from the group consisting of H, halogen, $C_{1-6}$ haloalkyl, preferably trifluoromethyl, nitro, $C_{1-6}$ alkyl, and $C_{1-6}$ alkyloxy.

In one embodiment within this eleventh subclass, the invention comprises the use of a compound of the following formula:

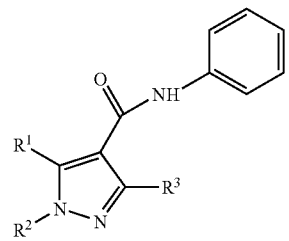

wherein $R^1$, $R^2$, and $R^3$ are defined as above. In another embodiment of this eleventh subclass, the present invention is directed to a method of enhancing a sweet taste, said method comprising utilizing a compound of Formula XXIII wherein $R^1$ is halogen; $R^2$ is H or $C_{1-6}$ alkyl; $R^3$ is $C_{1-6}$ haloalkyl, preferably $CF_3$; and the phenylamide group is substituted with one or two groups independently selected from the group consisting of halogen, $C_{1-6}$ haloalkyl, $NO_2$, $C_{1-6}$ alkyl, and $C_{1-6}$ alkyloxy.

In certain embodiments of this eleventh subclass, $R^1$ is halogen and $R^3$ is $CF_3$.

Examples of suitable compounds for use in the method of the present invention include: ethyl 2-(3-methylbenzo[d]thiazol-2(3H)-ylideneamino)acetate;
2-(2-(2-methoxyphenoxy)ethylthio)-1H-benzo[d]imidazole;
methyl 3-(5-nitropyridin-2-yloxy)thiophene-2-carboxylate;
6-(4-chloro-3-nitrophenyl)-3-ethyl-5H-[1,2,4]triazolo[4,3-b][1,2,4]triazole;
6-p-tolylimidazo[2,1-b][1,3,4]thiadiazole;
N-phenyl-4-(3-phenyl-1,2,4-thiadiazol-5-yl)-1,4-diazepane-1-carboxamide;
2-(2-(2-(2,6-dimethoxyphenoxy)ethylthio)-1H-benzimidazol-1-yl)ethanol;
1-ethyl-2-methyl-4-nitro-5-(5-chloropyridin-2-ylthio)imidazole;
2,4-diphenyl-5,5-dimethylimidazole-1-oxide;
1-allyl-3-(3-methylbenzo[d]thiazol-2-(3H)-ylidene)thiourea;
2-(2-iminothiazol-3(2H)-yl)-1-(3-nitrophenyl)ethanone;
3-benzyl-1-isopropyl-5-(4-methylthiazol-2-yl)pyrimidine-2,4(1H,3H)-dione;
2-(3-chloro-2-methoxyphenyl)imidazo[1,2-a]pyridine;
N-(4-(4-ethylphenyl)thiazol-2-yl)-3,5-dimethoxybenzamide;
1-phenylthiochromeno[4,3-d]imidazol-4(1H)-one;
N-(4-(4-chlorophenyl)thiazol-2-yl)-2-(dimethylamino)acetamide;
5-chloro-1-methyl-3-(trifluoromethyl)-N-(4-(trifluoromethyl)phenyl)-1H-pyrazole-4-carboxamide; and physiologically acceptable salts thereof.

Further examples of suitable compounds for use in the method of the present invention include: N-(4-(((2,6-dimethoxypyrimidin-4-yl)amino)sulfonyl)phenyl)-4-nitrobenzamide;
4-phenyl-2-(pyrrolidin-1-ylmethyl)phthalazin-1(2H)-one;
5-(perfluorophenoxy)isophthalic acid;
2-(dibenzylamino)acetic acid;
ethyl 2-cyano-2-(phenyldiazenyl)acetate; and
physiologically acceptable salts thereof.

The methods of the present invention also include the use of a physiologically acceptable salt of a compound according to Formula I. The term physiologically acceptable salt refers to an acid- and/or base-addition salt of a compound according to Formula I. Acid-addition salts can be formed by adding an appropriate acid to the compound according to Formula I. Base-addition salts can be formed by adding an appropriate base to the compound according to Formula I. Said acid or base does not substantially degrade, decompose, or destroy said compound according to Formula I. Examples of suitable physiologically acceptable salts include hydrochloride, hydrobromide, acetate, furmate, maleate, oxalate, and succinate salts. Other suitable salts include sodium, potassium, carbonate, and tromethamine salts.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of Formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of the present invention can have asymmetric centers at certain of the nitrogen or sulfur atoms. Consequently, these isomers or mixtures thereof are part of the present invention.

The compounds of the present invention may also display other instances of chirality, such as atropoisomerism. Thus, these isomers or mixtures thereof are part of the invention. It is further understood that the present invention encompasses the use of tautomers of a compound of Formula I. Tautomers are well-known in the art and include keto-enol tautomers.

The compounds of the present invention may also contain varying amounts of isotopes of carbon, hydrogen, nitrogen, oxygen, sulfur, halogen, etc.; such as $^{13}C$, $^{14}C$, deuterium, tritium, $^{15}N$, $^{18}O$, $^{128}I$, etc. Some of the isotopic content is naturally occurring, but the compounds of the present invention may be enriched or depleted in one or more of these. Thus, these isotopes or mixtures thereof are part of the invention.

The compounds of Formula I may also be solvated, including hydrated. Hydration may occur during manufacturing of the compounds or compositions comprising the compounds, or the hydration may occur over time due to the hygroscopic nature of the compounds.

Certain compounds within the scope of Formula I may be derivatives referred to as "prodrugs." The expression "prodrug" denotes a derivative of a known direct acting agent, wherein the derivative has therapeutic value that may be similar to, greater than, or less than that of the agent. Generally, the prodrug is transformed into the active agent by an enzymatic or chemical process when delivered to the subject, cell, or test media. In certain instances, prodrugs are derivatives of the compounds of the invention which have metabolically cleavable groups and become by solvolysis or under physiological conditions the compounds of the invention which are pharmaceutically active in vivo. For example, ester derivatives of compounds of this invention are often active in vivo, but not in vitro. Other derivatives of the compounds of this invention have activity in both their acid and acid derivative forms, but the acid derivative form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine. Simple aliphatic or aromatic esters derived from acidic groups pendent on the compounds of this invention are preferred prodrugs.

When any variable occurs more than one time in any constituent or in Formula I, its definition on each occurrence is independent of its definition at every other occurrence, unless otherwise indicated. Also, combinations of substituents and/or variables are permissible only if such combinations result in stable compounds.

The term "alkyl," as used herein by itself or as part of another group, refers to both straight and branched chain radicals of up to 10 carbons, unless the chain length is limited thereto, such as methyl, ethyl, propyl, isopropyl, butyl, 1-methylpropyl, 2-methylpropyl, pentyl, 1-methylbutyl, isobutyl, pentyl, t-amyl ($CH_3CH_2(CH_3)_2C$—), hexyl, isohexyl, heptyl, octyl, or decyl.

The term "alkenyl," as used herein by itself or as part of another group, refers to a straight or branched chain radical of 2-10 carbon atoms, unless the chain length is limited thereto, including, but not limited to, ethenyl, 1-propenyl, 2-propenyl, 2-methyl-1-propenyl, 1-butenyl, 2-butenyl, 3-butenyl, pentenyl, 1-hexenyl, and 2-hexenyl.

The term "alkylene," as used herein by itself or as a part of another group, refers to a diradical of an unbranched saturated hydrocarbon chain, having, unless otherwise indicated, from 1 to 15 carbon atoms, preferably 1 to 10 carbon atoms and more preferably 1 to 6 carbon atoms. This term is exemplified by groups such as methylene (—$CH_2$—), ethylene (—$CH_2CH_2$—), propylene (—$CH_2CH_2CH_2$—), butylene, and the like.

The term "alkenylene," as used herein by itself or part of another group, refers to a diradical of an unbranched, unsaturated hydrocarbon chain, having, unless otherwise indicated, from 2 to 15 carbon atoms, preferably 1 to 10 carbon atoms, more preferably 1 to 6 carbon atoms, and having at least 1 and preferably from 1 to 6 sites of vinyl unsaturation. This term is exemplified by groups such as ethenylene (—CH═CH—), propenylene (—$CH_2$CH═CH—, —CH═CH$CH_2$—), and the like.

The term "alkoxy," as used herein by itself or as part of another group, refers to any of the above alkyl groups linked to an oxygen atom. Typical examples are methoxy, ethoxy, isopropyloxy, sec-butyloxy, and t-butyloxy.

The term "alkenyloxy," as used herein by itself or as part of another group, refers to any of the above alkenyl groups linked to an oxygen atom. Typical examples include ethenyloxy, propenyloxy, butenyloxy, pentenyloxy, and hexenyloxy.

The term "aryl," as used herein by itself or as part of another group, refers to monocyclic or bicyclic aromatic groups containing from 6 to 14 carbons in the ring portion, preferably 6-10 carbons in the ring portion. Typical examples include phenyl, naphthyl, anthracenyl, or fluorenyl.

The term "heteroaryl," as used herein by itself or as part of another group, refers to groups having 5 to 14 ring atoms; 6, 10, or 14 π electrons shared in a cyclic array; and containing carbon atoms and 1, 2, 3, or 4 oxygen, nitrogen, or sulfur atoms. Examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathinyl, 2H-pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups. Further heteroaryls are described in A. R. Katritzky and C. W. Rees, eds., *Comprehensive Heterocyclic Chemistry: The Structure, Reactions, Synthesis and Use of Heterocyclic Compounds*, Vol. 1-8, Pergamon Press, NY (1984).

The term "halogen" or "halo," as used herein by itself or as part of another group, refers to chlorine, bromine, fluorine or iodine.

The term "monoalkylamine" or "monoalkylamino," as used herein by itself or as part of another group, refers to the group $NH_2$ wherein one hydrogen has been replaced by an alkyl group, as defined above.

The term "dialkylamine" or "dialkylamino," as used herein by itself or as part of another group refers to the group, $NH_2$ wherein both hydrogens have been replaced by alkyl groups, as defined above.

The term "hydroxyalkyl," as used herein by itself or as part of another group, refers to any of the above alkyl groups wherein one or more hydrogens thereof are substituted by one or more hydroxyl moieties.

The term "haloalkyl," as used herein by itself or as part of another group, refers to any of the above alkyl groups wherein one or more hydrogens thereof are substituted by one or more halo moieties. Typical examples include fluoromethyl, trifluoromethyl, trichloroethyl, and trifluoroethyl.

The term "carboxyalkyl," as used herein by itself or as part of another group, refers to any of the above alkyl groups wherein one or more hydrogens thereof are substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or alkyl, or together with the nitrogen to which they are bound, form a saturated or unsaturated 5-, 6-, or 7-membered ring.

The term "oxy" means an oxygen (O) atom.

The term "thio" means a sulfur (S) atom.

As used herein, unless otherwise indicated, Cy represents a cyclo group fused to another ring in the chemical structure of which the Cy is a part. Suitable cyclo groups include cycloalkyl, cycloheteroalkyl, aryl, and heteroaryl. The cyclo group can be a monocyclic group or polycyclic group, such as a bicyclic group. Thus, if the Cy group is a bicyclic ring system, the entire molecule will comprise a tricyclic ring system including the core ring show in Formula I. The cyclo group may contain 5-10 carbon atoms and/or heteroatoms as part of its ring, excluding the shared ring atoms of the other ring system. Suitable cyclo groups include any aryl and heteroaryl rings described herein.

For instance, in the following structure,

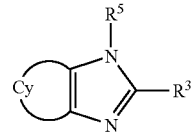

Cy represents a cyclo group fused to the five-membered nitrogen-containing heterocycle. Thus, the above structure covers, among other possibilities, a benzimidazole compound. Further, and by way of example, a Cy containing 5-10, preferably 5-7, carbon atoms and/or heteroatoms in the above structure would indicate that the Cy group contains 5-10, preferably 5-7, carbon atoms and/or heteroatoms including the 2 carbon atoms shared between the cyclo ring and the imidazole ring.

Generally and unless defined otherwise, the phrase 'optionally substituted' used herein refers to a group or groups being optionally substituted with one or more substituents independently selected from the group consisting of: halogen, nitro, cyano, $OR_{22}$, alkyl which may be substituted with one or more occurrences of $R_{23}$, alkenyl which may be substituted with one or more occurrences of $R_{23}$, alkynyl which may be substituted with one or more occurrences of $R_{23}$, cycloalkyl which may be substituted with one or more occurrences of $R_{23}$, aryl which may be substituted with one or more occurrences of $R_{23}$, heterocyclo which may be substituted with one or more occurrences of $R_{23}$, $SR_{22}$, $SO_2R_{22}$, $COOR_{22}$, $C(O)R_{22}$, $CONR_{24}R_{25}$, $SO_2NR_{24}R_{25}$, $SO_2N(H)C(O)R_{22}$, $SO_2N(H)CO_2R_{22}$ wherein $R_{22}$ is not H, $NR_{24}R_{25}$, $N(R_{24})SO_2R_{25}$, $N(R_{24})C(O)_mR_{25}$ (wherein m is 1 or 2), $N(R_{24})C(O)NR_{25}R_{26}$, $N(R_{24})SO_2NR_{25}R_{26}$, $OC(O)R_{22}$, $OC(O)OR_{22}$, $OC(O)NR_{25}R_{26}$, $C(O)N(H)SO_2NR_{25}R_{26}$, $C(O)N(H)SO_2R_{25}$, oxo (or keto, i.e., ═O), thioxo (i.e., ═S), imino (i.e., ═$NR_{27}$), $NR_{27}$—C(═$NR_{28}$)$R_{29}$, $NR_{27}$—C(═$NR_{28}$)$NR_{29}R_{30}$, C(═$NR_{27}$)$NR_{28}R_{29}$, OC(═$NR_{27}$)$NR_{28}R_{29}$, OC(═$NR_{27}$)$R_{28}$, C(═$NR_{27}$)$R_{28}$, and C(═$NR_{27}$)$OR_{22}$; wherein $R_{22}$ is selected from H, $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo each of which may be substituted with 1 to 3 independent occurrences of $R_{23}$; wherein $R_{24}$, $R_{25}$, and $R_{26}$ are selected from $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo each of which may be substituted with 1 to 3 independent occurrences of $R_{23}$; or $R_{24}$ and $R_{25}$, or $R_{24}$ and $R_{26}$, or $R_{25}$ and $R_{26}$ may be joined by an alkylene or an alkenylene chain to form a 5- to 8-membered heterocyclo ring which is defined as for heterocyclo wherein the substituents may be one or more occurrences of $R_{23}$; wherein $R_{27}$, $R_{28}$, $R_{29}$, and $R_{30}$ are independently selected from the group consisting of H, nitro, cyano, OH, O($C_1$-$C_6$ alkyl), C(O)$R_{22}$, C(O)N$R_{24}R_{25}$, $CO_2R_{22}$ (with the proviso that $R_{22}$ is not H), $SO_2R_{22}$, $SO_2NR_{24}R_{25}$, $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, and $C_1$-$C_9$ heterocyclo; or $R_{27}$ and $R_{28}$, or $R_{27}$ and $R_{29}$, or $R_{27}$ and $R_{30}$, or $R_{28}$ and $R_{29}$, or $R_{28}$ and $R_{30}$, or $R_{29}$ and $R_{30}$ are joined by an alkylene or alkenylene chain to form a 5-8 membered ring that may be optionally substituted with one or more occurrences of $R_{23}$; wherein each occurrence of $R_{23}$ is independently selected from the group consisting of halogen, nitro, cyano, $OR_{31}$, alkyl optionally substituted with halogen, cycloalkyl optionally substituted with halogen, aryl optionally substituted with halogen, hydroxy, nitro, methoxy, trifluoromethyl, cyano, carbomethoxy, $CONH_2$, or CHO, heterocyclo optionally substituted with halogen, hydroxy, nitro, methoxy, trifluoromethyl, cyano, carbomethoxy, $CONH_2$, or CHO, $SR_{31}$, $CO_2R_{31}$, C(O)$R_{31}$, $CONR_{32}R_{33}$, $SO_2NR_{32}R_{33}$, $NR_{32}R_{33}$, $N(R_{32})SO_2R_{33}$, $N(R_{32})C(O)_mR_{33}$ (m is 1 or 2), $N(R_{32})C(O)NR_{33}R_{34}$, $N(R_{32})SO_2NR_{33}R_{34}$, OC(O)$R_{31}$, OC(O)O$R_{31}$, $SO_2R_{31}$, $SO_2N(H)C(O)R_{31}$, $SO_2N(H)CO_2R_{31}$ wherein $R_{31}$ is not H, C(O)N(H)$SO_2NR_{32}R_{33}$, C(O)N(H)$SO_2R_{31}$, OC(O)$NR_{32}R_{33}$, $NR_{35}$—C(=$NR_{36}$)$R_{37}$, $NR_{35}$—C(=$NR_{36}$)$OR_{31}$, $NR_{35}$—C(=$NR_{36}$)$NR_{37}R_{38}$, C(=$NR_{35}$)$NR_{36}R_{37}$, OC(=$NR_{35}$)$R_{36}$, OC(=$NR_{35}$)$NR_{36}R_{37}$, and C(=$NR_{35}$)$OR_{31}$, $R_{31}$ is selected from unsubstituted alkyl, alkenyl, unsubstituted alkynyl, unsubstituted cycloalkyl, unsubstituted aryl, and unsubstituted heterocyclo; wherein each occurrence of $R_{32}$, $R_{33}$ and $R_{34}$ is independently selected from the group consisting of unsubstituted alkyl, unsubstituted alkenyl, unsubstituted alkynyl, unsubstituted cycloalkyl, unsubstituted aryl, unsubstituted heterocyclo; or $R_{32}$ and $R_{33}$, or $R_{32}$ and $R_{34}$, or $R_{33}$ and $R_{34}$, are joined by an unsubstituted alkylene or unsubstituted alkenylene chain to form a 5-8 membered unsubstituted heterocyclo ring; and wherein $R_{35}$, $R_{36}$, $R_{37}$, are $R_{38}$ independently selected from the group consisting of nitro, cyano, unsubstituted alkyl, unsubstituted alkenyl, unsubstituted alkynyl, unsubstituted cycloalkyl, unsubstituted aryl, unsubstituted heterocyclo; or $R_{35}$ and $R_{36}$, or $R_{35}$ and $R_{37}$, or $R_{35}$ and $R_{38}$, or $R_{36}$ and $R_{37}$, or $R_{36}$ and $R_{38}$, or $R_{37}$ and $R_{38}$ is joined by an unsubstituted alkylene chain or unsubstituted alkenylene chain to form a 5- to 8-membered unsubstituted heterocyclo ring.

Where alkyl groups as defined above have single bonds for attachment to other groups at two different carbon atoms, they are termed "alkylene" groups and may optionally be substituted as defined above for "alkyl." Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

In a subgroup of the invention, the phrase "optionally substituted" refers to a group or groups being optionally substituted with one or more substituents independently selected from the group consisting of amino, hydroxyl, nitro, halogen, cyano, thiol, $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloheteralkyl, $C_{3-6}$ cycloheteroalkenyl, $C_{6-10}$ aryl, 5-10 membered heteroaryl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{6-10}$ aryl($C_{1-6}$)alkyl, $C_{6-10}$ aryl($C_{2-6}$)alkenyl, $C_{6-10}$ aryl($C_{1-6}$)alkoxy, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono($C_{1-4}$)alkylamino ($C_{2-6}$)alkoxy, di($C_{1-4}$)alkylamino($C_{2-6}$)alkoxy $C_{2-10}$ mono (carboxyalkyl)amino, bis($C_{2-10}$ carboxyalkyl)amino, aminocarbonyl, $C_{6-14}$ aryl($C_{1-6}$)alkoxycarbonyl, $C_{2-6}$ alkynylcarbonyl, $C_{1-6}$ alkylsulfonyl, $C_{2-6}$ alkynylsulfonyl, $C_{6-10}$ arylsulfonyl, $C_{6-10}$ aryl($C_{1-6}$)alkylsulfonyl, $C_{1-6}$ alkylsulfinyl, $C_{1-6}$ alkylsulfonamido, $C_{6-10}$ arylsulfonamido, $C_{6-10}$ aryl($C_{1-6}$) alkylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino.

A "tastant" is any substance capable of eliciting gustatory excitation, i.e., stimulation the sense of taste. When a subject ingests a tastant, and that tastant encounters a taste receptor cell in the appropriate concentration, an action potential is produced which, via synapses with primary sensory neurons, communicates the signal registered by the receptor, via afferent nerves, to the appropriate region of the sensory cortex of the brain, resulting in the perception of a particular taste by the subject. Examples of sweet tastants include, but are not limited to, sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®.

The phrase "a sweet tastant" as used herein means "one or more sweet tastants." Thus, the methods of this invention may comprise administering one sweet tastant or multiple sweet tastants and the compositions of this invention may comprise one sweet tastant or multiple sweet tastants. For example, the food products of this invention can comprise both sucrose and corn syrup as sweet tastants, or sucrose and aspartame as sweet tastants, or saccharin and sucralose as sweet tastants. In some cases a sweet tastant(s) may be present at a suboptimal amount where its sweetness is enhanced or intensified by use of this invention.

Although detailed definitions have not been provided for every term used above, each term is understood by one of ordinary skill in the art.

As explained above, the present invention provides methods, compounds, and compositions that are useful, for example, for enhancing sweet tastes. The methods of the present invention enable one to use a known sweetening agents, or sweet tastants, in a reduced amount combined with a compound according to Formula I, or any of the specific subgroups or specific compounds described herein, in order to achieve the same level of sweetness when the known sweet tastant is used alone in the traditional amount. By way of brief example, a common carbonated cola beverage may contain about 20 to 30 grams of sugar (e.g., fructose) and about 100 calories per 8 ounce serving. The present invention enables one to prepare a similar cola beverage with substantially reduced sugar and caloric content but with the same level of sweetness. The compounds identified in here, e.g., according to Formula I, enhance the sweet taste produced by the reduce sugar content, thereby creating an enhanced sweet taste based on the reduced level of sweet tastant, e.g., table sugar.

As mentioned above, the above described compounds may be used to enhance a sweet taste. Such enhancement may be in vitro or in vivo. The amount of the compound of Formula I, or any of the specific subgroups, subclasses, or specific compounds described above, used to enhance the sweet taste may not necessarily be the same when used in vivo compared to in vitro. Factors such as pharmacokinetics and pharmacodynamics of the particular compound may require that a larger or smaller amount of the compound of Formula I, or any of the specific subgroups, subclasses, or specific compounds described above, be used when enhancing a taste modulating protein in vivo. Accordingly, one aspect of the present invention is a method of enhancing a sweet taste by utilizing a compound according to Formula I, or any of the specific subgroups, subclasses, or specific compounds described above.

The compounds of the present invention can be used to enhance the sweet taste of a food product exhibiting a sweet taste comprising administering to a subject a food product comprising a sweet tastant and one or more compounds according to Formula I, or any of the specific subgroups, subclasses, or specific compounds described above. Furthermore, in a preferred embodiment, the food product comprises a compound of Formula I, or any of the specific subgroups, subclasses, or specific compounds described above in an amount sufficient to enhance the sweet taste.

The compounds of this invention may be used to enhance the desirable properties of sweetness in any food product. The phrase "food product" as used herein includes but is not limited to fruits, vegetables, juices, meat products such as ham, bacon and sausage; egg products, fruit concentrates, gelatins and gelatin-like products such as jams, jellies, preserves, and the like; milk products such as ice cream, sour cream and sherbet; icings, syrups including molasses; corn, wheat, rye, soybean, oat, rice and barley products, nut meats and nut products, cakes, cookies, confectionaries such as candies, gums, fruit flavored drops, and chocolates, chewing gum, mints, creams, icing, ice cream, pies and breads, beverages such as coffee, tea, carbonated soft drinks, such as COKE® and PEPSI®, non-carbonated soft drinks, juices and other fruit drinks, sports drinks such as GATORADE®, coffee, teas, iced teas, coca, alcoholic beverages, such as beers, wines and liquors, and KOOL-AID.® Preferably, the food products in which the sweetness is enhanced with the compound according to Formula I, or any of the specific subgroups, subclasses, or specific compounds described above, will contain a decreased level of known sweet tastant(s). For example, an improved carbonated soft drink can be produced with the same sweetness as the known carbonated soft drink but with a lower sugar content by adding a compound according to Formula I, or any of the specific subgroups, subclasses, or specific compounds described above. In some cases a sweet tastant(s) may be present at a suboptimal amount where its sweetness is enhanced or intensified by use of this invention.

Food products also include condiments such as herbs, spices and seasonings, flavor enhancers such as monosodium glutamate. A food product also includes prepared packaged products such as dietetic sweeteners, liquid sweeteners, granulated flavor mixes which upon reconstitution with water provide non-carbonated drinks, instant pudding mixes, instant coffee and tea, coffee whiteners, malted milk mixes, pet foods, livestock feed, tobacco and materials for baking applications such as powdered baking mixes for the preparation of breads, cookies, cakes, pancakes, donuts and the like.

Food products also include sugar-free foods or beverages designed for diabetics and others that cannot consume products containing sucrose and diet or low-calorie food and beverages containing little or no sucrose. Especially preferred food products are carbonated beverages containing one or more of the subject enhancers. Other examples of food products envisioned in accordance with the present invention are described below and throughout the specification.

In one embodiment, the present invention is directed to a method of enhancing the sweet taste of a food product comprising a administering to a subject a food product comprising a sweet tastant and one or more compounds according to Formula I, or any of the specific subgroups, subclasses, or specific compounds described above. Furthermore, in a preferred embodiment, the food product comprises a compound of Formula I, or any of the specific subgroups, subclasses, or specific compounds described above in an amount sufficient to enhance the sweet taste. Specific sweet tastants to which one of more compounds of Formula I, or any of the specific subgroups, subclasses, or specific compounds described above, can be added to enhance its sweet taste include but are not necessarily limited to sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®, Specific food products in which an enchanted sweet taste is desired include but are not limited to cakes, cookies, confectioneries such as candies, gums and chocolates, creams, icing, ice cream, pies and breads. Specific food products which are beverages include soft drinks such as COKE®, and PEPSI®, juices and other fruit drinks, sports drinks such as Gatorade®, coffee, teas, iced teas, coca, alcoholic beverages and KOOL-AID®. In one embodiment, the food product comprises one sweet tastant. In another embodiment, the food product comprises more than one sweet tastant. In certain embodiments, the food product comprises sucrose and corn syrup; sucrose and aspartame; or saccharin and sucralose as sweet tastants.

In another embodiment, the present invention is directed to a method of enhancing the sweet taste of a food product selected from fruits, vegetables, juices, meat products such as ham, bacon and sausage; egg products, fruit concentrates, gelatins and gelatin-like products such as jams, jellies, preserves, and the like; milk products such as ice cream, sour cream and sherbet; icings, syrups including molasses; corn, wheat, rye, soybean, oat, rice and barley products, nut meats and nut products, cakes, cookies, confectionaries such as candies, gums, fruit flavored drops, and chocolates, creams, icing, ice cream, pies and breads, comprising administering to a subject a sweet tastant and a compound of Formula I.

In a preferred embodiment, the invention is directed to a method of decreasing the amount of sweet tastant, such as sucrose, frustose, or sucralose, needed in a consumable product, such as a food product or pharmaceutical product, to exhibit a given level of sweetness.

In another embodiment, the present invention is directed to a method of enhancing the sweet taste of a food product comprising administering to a subject a sweetener and one or more compounds according to Formula I. Sweeteners are well known in the art, and include compounds such as sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NutraSweet®. Especially useful are the blends of the compounds of Formula I of this invention and saccharin or physiologically acceptable salts thereof. Examples of saccharin salts include the sodium, potassium, calcium and ammonium salts. In blends with saccharin, the compounds of this invention may reduce or completely mask the recognized undesirable bitter aftertaste of the saccharin.

Any of the food products described herein may comprise one or more sweet tastants. In one embodiment, the food products comprise one sweet tastant. In a further embodiment, the food product comprises more than one sweet tastant. In certain embodiments, the food product comprises sucrose and corn syrup as sweet tastants, or sucrose and aspartame, or saccharin and sucralose.

The compound according to Formula I, or any of the specific subgroups, subclasses, or specific compounds described above, can be typically present in an amount ranging from about 0.00001% to about 50% by weight, preferably about 0.0001% to about 2% by weight, or alternatively, from 0.0001% to about 0.1% by weight. The present invention also contemplates an amount of about 0.0001% to about 1%, preferably about, 0.0005%, 0.001%, 0.002%, 0.005%, 0.01%, 0.05%, 0.1%, 0.3%, 0.8%, 1.5%, by weight, of the food product.

In each of the embodiments of the methods described herein, a compound of Formula I, or any of the specific subgroups, subclasses, or specific compounds described above, may be used in varying ratios to the tastant, i.e. the agent that is believed to cause the sweet taste. For example, a composition of the invention may comprise a compound of Formula I in a molar ratio of about $1:10^6$ to about 10:1, or alternatively administered in a molar ratio of about $1:10^5$, about $1:10^4$, about $10:10^3$, about $1:10^2$, relative to the tastant. As will be appreciated, the various ranges and amounts of the compound of Formula I can be used, with modifications if preferred, in each of the embodiments described herein. The composition may also comprise $10^{-4}$% to $10^{-1}$% of the compound of Formula I relative to the sweet tastant, by weight.

The compound according to Formula I, or any of the specific subgroups, subclasses, or specific compounds described above, can be typically present in the food product in an amount ranging from about 0.001 mg to about 10 g per serving, preferably about 0.01 mg to about 5 g per serving, or alternatively, from 0.05 mg to about 1 g per serving. The present invention also contemplates food products with amounts of the compound of Formula I of about 0.05 mg, 0.1 mg, 0.5 mg, 1 mg, 5 mg, 10 mg, 25 mg, 50 mg, 100 mg, 500 mg, 1 g, 2 g, 5 g and 8 g per serving.

The method may be performed such that the sweet taste of the food product or food ingredient being enhanced by the compound of Formula I is enhanced by at least about 10%, 20%, 30%, 40%, 50%, 60%, 70%, 80%, 90%, or 95%, or from about 60% to about 99%, or alternatively from about 20% to about 50%. Thus, in a more specific embodiment, the method comprises administering a food product or food ingredient comprising a sweet tastant and one or more compounds according to Formula I, wherein the one or more compounds according to Formula I are present in an amount sufficient to enhance a sweet taste, produced by the food product, by at least about 10%, 20%, 30%, 40%, 50%, 60%, 70%, 80%, 90%, or 95%, or from about 60% to about 99%, or alternatively from about 30% to about 70%. Of course, in other embodiments, the sweetness may be enhanced to differing extents.

Any amount of the compound of Formula I that provides the desired degree of sweetness enhancement can be used. For example, a compound of Formula I may be used at a concentration of about 30 µg/L to about 1.5 g/L to enhance a sweet taste. Alternatively, concentrations of about 0.1 to 100 mg/L of a compound of Formula I may be used to enhance a sweet taste. It is contemplated that between 0.1 mg/L and 100 mg/L of the compound of Formula I is present and between 10 g/L and 100 g/L of sweet tastant is present. For example, a composition could contain 0.1 mg/L, 1 mg/L, or 10/L mg of the compound of Formula I for 10 mg/L of the tastant. Alternatively, the composition could contain 0.5 mg/L, 5 mg/L or 50 mg/L of the compound of Formula I for 50 mg/L of the tastant. In other embodiments, the composition contains 1 mg/L, 10 mg/L or 100 mg/L of the compound of Formula I for 100 g/L of the tastant.

In one embodiment, the present invention is directed to a method of enhancing the sweet taste of a food product selected from a beverage or drink comprising administering to a subject a beverage or drink comprising a sweet tastant and one or more compounds according to Formula I. Examples of suitable beverages in which having a sweet taste is desired include, but are not limited to coffee, teas, such as black tea, green tea, fermented tea, semi-fermented tea, carbonated soft drinks, such as COKE® and PEPSI®, non-carbonated soft drinks, lemonade, juices and other fruit drinks, sports drinks, such as GATORADE®, iced teas, coca, alcoholic beverages, such as beers, wines and liquors, and KOOL-AID.® In certain embodiments, the sweetness enhancing amount of a compound according to Formula I, or any of the specific subgroups, subclasses, or specific compounds described above, has a range of from about 0.01 milligrams to about 5.0 grams per 100 mL. In other embodiments, the sweetness enhancing effective amount of a compound according to Formula I, or any of the specific subgroups, subclasses, or specific compounds described above, has a range of from about 0.1 mg to about 2 grams per 1 L. Alternatively, a compound according to Formula I, or any of the specific subgroups, subclasses, or specific compounds described above, is administered in an amount of about 1 gram per 100 mL. In one embodiment, the beverage or drink comprises one sweet tastant. In another embodiment, it comprises more than one sweet tastant. In certain embodiments, the beverage or drink comprises sucrose and corn syrup, or it comprises sucrose and aspartame, or it comprises saccharin and sucralose as sweet tastants.

One embodiment of the invention is directed to a method of enhancing the sweet taste of a cola beverage, such as COKE® or PEPSI® comprising administering to a subject a cola drink comprising a sweet tastant and one or more compounds according to Formula I. In a preferred embodiment, the cola beverage will contain a reduced amount of sugar but maintain substantially the original level of sweet taste.

Cola beverages are prepared by mixing cola concentrate with carbonated water. Typically about 50 mL of cola concentrate is added per 250 mL of carbonated water. Cola concentrate can be prepared by mixing cola flavor, caramel color, and optionally caffeine with water, one or more sweet tastants, one or more compounds of Formula I, and one or more acid components.

A cola flavor refers to either a natural or artificial flavor. Such cola flavors are commercially available. Commercial cola flavors are available, for example, from International Flavor and Fragrances, Dayton, N.J.; Artificial—#13573011 and Natural #K3559549. Commercial cola flavors are also available from Tastemaker, Cincinnati, Ohio, and Givaudan Roure, Clifton, N.J.

The acid component refers to an ingredient that contributes sourness to the beverage and is added to balance the flavor profile by reducing chemical or sweetener side tastes. Acids may include malic acid, citric acid, phosphoric acid or combinations thereof.

Examples of sweet tastants include but are not limited to the group consisting of sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®. Sucrose, saccharin, sucralose, and aspartame are preferred. As discussed supra, the compositions of the invention can comprise more than one sweet tastant. For example, the food products of this invention can comprise both sucrose and corn syrup as sweet tastants, or sucrose and aspartame as sweet tastants, or saccharin and sucralose as sweet tastants.

For example, the cola concentrate can prepared by mixing phosphoric acid (75% Rhone-Poulenc), citric acid (anhydrous, ADM, Decatur, Ill.), caffeine (Mallinckrodt, Paris, Ky.), caramel Color (DS400, Sethness, Chicago, Ill.), cola Flavor (SN018976, International Flavors and Fragrances, Dayton, N.J.), sucrose, one or more compounds of Formula I, and water. The concentrate is blended until all ingredients are dissolved (30-40 minutes) using a magnetic stirring plate. Fifty milliliters of the concentrate are added to 250 mL of carbonated water to complete the preparation of the cola beverage. Fifty milliliters of cola concentrate typically contains from 0.01 to 5 mL of phosphoric acid, preferably about 0.01-1 mL, 0.1 to 100 g of sucrose, preferably about 1-10 g, about $1\times10^{-6}$ g to 10 g of a compound of Formula I, preferably about $1\times10^{-3}$ g to 1 g, about 0.001 g to 0.1 g of citric acid, preferably about 0.005-0.1 g, 0.001 to 1 g of caffeine, preferably about 0.01 to 0.1 g of caffeine, 0.001 to 5 g of caramel flavor, preferably about 0.05 to 1 g, 0.001 to about 10 mL of cola flavor, preferably about 0.01 to about 2 mL.

The compound according to Formula I, or any of the specific subgroups, subclasses, or specific compounds described above, can be typically present in an amount ranging from about 0.00001% to about 50% by weight, preferably about 0.0001% to about 2% by weight, or alternatively, from 0.0001% to about 0.1% by weight. The present invention also contemplates an amount of about 0.0001% to about 1%, preferably about, 0.0005%, 0.001%, 0.002%, 0.005%, 0.01%, 0.05%, 0.1%, 0.3%, 0.8%, 1.5%, by weight, of the cola beverage.

In each of the embodiments of the methods described herein, a compound of Formula I, or any of the specific subgroups, subclasses, or specific compounds described above, may be used in varying ratios to the tastant, i.e. the agent that is believed to cause the sweet taste. For example, a composition of the invention may comprise a compound of Formula I in a molar ratio of about $1:10^6$ to about 10:1, or alternatively administered in a molar ratio of about $1:10^5$, about $1:10^4$, about $1:10^3$, about $1:10^2$, relative to the tastant. As will be appreciated, the various ranges and amounts of the compound of Formula I can be used, with modifications if preferred, in each of the embodiments described herein. The composition may also comprise $10^{-4}$% to $10^{-1}$% of the compound of Formula I relative to the sweet tastant, by weight.

The compound according to Formula I, or any of the specific subgroups, subclasses, or specific compounds described above, can be typically present in the cola beverage in an amount ranging from about 0.001 mg to about 10 g per serving, preferably about 0.01 mg to about 5 g per serving, or alternatively, from 0.05 mg to about 1 g per serving. The present invention also contemplates cola beverages with amounts of the compound of Formula I of about 0.05 mg, 0.1 mg, 0.5 mg, 1 mg, 5 mg, 10 mg, 25 mg, 50 mg, 100 mg, 500 mg, 1 g, 2 g, 5 g and 8 g per serving.

Any amount of the compound of Formula I that provides the desired degree of sweetness enhancement can be used. For example, a compound of Formula I may be used at a concentration of about 30 µg/L to about 1.5 g/L to enhance a sweet taste. Alternatively, concentrations of about 0.1 to 100 mg/L of a compound of Formula I may be used to enhance a sweet taste. It is contemplated that between 0.1 mg/L and 100 mg/L of the compound of Formula I is present and between 10 g/L and 100 g/L of sweet tastant is present. For example, a composition could contain 0.1 mg/L, 1 mg/L, or 10/L mg of the compound of Formula I for 10 mg/L of the tastant. Alternatively, the composition could contain 0.5 mg/L, 5 mg/L or 50 mg/L of the compound of Formula I for 50 mg/L of the tastant. In other embodiments, the composition contains 1 mg/L, 10 mg/L or 100 mg/L of the compound of Formula I for 100 g/L of the tastant.

In certain embodiments, the improved food product, such as the cola beverage, e.g., COKE® or PEPSI,® will contain a reduced amount of sugar compared to the prior art cola beverage. The method may be performed such that the amount of sugar required to maintain the desired sweetness of the cola beverage is reduced by at least about 10%, 20%, 30%, 40%, 50%, 60%, 70%, 80%, 90%, or 95%, or from about 60% to about 99%, or alternatively from about 20% to about 50%. Thus, in a more specific embodiment, the cola beverage comprising a sweet tastant and one or more compounds according to Formula I, contains one or more compounds according to Formula I in an amount sufficient to reduce the amount of sugar required to maintain the desired sweetness of the beverage is reduced by 10%, 20%, 30%, 40%, 50%, 60%, 70%, 80%, 90%, or 95%, or from about 60% to about 99%, or alternatively from about 30% to about 70%. Of course, in other embodiments, the amount of sugar required may be decreased to differing extents.

Additionally, the invention is directed to a process of preparing an improved food product, wherein the improvement comprises adding one or more compounds according to Formula I, or any of the specific subgroups, subclasses, or specific compounds described above, to a food product. In certain embodiments, the one or more compounds according to Formula I, or any of the specific subgroups, subclasses, or specific compounds described above, are added to the food product in an amount of about 1% to about 25%, about 1% to about 10%, or about 5%, 10%, or 15%, by weight.

In another embodiment, the present invention is directed to a method of enhancing the sweet taste of an animal food product comprising administering to a subject an animal food product comprising a sweet tastant and one or more compounds according to Formula I, or any of the specific subgroups, subclasses, or specific compounds described above. The one or more compounds are preferably in an amount sufficient to enhance one or more sweet tastes associated with the animal food product. Animal food products are well known in the art, see, e.g., U.S. Pat. No. 6,403,142, and include dog food, cat food, rabbit food, and the like. The animal food product may also be food products useful for feeding livestock, such as cattle, bison, pigs, chicken, and the like. In another embodiment, the animal food composition of the present invention is a solid hypoallergenic pet food comprising a component that contains protein or protein fragments wherein all of said component is partially hydrolyzed and further comprises one or more compounds according to Formula I, or any of the specific subgroups, subclasses, or specific compounds described above. In certain embodiments, the one or more compounds according to Formula I, or any of the specific subgroups, subclasses, or specific compounds described above, are added to an animal food product in an amount as described above for food products.

Any of the animal food products described herein comprise one or more sweet tastants and one or more of compounds according to Formula I. In one embodiment, the animal food products comprises one sweet tastant. In a further embodiment, the food product comprises more than one sweet tastant. In certain embodiments, the food product comprises sucrose and corn syrup as sweet tastants, or sucrose and aspartame, or saccharin and sucralose. In another embodiment, the animal food product contains a sweet tastant selected from sugar (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®.

In another aspect, the present invention is directed to method of enhancing the sweet taste of a pharmaceutical composition comprising administering a subject a pharmaceutical composition comprising a sweet tastant and a compound of Formula I, as defined above, including any of the specific embodiments, subclasses, or species described above, and one or more pharmaceutically acceptable carriers. Preferred compositions are pharmaceutical compositions comprising a compound selected from one or more embodiments listed above, and one or more pharmaceutically acceptable excipients. Pharmaceutical compositions that comprise one or more compounds of Formula I, or any of the specific subgroups, subclasses, or specific compounds described above, may be used to formulate pharmaceutical drugs containing one or more active agents that exert a biological effect other than sweetness enhancement.

The pharmaceutical composition preferably further comprises one or more active agents that exert a biological effect. Such active agents includes pharmaceutical and biological agents that have an activity other than taste enhancement. Such active agents are well known in the art. See, e.g., The Physician's Desk Reference. Such compositions can be prepared according to procedures known in the art, for example, as described in Remington's Pharmaceutical Sciences, Mack Publishing Co., Easton, Pa., USA. In one embodiment, such an active agent includes bronchodilators, anorexiants, antihistamines, nutritional supplements, laxatives, analgesics, anesthetics, antacids, $H_2$-receptor antagonists, anticholinergics, antidiarrheals, demulcents, antitussives, antinauseants, antimicrobials, antibacterials, antifungals, antivirals, expectorants, anti-inflammatory agents, antipyretics, and mixtures thereof.

In another embodiment, the method of enhancing the sweet taste of a pharmaceutical composition comprises administering a pharmaceutical composition containing an active agent is selected from the group consisting of antipyretics and analgesics, e.g., ibuprofen, acetaminophen, or aspirin; laxatives, e.g., phenolphthalein dioctyl sodium sulfosuccinate; appetite depressants, e.g., amphetamines, phenylpropanolamine, phenylpropanolamine hydrochloride, or caffeine; antacidics, e.g., calcium carbonate; antiasthmatics, e.g., theophylline; antidiuretics, e.g., diphenoxylate hydrochloride; agents active against flatulence, e.g., simethecon; migraine agents, e.g., ergotaminetartrate; psychopharmacological agents, e.g., haloperidol; spasmolytics or sedatives, e.g., phenobarbitol; antihyperkinetics, e.g., methyldopa or methylphenidate; tranquilizers, e.g., benzodiazepines, hydroxinmeprobramates or phenothiazines; antihistaminics, e.g., astemizol, chlorpheniramine maleate, pyridamine maleate, doxlamine succinate, bromopheniramine maleate, phenyltoloxamine citrate, chlorocyclizine hydrochloride, pheniramine maleate, and phenindamine tartrate; decongestants, e.g., phenylpropanolamine hydrochloride, phenylephrine hydrochloride, pseudoephedrine hydrochloride, pseudoephedrine sulfate, phenylpropanolamine bitartrate, and ephedrine; beta-receptor blockers, e.g., propanolol; agents for alcohol withdrawal, e.g., disulfuram; antitussives, e.g., benzocaine, dextromethorphan, dextromethorphan hydrobromide, noscapine, carbetapentane citrate, and chlophedianol hydrochloride; fluorine supplements, e.g., sodium fluoride; local antibiotics, e.g., tetracycline or cleocine; corticosteroid supplements, e.g., prednisone or prednisolone; agents against goiter formation, e.g., colchicine or allopurinol; antiepileptics, e.g., phenyloine sodium; agents against dehydration, e.g., electrolyte supplements; antiseptics, e.g., cetylpyridinium chloride; NSAIDs, e.g., acetaminophen, ibuprofen, naproxen, or salts thereof; gastrointestinal active agents, e.g., loperamide and famotidine; various alkaloids, e.g., codeine phosphate, codeine sulfate, or morphine; supplements for trace elements, e.g., sodium chloride, zinc chloride, calcium carbonate, magnesium oxide, and other alkali metal salts and alkali earth metal salts; vitamins; ion-exchange resins, e.g., cholestyramine; cholesterol-depressant and lipid-lowering substances; antiarrhythmics, e.g., N-acetylprocainamide; and expectorants, e.g., guaifenesin.

Active substances which have a particularly unpleasant taste include antibacterial agents such as ciprofloxacin, ofloxacin, and pefloxacin; antiepileptics such as zonisamide; macrolide antibiotics such as erythromycin; beta-lactam antibiotics such as penicillins and cephalosporins; psychotropic active substances such as chlorpromazine; active substances such as sulpyrine; and agents active against ulcers, such as cimetidine.

In another embodiment, the method of enhancing the sweet taste of a pharmaceutical composition comprises administering a pharmaceutical composition comprising a sweet tastant, one or more compounds according to Formula I and at least one amino acid selected from the group consisting of glycine, L-alanine, L-arginine, L-aspartic acid, L-cystine, L-glutamic acid, L-glutamine, L-histidine, L-isoleucine, L-leucine, L-lysine, L-methionine, L-ornithine, L-phenylalanine, L-proline, L-serine, L-threonine, L-tryptophan, L-tyrosine, L-valine, creatine, and mixtures thereof.

In a further embodiment of the present invention, the pharmaceutical product comprises one sweet tastant. In another embodiment, the pharmaceutical product comprises more than one sweet tastant. In another embodiment, the pharmaceutical product comprises sucrose and corn syrup as sweet tastants, or sucrose and aspartame, or saccharin and sucralose. In one embodiment, the food product comprises one sweet tastant. In another embodiment, the food product comprises more than one sweet tastant. In certain embodiments, the food product comprises sucrose and corn syrup, or sucrose and aspartame, or saccharin and sucralose as sweet tastants. In another embodiment, the pharmaceutical composition contains a sweet tastant selected from sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®.

The method of enhancing the sweet taste of a pharmaceutical composition comprises administering pharmaceutical compositions in any form suitable to achieve their intended purpose. Preferably, however, the composition is one which can be administered buccally or orally. Alternatively, the pharmaceutical composition may be an oral or nasal spray.

The method of enhancing the sweet taste of a pharmaceutical composition comprises administering a pharmaceutical composition in any form suitable for administration to any animal that can experience the beneficial effects of one or more compounds according to Formula I, or any of the specific subgroups, subclasses, or specific compounds described above. Foremost among such animals are humans, although the invention is not intended to be so limited. Other suitable animals include canines, felines, dogs, cats, livestock, horses, cattle, sheep, and the like. A veterinary composition, as used herein, refers to a pharmaceutical composition that suitable for non-human animals. Such veterinary compositions are known in the art.

In another embodiment, the pharmaceutical composition in which the taste is enhanced is selected from a liquid dosage forms for oral administration, including pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

In a further embodiment, the invention is directed to method of enhancing the sweet taste of a chewable tablet comprising administering to a subject a chewable tablet comprising a sweet tastant, one or more compounds according to Formula I, and one or more biologically active agents. Chewable tablets are known in the art. See, e.g., U.S. Pat. Nos. 4,684,534 and 6,060,078, each of which is incorporated by reference in its entirety. Any kind of medicament may be contained in the chewable tablet, preferably a medicament of bitter taste, natural plant extracts or other organic compounds. More preferably, vitamins such as vitamin A, vitamin B, vitamin $B_1$, vitamin $B_2$, vitamin $B_6$, vitamin C, vitamin E and vitamin K; natural plant extracts such as Sohgunjung-tang extracts, Sipchundaebo-tang extracts and *Eleutherococcus senticosus* extracts; organic compounds such as dimenhydrinate, meclazine, acetaminophen, aspirin, phenylpropanolamine, and cetylpyridinium chloride; or gastrointestinal agents such as dried aluminum hydroxide gel, domperidone, soluble azulene, L-glutamine and hydrotalcite may be contained in the core.

In another embodiment, the present invention is directed to a method of enhancing the sweet taste of an orally disintegrating composition comprising administering to a subject an orally disintegrating composition wherein said orally disintegrating composition comprises a sweet tastant and one or more compounds according to Formula I, or any of the specific subgroups, subclasses, or specific compounds described above. Orally disintegrating tablets are known in the art. See, e.g., U.S. Pat. Nos. 6,368,625 and 6,316,029, each of which is hereby incorporated by reference in its entirety.

In another embodiment, the present invention is further directed to a method of enhancing the sweet taste of a nasal composition comprising administering to a subject a nasal composition comprising a sweet tastant and one or more compounds according to Formula I, or any of the specific subgroups, subclasses, or specific compounds described above. Nasal sprays are known in the art. See, e.g., U.S. Pat. No. 6,187,332. Addition of one or more compounds according to Formula I to a nasal spray can reduce the experience of an unpleasant taste associated with the composition of the nasal spray. By way of a nonlimiting example, a nasal spray composition according to the present invention comprises water (such as 95-98 weight percent), a citrate (such as 0.02 M citrate anion to 0.06 M citrate anion), a compound according to Formula I, and optionally phosphate (such as 0.03 M phosphate to 0.09 M phosphate).

In another embodiment, the present invention is directed to a method of enhancing the sweet taste of a solid dosage form, comprising administering to a subject a solid dosage form comprising a water and/or saliva activated effervescent granule, such as one having a controllable rate of effervescence, a sweet tastant, and a compound according to Formula I, or any of the specific subgroups, subclasses, or specific compounds described above. The effervescent composition may further comprise a pharmaceutically active compound. Effervescent pharmaceutical compositions are known in the art. See, e.g., U.S. Pat. No. 6,649,186, which is incorporated by reference in its entirety. The effervescent composition can be used in pharmaceutical, veterinary, horticultural, household, food, culinary, pesticidal, agricultural, cosmetic, herbicidal, industrial, cleansing, confectionery and flavoring applications. Formulations incorporating the effervescent composition comprising a compound according to Formula I can further include one or more additional adjuvants and/or active ingredients which can be chosen from those known in the art including flavors, diluents, colors, binders, filler, surfactant, disintegrant, stabilizer, compaction vehicles, and non-effervescent disintegrants.

In another embodiment, the present invention is directed a method of enhancing the sweet taste of a film-shaped or wafer-shaped pharmaceutical composition, comprising administering to a subject a film-shaped or wafer-shaped pharmaceutical composition that comprises a sweet tastant and a compound according to Formula I, or any of the specific subgroups, subclasses, or specific compounds described above, and is capable of disintegrating. Such a film-shaped or wafer-shaped pharmaceutical composition can be configured, for example, as quickly disintegrating administration forms, e.g., administration forms disintegrating within a period of 1 second up to 3 minutes, or as slowly disintegrating administration forms, e.g., administration forms disintegrating within a period of 3 to 15 minutes.

The indicated disintegration times can be set to the above-mentioned ranges by using, for example, matrix-forming polymers which have different disintegrating, or solubility, characteristics. Thus, by mixing the corresponding polymer components, the disintegration time can be adjusted. In addition, disintegrants are known which "draw" water into the matrix and cause the matrix to burst open from within. As a consequence, certain embodiments of the invention include such disintegrants for the purpose of adjusting the disintegration time.

Suitable are polymers for use in the film-shaped or wafer-shaped pharmaceutical composition include cellulose derivatives, polyvinyl alcohol (e.g. Mowiol™), polyacrylates, polyvinyl pyrrolidone, cellulose ethers, such as ethyl cellulose, as well as polyvinyl alcohol, polyurethane, polymethacrylates, polymethyl methacrylates and derivatives and copolymerisates of the aforementioned polymers.

In certain embodiments, the total thickness of the film-shaped or wafer-shaped pharmaceutical composition according to the invention is preferably 5 µm up to 10 mm, preferably 30 µm to 2 mm, and with particular preference 0.1 mm to 1 mm. The pharmaceutical preparations may round, oval, elliptic, triangular, quadrangular or polygonal shape, but they may also have any rounded shape.

In another embodiment, the present invention is directed to a method of enhancing the sweet taste of a composition comprising a medicament or agent contained in a coating that surrounds a gum base formulation comprising administering the composition, a sweet tastant and a sweetness-enhancing amount of a compound according to Formula I, or any of the specific subgroups, subclasses, or specific compounds described above. Preferably, the coating comprises at least 50% by weight of the entire product. As the center is chewed, the medicament or agent is released into the saliva. For example, U.S. Pat. No. 6,773,716, which is incorporated herein by reference in its entirety, discloses a suitable medicament or agent contained in a coating that surrounds a gum base formulation. One or more compounds according to Formula I, or any of the specific subgroups, subclasses, or specific compounds described above, can be used in preparing the coating. Optionally, the composition may further comprise high-intensity sweeteners and appropriate flavors. It has been found that with respect to certain medicaments or agents that may have an astringent or bitter taste that by adding a sweetener enhancing agent to the formulation, that a much more palatable formulation, including the medicament, can be provided. In this regard, even though the medicament in, for example, its powder form may be bitter or have an offensive taste, the matrix used as the coating of the present invention, including the inhibiting agent, will afford a product having acceptable medicinal properties.

In a further embodiment, the invention is directed to a method of enhancing the sweet taste of a pharmaceutical composition suitable for aerosol administration, comprising administering to a subject, a pharmaceutical composition suitable for aerosol administration comprising a sweet tastant and a compound according to Formula I, or any of the specific subgroups, subclasses, or specific compounds described above, and a suitable carrier. The aerosol composition may further comprises pharmaceutically active agent. Aerosol compositions are known in the art. See, e.g., U.S. Pat. No. 5,011,678, which is hereby incorporated by reference in its entirety. As a nonlimiting example, an aerosol composition according to the present invention may comprise a medically effective amount of a pharmaceutically active substance, one or more compounds according to Formula I, or any of the specific subgroups, subclasses, or specific compounds described above, and a biocompatible propellant, such as a (hydro/fluoro)carbon propellant.

In another embodiment, the present invention is directed to a method of enhancing the sweet taste of a nutritional composition comprising administering a nutritional composition comprising a sweet tastant and one or more compounds according to Formula I, or any of the specific subgroups, subclasses, or specific compounds described above, and optionally one or more carriers. Examples of nutritional compositions having an undesirable taste include, but are not necessarily limited to, enteral nutrition products for treatment of nutritional deficit, trauma, surgery, Crohn's disease, renal disease, hypertension, obesity and the like, to promote athletic performance, muscle enhancement or general well being or inborn errors of metabolism such as phenylketonuria. In particular, such nutritional formulations may contain one or more amino acids which have a bitter or metallic taste or aftertaste. Such amino acids include, but are not limited to, an essential amino acids selected from the group consisting of L isomers of leucine, isoleucine, histidine, lysine, methionine, phenylalanine, threonine, tryptophan, tyrosine, and valine.

In certain embodiments, the administered pharmaceutical or comprises the compound according to Formula I, or any of the specific subgroups, subclasses, or specific compounds described above, in an amount ranging from about 0.001% to about 50% by weight, preferably about 0.1% to about 10% by weight, or alternatively, from 0.1% to about 1% by weight. The present invention also contemplates an amount of about 1% to about 20%, preferably about 1% to about 5%, about 1%, 3%, or 4%, by weight, of the pharmaceutical or nutritional composition.

In various embodiments, the method comprises administering the compound according to Formula I in an amount from about 0.01 mg to about 100 mg per 100 mL of the composition, or in an amount from about 0.01 mg to about 10 mg per 100 mL of the composition. Alternatively, the compound is administered an amount of about 0.1 mg/L to about 100 mg/L and the sweet tastant is administered in an amount of 10 g/L to 100 g/L, or in an amount ranging from $10^{-4}$% to $10^{-1}$% of the sweet tastant by weight, or the compound according to Formula I and the sweet tastant are administered in a ratio ranging from $1:10^6$ to $1:10^3$.

In each of the embodiments of the methods described herein, a compound of Formula I, or any of the specific subgroups, subclasses, or specific compounds described above, may be used in varying ratios to the tastant, i.e. the agent that is believed to cause the sweet taste. For example, a pharmaceutical or nutritional composition of the invention may comprise a compound of Formula I in a molar ratio of about $1:10^6$ to, or alternatively administered in a molar ratio of about $1:10^5$, about $1:10^4$, about $1:10^3$, about $1:10^2$, relative to the tastant. As will be appreciated, the various ranges and amounts of the compound of Formula I can be used, with modifications if preferred, in each of the embodiments described herein. The composition may also comprise $10^{-4}$% to $10^{-1}$% of the compound of Formula I relative to the sweet tastant, by weight.

The compound according to Formula I, or any of the specific subgroups, subclasses, or specific compounds described above, can be typically present in the pharmaceutical composition or nutritional composition in an amount ranging from about 0.001 mg to about 10 g per serving, preferably about 0.01 mg to about 5 g per serving, or alternatively, from 0.05 mg to about 1 g per serving. The present invention also contemplates compositions with amounts of the compound of Formula I of about 0.05 mg, 0.1 mg, 0.5 mg, 1 mg, 5 mg, 10 mg, 25 mg, 50 mg, 100 mg, 500 mg, 1 g, 2 g, 5 g and 8 g per serving.

The method may be performed such that the sweet taste of the pharmaceutical composition or nutritional composition being enhanced by the compound of Formula I is enhanced by at least about 10%, 20%, 30%, 40%, 50%, 60%, 70%, 80%, 90%, or 95%, or from about 60% to about 99%, or alternatively from about 20% to about 50%. Thus, in a more specific embodiment, the method comprises administering a pharmaceutical composition or nutritional composition comprising one or more food ingredients and one or more compounds according to Formula I, wherein the one or more compounds according to Formula I are present in an amount sufficient to enhance a sweet taste, produced by the tastant in pharmaceutical composition or nutritional composition by at least about 10%, 20%, 30%, 40%, 50%, 60%, 70%, 80%, 90%, or 95%, or from about 60% to about 99%, or alternatively from about 30% to about 70%. Of course, in other embodiments, the sweetness may be enhanced to differing extents.

Any amount of the compound of Formula I that provides the desired degree of sweetness enhancement can be used. For example, a compound of Formula I may be used at a concentration of about 30 µg/L to about 1.5 g/L to enhance a sweet taste. Alternatively, concentrations of about 0.1 mg/L to 100 mg/L of a compound of Formula I may be used to enhance a sweet taste.

In another embodiment, the present invention is directed to a method of enhancing the sweet taste of a dental hygienic composition comprising administering a dental hygienic composition comprising a sweet tastant and one or more compounds according to Formula I, or any of the specific subgroups, subclasses, or specific compounds described above. Dental hygienic compositions are known in the art and include but are not necessarily limited to toothpaste, mouthwash, plaque rinse, dental floss, dental pain relievers (such as ANBESOL™), and the like. In certain embodiments, the one or more compounds according to Formula I are present in the dental hygienic composition in an amount of about 1% to about 20%, preferably about 1% to about 5%, or about 5%, 10%, or 15%, by weight. In one embodiment, the dental hygienic composition comprises more than one sweet tastant. In certain embodiments, the hygienic composition comprises sucrose and corn syrup, or it comprises sucrose and aspartame, or it comprises saccharin and sucralose as sweet tastants.

In another embodiment, the present invention is directed to a method of enhancing the sweet taste of a cosmetic product comprising administering to a subject a cosmetic product comprising a sweet tastant and one or more compounds according to Formula I, or any of the specific subgroups, subclasses, or specific compounds described above. For example, but not by way of limitation, the cosmetic product comprising a compound according to Formula I, or any of the specific subgroups, subclasses, or specific compounds described above, may be a face cream, lipstick, lip gloss, and the like. In certain embodiments, the one or more compounds according to Formula I, or any of the specific subgroups, subclasses, or specific compounds described above, are added to a cosmetic product in an amount of about 1% to about 20%, preferably about 1% to about 5%, or about 1%, 2%, or 3%, by weight. Other suitable compositions of the invention include lip balm, such as CHAPSTICK® or BURT'S BEESWAX® Lip Balm, further comprising one or more compounds according to Formula I, or any of the specific subgroups, subclasses, or specific compounds described above.

The method of the present invention in its various embodiments may also be used to mask one or more tastes selected from the group consisting of bitter, sour, salty, or umami. Preferably, the method of the present invention inhibits a bitter taste.

As used herein, the phrase "mask a taste" and grammatical variants thereof, such as "masking," refers to interfering with the perception of a taste. The taste may be sensed to a lesser degree or not sensed at all by application of the present invention.

In another embodiment, a compound according to Formula I, or any of the specific subgroups, subclasses, or specific compounds described above, is useful for masking a taste, such as an undesirable taste of a food product by creating a sweet taste. Examples of food products having an undesirable taste include, but are not necessarily limited to, citrus fruits such as grapefruit, orange, and lemon; vegetables such as tomato, pimento, celery, melon, carrot, potato and asparagus; seasoning or flavoring materials, such as soy sauce and red pepper; soybean products; fish products; meats and processed meats; dairy products such as cheese; breads and cakes; and confectioneries such as candies, chewing gum and chocolate. Other examples of food products envisioned in accordance with the present invention are described below and throughout the specification.

In another embodiment, the present invention is directed to a method of masking an undesirable taste of food product comprising administering to a subject a food product comprising a sweet tastant and one or more compounds according to Formula I, or any of the specific subgroups, subclasses, or specific compounds described above. Preferably, the food product is one which exhibits an desirable taste, which can be masked by a compound according to Formula I, or any of the specific subgroups, subclasses, or specific compounds described above. Furthermore, in a preferred embodiment, the food product comprises a compound of Formula I, or any of the specific subgroups, subclasses, or specific compounds described above in an amount sufficient to mask an undesirable taste.

Specific food products to which one of more compounds of Formula I, or any of the specific subgroups, subclasses, or specific compounds described above, can be added include but are not necessarily limited to, potassium chloride, ammonium chloride, sodium chloride (e.g., table salt), magnesium chloride, halide salts, naringin, caffeine, urea, magnesium sulfate, acetosulfames, aspirin, potassium benzoate, potassium bicarbonate, potassium carbonate, potassium nitrate, potassium nitrite, potassium sulfate, potassium sulfite, potassium glutamate, food preservatives in their physiologically acceptable salts, antibiotics, unsweetened chocolate, cocoa beans, yoghurt, preservatives, flavor enhancers, dietary supplements, gelling agents, pH control agents, nutrients, processing aids, bodying agents, dispersing agents, stabilizers, colorings, coloring diluents, anticaking agents, antimicrobial agents, formulation aids, leavening agents, surface active agents, anticaking agents, nutrient supplements, alkali, acids, sequestrants, denuding agents, general purpose buffers, thickeners, cooked out juice retention agents, color fixatives in meat and meat products, color fixatives in poultry and poultry products, dough conditioners, maturing agents, yeast foods, mold retardants, emulsifiers, texturizers, binders, water correctives, miscellaneous and general purpose food additives, tableting aids, lye peeling agents, washing water agents, oxidizers, antioxidants, enzymes, extenders, fungicides, cake mixes, coffee, tea, dry mixes, non-dairy creamers, salts, animal glue adjuvant, cheese, nuts, meat and meat products, poultry and poultry product, pork and pork products, fish and fish products, vegetable and vegetable products, fruit and fruit products, smoked products such as meat, cheese fish, poultry, and vegetables, whipping agents, masticatory substances in chewing gums, dough strengtheners, animal feed, poultry feed, fish feed, pork feed, defoaming agents, juices, liquors, substances or drinks containing alcohol, beverages including but not limited to alcoholic beverages and non-alcoholic carbonated and/or non-carbonated soft drinks, whipped toppings, bulking agents used in eatables including but not limited to starches, corn solids, polysaccharides and other polymeric carbohydrates, icings, as well as potassium-containing or metal-containing substances with undesirable tastes and the like. The compound according to Formula I, or any of the specific subgroups, subclasses, or specific compounds described above, can be typically present in an amount ranging from about 0.001% to about 50% by weight, preferably about 0.1% to about 10% by weight, or alternatively, from 0.1% to about 1% by weight. The present invention also contemplates an amount of about 1% to about 20%, preferably about 1% to about 5%, about 1%, 3%, or 4%, by weight, of the composition The method may be performed such that the taste of the food product being masked by the compound of Formula I is reduced by at least about 10%, 20%, 30%, 40%, 50%, 60%, 70%, 80%, 90%, or 95%, or from about 60% to about 99%, or alternatively from about 20% to about 50%. Thus, in a more specific embodiment, the method comprises administering a food product comprising one or more food ingredients and one or more compounds according to Formula I, wherein the one or more compounds according to Formula I are present in an amount sufficient to mask a bitter taste, produced by the food product, by at least about 10%, 20%, 30%, 40%, 50%, 60%, 70%, 80%, 90%, or 95%, or from about 60% to about 99%, or alternatively from about 30% to about 70%. Of course, in other embodiments, a taste may be masked to differing extents.

Any amount of the compound of Formula I that provides the desired degree of taste masking can be used. For example, a compound of Formula I may be used at a concentration of about 30 μg/L to about 1.5 g/L to mask a bitter taste. Alternatively, concentrations of about 0.1 mg/L to 100 mg/L of a compound of Formula I may be used to mask an undesirable taste.

A food product may also include beverages and drinks. Examples of suitable beverages include, but are not limited to coffee, teas, such as black tea, green tea, fermented tea, semi-fermented tea, carbonated soft drinks, such as COKE® and PEPSI®, non-carbonated soft drinks, lemonade, juices and other fruit drinks, sports drinks, such as GATORADE®, iced teas, coca, alcoholic beverages, such as beers, wines and liquors, and KOOL-AID.® In certain embodiments, the taste masking effective amount of a compound according to Formula I, or any of the specific subgroups, subclasses, or specific compounds described above, has a range of from about 0.001 to about 5.0 grams per 100 mL. In other embodiments, the taste masking effective amount of a compound according to Formula I, or any of the specific subgroups, subclasses, or specific compounds described above, has a range of from about 0.5 to about 2 grams per 100 mL. Alternatively, a compound according to Formula I, or any of the specific subgroups, subclasses, or specific compounds described above, is administered in an amount of about 1 gram per 100 mL. It is contemplated that between 0.1 mg/L and 100 mg/L of the compound of Formula I is present and between 10 g/L and 100 g/L of sweet tastant is present. For example, a composition could contain 0.1 mg/L, 1 mg/L, or 10 mg/L of the compound of Formula I and 10 mg/L of the tastant. Alternatively, the composition could contain 0.5 mg/L, 5 mg/L, or 50 mg/L of the compound of Formula I and 50 mg/L of the tastant. In other embodiments, the composition contains 1 mg/L, 10 mg/L or 100 mg/L of the compound of Formula I and 100 g/L of the tastant.

In another embodiment, the present invention is directed to a method of increasing the palatability and/or intake of food, comprising administering to a subject in need of such treatment a food product comprising a sweet tastant and one or more compounds according to Formula I, or any of the specific subgroups, subclasses, or specific compounds described above, in an amount sufficient to increase the palatability and/or intake of food. Thus, according to the present invention, a compound according to Formula I, or any of the specific subgroups, subclasses, or specific compounds described above, may be administered to a subject so that the palatability of food, as experienced by said subject, is increased. Without being bound by theory, it is believed that a higher palatability of food can lead to a greater intake of food by the subject. Thus, in certain embodiments, by administering a compound according to Formula I, or any of the specific subgroups, subclasses, or specific compounds described above, to a subject, the subject will consume an increased amount of food compared to the subject's food intake when not being administered a compound of Formula I, or any of the specific subgroups, subclasses, or specific compounds described above. In other embodiments, by administering a compound according to Formula I, or any of the specific subgroups, subclasses, or specific compounds described above, to a subject, the subject will have a higher caloric intake compared to the subject's caloric intake when not being administered a compound of Formula I, or any of the specific subgroups, subclasses, or specific compounds described above. In other embodiments, administering a compound according to Formula I, or any of the specific subgroups, subclasses, or specific compounds described above, to a subject can be means to overcome taste impairment associated with radiation treatments for cancer, with certain drugs and loss of taste sensations in the elderly.

In each of the embodiments of methods described above, the subject of the method, unless otherwise limited to, may be any animal which is need of the particular treatment or effect of the method. Such animals include but are not limited to a cow, horse, sheep, pig, chicken, turkey, quail, cat, dog, mouse, rat, rabbit, monkey, or guinea pig taste modulating protein. In other embodiments, the animal is a livestock animal, a domesticated animal, or an animal kept as a pet. In particular embodiments, the subject of the claimed method is a human.

Furthermore, in each of the embodiments of the methods described herein, a compound of Formula I may be used in varying ratios to the agent that is believed to cause the unwanted taste, such as a bitter taste. For example, a composition of the invention may comprise a compound of Formula I in a molar ratio of about 0.001:1 to about 10:1, or alternatively administered in a molar ratio of about 0.01:1, about 0.02:1, about 0.05:1, about 0.1:1, or about 0.5:1, relative to the agent causing the unwanted taste. As will be appreciated, the various ranges and amounts of the compound of Formula I can be used, with modifications if preferred, in each of the embodiments described herein.

In another example, the present invention is directed to a method of masking the bitter taste of a pharmaceutical composition, comprising administering to a subject in need of such method a pharmaceutical composition comprising a sweet tastant and a compound according to Formula I, wherein the pharmaceutical composition comprises a pharmaceutically active agent and optionally one or more excipients, and wherein the compound according to Formula I is administered as either a component of the pharmaceutical composition or as a separate dosage form, and wherein the molar ratio of the compound of Formula I to the pharmaceutically active agent is about $1:10^6$ to about 10:1, or alternatively administered in a molar ratio of about $1:10^5$, about $1:10^4$, about $1:10^3$, or about $1:10^2$, relative to the tastant. As will be appreciated, the various ranges and amounts of the compound of Formula I can be used, with modifications if preferred, in each of the embodiments described herein.

In certain embodiments, a single dose or two to four divided daily doses, provided on a basis of about 0.001 to 100 mg per kilogram of body weight per day, preferably about 0.01 to about 25 mg/kg of body weight per day is appropriate. When enhancing a taste receptor cell in vivo, the compound of Formula I is preferably administered orally.

An additional aspect of the present invention is a method of masking the undesirable of a pharmaceutical composition, comprising administering pharmaceutical composition comprising a sweet tastant and a compound according to Formula I, or any of the specific subgroups, subclasses, or specific compounds described above, to a subject receiving the pharmaceutical composition. The compound of Formula I may be administered together with the pharmaceutical composition as separate compositions, for example either concurrently or sequentially. The compound of Formula I may administered, or caused to be administered, prior to the pharmaceutical agent producing the taste to be enhanced or masked. Alternatively, the compound for Formula I may be administered as a component of the pharmaceutical composition.

The compound according to Formula I, or any of the specific subgroups, subclasses, or specific compounds described above, can be typically present in the composition in an amount ranging from about 0.0001 mg to about 500 mg per dose, preferably about 0.001 mg to about 100 mg, or alternatively, from 0.05 mg to about 10 mg per dose. The present invention also contemplates compositions with amounts of the compound of Formula I of about 0.0001 mg, 0.0005 mg, 0.001 mg, 0.005 mg, 0.01 mg, 0.05 mg, 0.1 mg, 0.5 mg, 1 mg, 5 mg, 10 mg, 25 mg, 50 mg, 100 mg, 500 mg per dose.

By way of additional examples, the method of masking the taste of a pharmaceutical composition may comprise masking a taste produced by one or more agents selected from the group consisting of antipyretics, analgesics, laxatives, appetite depressants, antacidics, antiasthmatics, antidiuretics, agents active against flatulence, antimigraine agents, psychopharmacological agents, spasmolytics, sedatives, antihyperkinetics, tranquilizers, antihistaminics, decongestants, beta-receptor blockers, agents for alcohol withdrawal, antitussives, fluorine supplements, local antibiotics, corticosteroid supplements, agents against goiter formation, antiepileptics, agents against dehydration, antiseptics, NSAIDs, gastrointestinal active agents, alkaloids, supplements for trace elements, ion-exchange resins, cholesterol-depressant agents, lipid-lowering agents, antiarrhythmics, and expectorants. Further specific examples of pharmaceutical compositions in accordance with the method of the invention are described below.

Additionally, the method of masking the taste of a pharmaceutical composition may comprise masking a taste produced by a counterterrorism pharmaceutical. Because of the increased risk of terrorist attacks, such as chemical, nuclear, or biological attacks, the use of counterterrorism pharmaceutical agents is expected to increase in the future. A counterterrorism pharmaceutical agent includes those pharmaceutical agents that are useful in counteracting agents that can be used in a terrorist attack. Agents that have been used in terrorist acts, or considered as useful for carrying out future terrorist acts, include ricin, sarin, radioactive agents and materials, and anthrax. Pharmaceutical agents that counteract these agents are useful as a counterterrorism pharmaceutical. Such counterterrorism pharmaceuticals include, but are not limited to, antibiotics such as ciprofloxacin and doxycycline; potassium iodide; and antiviral agents. Thus, in one embodiment of the present invention, the method may be performed such that the taste of a counterterrorism pharmaceutical, such as an antibiotic such as ciprofloxacin and doxycycline; potassium iodide; or an antiviral agent, is masked by the compound of Formula I by at least about 10%, 20%, 30%, 40%, 50%, 60%, 70%, 80%, 90%, or 95%, or from about 60% to about 99%, or alternatively from about 25% to about 50%. In another embodiment, the compound of Formula I is administered in a ratio of from about 10:1 to about 1:10 in relation to the counterterrorism agent.

In another embodiment, a compound according to Formula I, or any of the specific subgroups, subclasses, or specific compounds described above, is useful for masking an undesirable taste of a nutritional composition. Examples of nutritional compositions having an undesirable taste include, but are not necessarily limited to, enteral nutrition products for treatment of nutritional deficit, trauma, surgery, Crohn's disease, renal disease, hypertension, obesity and the like, to promote athletic performance, muscle enhancement or general well being or inborn errors of metabolism such as phenylketonuria. In particular, such nutritional formulations may contain one or more amino acids which have a bitter or metallic taste or aftertaste. Such amino acids include, but are not limited to, an essential amino acids selected from the group consisting of L isomers of leucine, isoleucine, histidine, lysine, methionine, phenylalanine, threonine, tryptophan, tyrosine, and valine. Further specific examples of nutritional compositions in accordance with the method of the invention are described below.

In one embodiment, the nutritional composition comprises one sweet tastant. In another embodiment, the nutritional composition comprises more than one sweet tastant. In certain embodiments, the nutritional composition comprises sucrose and corn syrup, or sucrose and aspartame, or saccharin and sucralose as sweet tastants. In another embodiment, the nutritional composition contains a sweet tastant selected from sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®.

By way of example, the method may be performed such that the taste being masked by the compound of Formula I is masked by at least about 10%, 20%, 30%, 40%, 50%, 60%, 70%, 80%, 90%, or 95%, or from about 60% to about 99%, or alternatively from about 20% to about 50% Thus, in a more specific embodiment, the method comprises administering a nutritional composition comprising a sweet tastant, a nutritional agent, optionally one or more excipients, and one or more compounds according to Formula I, wherein the one or more compounds according to Formula I are present in an amount sufficient to mask a undesired taste, produced by the nutritional agent, by at least about 10%, 20%, 30%, 40%, 50%, 60%, 70%, 80%, 90%, or 95%, or from about 60% to about 99%, or alternatively from about 10% to about 50%.

A compound according to Formula I may be incorporated into medical and/or dental compositions. Certain compositions used in diagnostic procedures have an unpleasant taste, such as contrast materials and local oral anesthetics. The enhancers of the invention may be used to improve the comfort of subjects undergoing such procedures by improving the taste of compositions. In addition, the enhancers of the invention may be incorporated into pharmaceutical compositions, including tablets and liquids, to improve their flavor and improve patient compliance particularly where the patient is a child or a non-human animal).

In another embodiment, a compound according to Formula I, or any of the specific subgroups, subclasses, or specific compounds described above, is used to enhance the taste of a cosmetic product. For example, but not by way of limitation, a compound according to Formula I may be incorporated into face creams, lipsticks, lip gloss, and the like. Also, a compound according to Formula I, or any of the specific subgroups, subclasses, or specific compounds described above, can be used to mask an unpleasant taste of lip balm, such as CHAPSTICK® or BURT's BEESWAX® Lip Balm.

In addition, a compound according to Formula I, or any of the specific subgroups, subclasses, or specific compounds described above, may be incorporated into compositions that are not traditional foods, pharmaceuticals, or cosmetics, but which may contact taste membranes. Examples include, but are not limited to, soaps, shampoos, toothpaste, denture adhesive, and glue on the surfaces of stamps and envelopes. Thus, the present invention also covers a process of preparing a composition that is not a traditional food, pharmaceutical, or cosmetic, but which may contact taste membranes, according to conventional methods, wherein the improvement comprises adding a compound of Formula I to said composition.

In another embodiment, a compound according to Formula I, or any of the specific subgroups, subclasses, or specific compounds described above, is used to mask the taste associated with one or more the following: bitter pharmaceutical alkaloids such as acetaminophen, ampicillin, chlorpheniramine, chlarithromycin, doxylamine, guaifenesin, ibuprofen, pseudoephedrine hydrochloride, and ranitidine, bitter pharmaceutical metallic salts such as zinc containing bioadhesives (denture adhesive), bitter vitamins, bitter components of foods such as creatine, limonin, naringin, quinizolate, and bitter components of beverages such as caffeine, and humulone. In one embodiment, the concentration of the compound according to Formula I used is in the range of 0.01 mM to 20 mM and may vary depending on the amount of bitter compound used and its bitterness.

In another embodiment, the present invention is directed to a method of masking the taste of a veterinary product, such as veterinary medicines, veterinary food products, veterinary supplements, and the like, that are administered to domesticated animals. In a preferred embodiment, a compound according to Formula I, or any of the specific subgroups, subclasses, or specific compounds described above, is used to mask a taste of a veterinary product administered to a cat or dog.

In one embodiment, in each of the methods of masking a taste described herein, a compound according to Formula I, or any of the specific subgroups, subclasses, or specific compounds described above, is administered in an amount effective to mask said taste. As a nonlimiting example, the taste masking effective amount of a compound according to Formula I, or any of the specific subgroups, subclasses, or specific compounds described above, administered in one embodiment is from about 0.01 to about 5.0 grams per 100 mL.

In one embodiment, the present invention is directed to a method of masking the taste of a pharmaceutical product, comprising administering to a subject a pharmaceutical product comprising a sweet tastant and a compound according to Formula I, or any of the specific subgroups, subclasses, or specific compounds described above, is administered in an amount that is sufficient, in combination with the administration of one or more additional sweetening agents, to enhance said taste. For example, in a method enhancing the sweet taste in a liquid pharmaceutical composition, the composition comprises a sweet tastant and a compound according to Formula I and another sweetening agent, wherein the amount of the compound of Formula I is about 25% to about 75% of the amount required to inhibit the bitter taste in the absence of the other taste inhibiting agent. Suitable sweetening agents include but are not limited to sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®.

In another embodiment the above described compounds may be used to enhance a taste modulating protein. Such inhibition may be in vitro or in vivo. The amount of the compound of Formula I, or any of the specific subgroups, subclasses, or specific compounds described above, used to inhibit the taste modulating protein may not necessarily be the same when used in vivo compared to in vitro. Factors such as pharmacokinetics and pharmacodynamics of the particular compound may require that a larger or smaller amount of the compound of Formula I, or any of the specific subgroups, subclasses, or specific compounds described above, be used when inhibiting a taste modulating protein in vivo. Accordingly, one aspect of the present invention is a method of enhancing a taste modulating protein, comprising contacting the taste modulating protein with a compound according to Formula I, or any of the specific subgroups, subclasses, or specific compounds described above.

In one embodiment of this aspect of the present invention, the method comprises contacting a cell with a compound of Formula I, or any of the specific subgroups, subclasses, or specific compounds described above, wherein said cell expresses said taste modulating protein.

In another embodiment of the present invention, the method comprises administering a compound of Formula I, or any of the specific subgroups, subclasses, or specific compounds described above, to a subject in an amount sufficient to inhibit a taste modulating protein, wherein said subject has or expresses said taste modulating protein. Furthermore, when administered orally, the compound may be dispersed or diluted by saliva.

The present invention is directed to a method of enhancing a taste modulating protein, comprising contacting said protein with a compound of Formula I, or any of the specific subclasses and specific compounds listed above, and enhancing the protein by at least about 10%, 20%, 30%, 40%, 50%, 60%, 70%, 80%, 90%, or 95%, or from about 50% to about 99%. In another embodiment, the method comprises contacting said protein with a compound of Formula I, or any of the specific subclasses and specific compounds listed above, and enhancing the protein by about 10% to about 50%. In another embodiment, the present invention is directed to a method of enhancing a taste modulating protein, comprising contacting said protein with a compound of Formula I, or any of the specific subclasses and specific compounds listed above, and enhancing the protein by at least about 10%, 20%, 30%, 40%, 50%, 60%, 70%, 80%, 90%, or 95%, or from about 50% to about 99%, or alternatively from about 10% to about 50%, and wherein said taste modulating protein is a naturally occurring taste modulating protein. In another embodiment, the present invention is directed to a method of enhancing a taste modulating protein, comprising contacting said protein with a compound of Formula I, or any of the specific subclasses or specific compounds listed above, and enhancing the protein by at least about 10%, 20%, 30%, 40%, 50%, 60%, 70%, 80%, 90%, or 95%, or from about 50% to about 99%, or alternatively from about 10% to about 50%, and wherein said protein is a naturally occurring human taste modulating protein.

Any amount of the compound of Formula I that provides the desired degree of enhancement can be used. For example, a compound of Formula I may be used at a concentration of about 0.1 µM to about 1,000 µM to enhance a taste modulating protein. Alternatively, concentrations of about 1, 10 or 100 µM of a compound of Formula I may be used to enhance a taste modulating protein. In certain embodiments, a single dose or two to four divided daily doses, provided on a basis of about 0.001 to 100 mg per kilogram of body weight per day, preferably about 0.01 to about 25 mg/kg of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As used herein, the term "enhancing" and grammatical variants thereof refers to interfering with the normal activity of. For example, enhancing a taste modulating protein means interfering with the normal activity of a taste modulating protein. Enhancing includes but is not necessarily limited to modulating, modifying, activating, and the like.

As used herein, the phrase "taste modulating protein" refers to a TRPM5 protein, and includes naturally and recombinantly produced TRPM5 proteins; natural, synthetic, and recombinant biologically active polypeptide fragments of said protein; biologically active polypeptide variants of said protein or fragments thereof, including hybrid fusion proteins and dimers; biologically active polypeptide analogs of said protein or fragments or variants thereof, including cysteine substituted analogs. The taste modulating protein may be a nonhuman protein, for example a nonhuman mammalian protein, or in other embodiments a nonhuman protein such as but not limited to a cow, horse, sheep, pig, chicken, turkey, quail, cat, dog, mouse, rat, rabbit, monkey, or guinea pig taste modulating protein. The taste modulating protein may be generated and/or isolated by any means known in the art. An example of the taste modulating protein and methods of producing the protein are disclosed in, for example, Liu and Liman, *Proc. Nat'l Acad. Sci. USA* 100: 15160-15165 (2003); D. Prawitt, et al., *Proc. Nat'l Acad. Sci. USA* 100:15166-71 (2003); and Ulrich, N. D., et al., *Cell Calcium* 37: 267-278 (2005); each of which is fully incorporated by reference herein.

A homologue is a protein that may include one or more amino acid substitutions, deletions, or additions, either from natural mutations of human manipulation. Thus, by way of example, a taste modulating protein may include one or more amino acid substitutions, deletions or additions, either from natural mutations or human manipulation. As indicated, changes are preferably of a minor nature, such as conservative amino acid substitutions that do not significantly affect the folding or activity of the protein.

The variant taste modulating proteins which may be enhanced in accordance with the present invention comprise non-conservative modifications (e.g., substitutions). By "nonconservative" modification herein is meant a modification in which the wild-type residue and the mutant residue differ significantly in one or more physical properties, including hydrophobicity, charge, size, and shape. For example, modifications from a polar residue to a nonpolar residue or vice-versa, modifications from positively charged residues to negatively charged residues or vice versa, and modifications from large residues to small residues or vice versa are non-conservative modifications. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. In one embodiment, the variant taste modulating proteins used in accordance with the present invention have at least one nonconservative modification.

In other embodiments, the method of the invention comprises enhancing a taste modulating protein that is a nonhuman protein, such as but not limited to a cow, horse, sheep, pig, chicken, turkey, quail, cat, dog, mouse, rat, rabbit, monkey, or guinea pig taste modulating protein.

In other instances, the method comprises administering the compound according to Formula I as a food composition, a pharmaceutical composition, or a veterinary composition, e.g., wherein the compound is in a concentration from about 1% to about 10% on a weight percentage basis, or in an amount of about 0.01 mg to about 10 mg per mL.

An additional aspect of the present invention is a method of enhancing the depolarization of a taste receptor cell, comprising contacting the taste receptor cell with a compound according to Formula I, or any of the specific subgroups, subclasses, or specific compounds described above. For example, a compound of Formula I may enhance the depolarization of a taste receptor cell by a mechanism other than, or in addition to, the mechanism of enhancing a taste receptor protein. In one embodiment of this aspect of the present invention, the method comprises contacting a taste receptor cell with a compound of Formula I, or any of the specific subgroups, subclasses, or specific compounds described above, wherein said taste receptor cell can detect a sweet taste. In another embodiment of the present invention, the method comprises administering a compound of Formula I, or any of the specific subgroups, subclasses, or specific compounds described above, to a subject in an amount sufficient to enhance the depolarization of a taste receptor cell. Furthermore, when administered orally, the compound may be dispersed or diluted by saliva.

By way of example, the present invention is directed to a method of enhancing the depolarization of a taste receptor cell, comprising contacting said taste receptor cell with a compound of Formula I, or any of the specific subclasses and specific compounds listed above, and enhancing the depolarization of the taste receptor cell by at least about 10%, 20%, 30%, 40%, 50%, 60%, 70%, 80%, 90%, or 95%, or from about 60% to about 99%, or alternatively from about 30% to about 75%. In another embodiment, the present invention is directed to a method of enhancing the depolarization of a taste receptor cell, comprising contacting said protein with a compound of Formula I, or any of the specific subclasses and specific compounds listed above, and enhancing the depolarization of the taste receptor cell by at least about 10%, 20%, 30%, 40%, 50%, 60%, 70%, 80%, 90%, or 95%, or from about 50% to about 99%, or alternatively from about 20% to about 60%, and wherein said taste receptor cell is a naturally occurring taste modulating protein. In another embodiment, the present invention is directed to a method of enhancing a taste receptor cell, comprising contacting said protein with a compound of Formula I, or any of the specific subclasses or specific compounds listed above, and enhancing the taste receptor cell by at least about 10%, 20%, 30%, 40%, 50%, 60%, 70%, 80%, 90%, or 95%, or from about 50% to about 99%, or alternatively from about 40% to about 80%, and wherein said taste receptor cell is a human taste receptor cell.

Any amount of the compound of Formula I that provides the desired degree of enhancement can be used. For example, a compound of Formula I may be used at a concentration of about 0.1 μM to about 1,000 μM to enhance a taste receptor cell. Alternatively, concentrations of about 1 μM, 50 μM, or 100 μM of a compound of Formula I may be used to enhance the depolarization of a taste receptor cell.

In certain embodiments, a single dose or two to four divided daily doses, provided on a basis of about 0.001 to 100 mg per kilogram of body weight per day, preferably about 0.01 to about 25 mg/kg of body weight per day is appropriate. When enhancing a taste receptor cell in vivo, the compound of Formula I is preferably administered orally.

The compound according to Formula I, or any of the specific subgroups, subclasses, or specific compounds described above, can be typically present in an amount ranging from about 0.00001% to about 50% by weight, preferably about 0.0001% to about 2% by weight, or alternatively, from 0.0001% to about 0.1% by weight. The present invention also contemplates an amount of about 0.0001% to about 1%, preferably about, 0.0005%, 0.001%, 0.002%, 0.005%, 0.01%, 0.05%, 0.1%, 0.3%, 0.8%, 1.5%, by weight.

In one embodiment of this aspect of the present invention, the method comprises contacting a taste receptor cell with a compound of Formula I, or any of the specific subgroups, subclasses, or specific compounds described above, wherein said taste receptor cell can detect a sweet, bitter, sour, salty, or umami taste. In another embodiment of the present invention, the method comprises administering a compound of Formula I, or any of the specific subgroups, subclasses, or specific compounds described above, to a subject in an amount sufficient to enhance the depolarization of a taste receptor cell. Furthermore, when administered orally, the compound may be dispersed or diluted by saliva.

Compositions

The present invention is also directed to various, useful compositions comprising a compound of Formula I or a physiologically acceptable salt thereof.

In another embodiment, the present invention is directed to a food product comprising a sweet tastant and one or more compounds according to Formula I, or any of the specific subgroups, subclasses, or specific compounds described above. Preferably, the food product is one which exhibits a sweet taste and/or contains a sweetening agent which can be enhanced by a compound according to Formula I, or any of the specific subgroups, subclasses, or specific compounds described above. Furthermore, in a preferred embodiment, the food product comprises a compound of Formula I, or any of the specific subgroups, subclasses, or specific compounds described above in an amount sufficient to enhance the sweet taste. Specific sweetening agents to which one of more compounds of Formula I, or any of the specific subgroups, subclasses, or specific compounds described above, can be added to enhance its sweet taste include but are not necessarily limited to sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®. Specific food products in which an enchanted sweet taste is desired include but are not limited to cakes, cookies, confectioneries such as candies, gums and chocolates, creams, icing, ice cream, pies and breads. Specific food products which are beverages include soft drinks, juices and other fruit drinks, sports drinks such as GATORADE®, coffee, teas, iced teas, coca, alcoholic beverages and KOOL-AID®.

Specific food products to which one of more compounds of Formula I, or any of the specific subgroups, subclasses, or specific compounds described above, can be added include but are not necessarily limited to, potassium chloride, ammonium chloride, sodium chloride (e.g., table salt), magnesium chloride, halide salts, naringin, caffeine, urea, magnesium sulfate, acetosulfames, aspirin, potassium benzoate, potassium bicarbonate, potassium carbonate, potassium nitrate, potassium nitrite, potassium sulfate, potassium sulfite, potassium glutamate, food preservatives in their physiologically acceptable salts, antibiotics, unsweetened chocolate, cocoa beans, yoghurt, preservatives, flavor enhancers, dietary supplements, gelling agents, pH control agents, nutrients, processing aids, bodying agents, dispersing agents, stabilizers, colorings, coloring diluents, anticaking agents, antimicrobial agents, formulation aids, leavening agents, surface active agents, anticaking agents, nutrient supplements, alkali, acids, sequestrants, denuding agents, general purpose buffers, thickeners, cooked out juice retention agents, color fixatives in meat and meat products, color fixatives in poultry and poultry products, dough conditioners, maturing agents, yeast foods, mold retardants, emulsifiers, texturizers, binders, water correctives, miscellaneous and general purpose food additives, tableting aids, lye peeling agents, washing water agents, oxidizers, antioxidants, enzymes, extenders, fungicides, cake mixes, coffee, tea, dry mixes, non-dairy creamers, salts, animal glue adjuvant, cheese, nuts, meat and meat products, poultry and poultry product, pork and pork products, fish and fish products, vegetable and vegetable products, fruit and fruit products, smoked products such as meat, cheese fish, poultry, and vegetables, whipping agents, masticatory substances in chewing gums, dough strengtheners, animal feed, poultry feed, fish feed, pork feed, defoaming agents, juices, liquors, substances or drinks containing alcohol, beverages including but not limited to alcoholic beverages and non-alcoholic carbonated and/or non-carbonated soft drinks, whipped toppings, bulking agents used in eatables including but not limited to starches, corn solids, polysaccharides and other polymeric carbohydrates, icings, as well as potassium-containing or metal-containing substances and the like. The compound according to Formula I, or any of the specific subgroups, subclasses, or specific compounds described above, can be typically present in an amount ranging from about 0.001% to about 50% by weight, preferably about 0.1% to about 10% by weight, or alternatively, from 0.1% to about 1% by weight, of the sweet tastant. The present invention also contemplates the preparation of amount of about 1% to about 20%, preferably about 1% to about 5%, about 1%, 3%, or 4%, by weight.

In other embodiments, the food product is a liquid food product, e.g., a carbonated beverage, or a solid food product, e.g., citrus fruits; vegetables; seasoning or flavoring materials; soybean products; fish products; meats and processed meats; dairy products; breads and cakes; and confectioneries. A The food product may contain the compound according to Formula I in a concentration from about 1% to about 10% on a weight percentage basis, or in an amount from about 0.01 mg to about 100 mg per mL of food product, or in an amount from about 0.01 mg to about 100 mg per gram of food product, or in an amount of about 0.1 mg/L to about 100 mg/L and the sweet tastant is administered in an amount of 10 g/L to 100 g/L. Alternatively, the food product comprises the compound according to Formula I and the sweet tastant are administered in a ratio ranging from 1:106 to 1:103, or comprises the compound according to Formula I is administered in an amount ranging from $10^{-4}$% to $10^{-1}$% of the sweet tastant by weight.

In other instances, the method is such that the sweet tastant is selected from the group consisting of sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET N LOW®, NUTRASWEET®, and mixtures thereof.

In other instances, the food product comprises, consists of, or consists essentially of a compound according to Formula I, or any of the specific subgroups, subclasses, or specific compounds described above, and one or more sweet tastants. Such sweet tastants include sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, NUTRASWEET®, and mixtures thereof.

The compound according to Formula I, or any of the specific subgroups, subclasses, or specific compounds described above, can be typically present in an amount ranging from about 0.00001% to about 50% by weight, preferably about 0.0001% to about 2% by weight, or alternatively, from 0.0001% to about 0.1% by weight. The present invention also contemplates an amount of about 0.0001% to about 1%, preferably about, 0.0005%, 0.001%, 0.002%, 0.005%, 0.01%, 0.05%, 0.1%, 0.3%, 0.8%, 1.5%, by weight, of the food product.

For example, an embodiment of the invention includes an improved cola beverage, such as COKE® or PEPSI® wherein the improvement comprises one or more s of Formula I. Cola beverages of the invention can be prepared by mixing cola concentrate with carbonated water. Typically about 50 mL of cola concentrate is added per 250 mL of carbonated water. Cola concentrate can be prepared by mixing cola flavor, caramel color, and optionally caffeine with water, one or more sweet tastants, one or more compounds of Formula I, and one or more acid components.

A cola flavor refers to either a natural or artificial flavor. Such cola flavors are commercially available. Commercial cola flavors are available, for example, from International Flavor and Fragrances, Dayton, N.J.; Artificial—#13573011 and Natural #K3559549. Commercial cola flavors are also available from Tastemaker, Cincinnati, Ohio, and Givaudan Roure, Clifton, N.J.

The acid component refers an ingredient that contributes sourness to the beverage and is added to balance the flavor profile by reducing chemical or sweetener side tastes. Acids may include malic acid, citric acid, phosphoric acid or combinations thereof.

Examples of sweet tastants include but are not limited to the group consisting of sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®. Sucrose, saccharin, sucralose, and aspartame or preferred. As discussed supra, the compositions of the invention can comprise more than one sweet tastant. For example, the food products of this invention can comprise both sucrose and corn syrup as sweet tastants, or sucrose and aspartame as sweet tastants, or saccharin and sucralose as sweet tastants.

For example, the cola concentrate can prepared by mixing phosphoric acid (75% Rhone-Poulenc), citric acid (anhydrous, ADM, Decatur, Ill.), caffeine (Mallinckrodt, Paris, Ky.), caramel Color (DS400, Sethness, Chicago, Ill.), cola Flavor (SN018976, International Flavors and Fragrances, Dayton, N.J.), sucrose, one or more compounds of Formula I, and water. The concentrate is blended until all ingredients are dissolved (30-40 minutes) using a magnetic stirring plate. Fifty milliliters of the concentrate are added to 250 mL of carbonated water to complete the preparation of the cola beverage. Fifty milliliters of cola concentrate typically contains from 0.01 to 5 mL of phosphoric acid, preferably about 0.01-1 mL, 0.1 to 100 g of sucrose, preferably about 1-10 g, about $1\times10^{-6}$ g to 10 g of a compound of Formula I, preferably about $1\times10^{-3}$ g to 1 g, about 0.001 g to 0.1 g of citric acid, preferably about 0.005-0.1 g, 0.001 to 1 g of caffeine, preferably about 0.01 to 0.1 g of caffeine, 0.01 to 5 g of caramel flavor, preferably about 0.05 to 1 g, 0.001 to about 10 mL of cola flavor, preferably about 0.01 to about 2 mL.

The compound according to Formula I, or any of the specific subgroups, subclasses, or specific compounds described above, can be typically present in an amount ranging from about 0.00001% to about 50% by weight, preferably about 0.0001% to about 2% by weight, or alternatively, from 0.0001% to about 0.1% by weight. The present invention also contemplates an amount of about 0.0001% to about 1%, preferably about, 0.0005%, 0.001%, 0.002%, 0.005%, 0.01%, 0.05%, 0.1%, 0.3%, 0.8%, 1.5%, by weight, of the cola beverage.

In each of the embodiments of the methods described herein, a compound of Formula I, or any of the specific subgroups, subclasses, or specific compounds described above, may be used in varying ratios to the tastant, i.e. the agent that is believed to cause the sweet taste. For example, a composition of the invention may comprise a compound of Formula I in a molar ratio of about $1:10^6$ to about 10:1, or alternatively administered in a molar ratio of about $1:10^5$, about $1:10^4$, about $10:10^3$, about $1:10^2$, relative to the tastant. As will be appreciated, the various ranges and amounts of the compound of Formula I can be used, with modifications if preferred, in each of the embodiments described herein. The composition may also comprise $10^{-4}$% to $10^{-1}$% of the compound of Formula I relative to the sweet tastant, by weight.

The compound according to Formula I, or any of the specific subgroups, subclasses, or specific compounds described above, can be typically present in the cola beverage in an amount ranging from about 0.001 mg to about 10 g per serving, preferably about 0.01 mg to about 5 g per serving, or alternatively, from 0.05 mg to about 1 g per serving. The present invention also contemplates cola beverages with amounts of the compound of Formula I of about 0.05 mg, 0.1 mg, 0.5 mg, 1 mg, 5 mg, 10 mg, 25 mg, 50 mg, 100 mg, 500 mg, 1 g, 2 g, 5 g and 8 g per serving.

Any amount of the compound of Formula I that provides the desired degree of sweetness enhancement can be used. For example, a compound of Formula I may be used at a concentration of about 30 μg/L to about 1.5 g/L to enhance a sweet taste. Alternatively, concentrations of about 0.1 to 100 mg/L of a compound of Formula I may be used to enhance a sweet taste. It is contemplated that between 0.1 mg/L and 100 mg/L of the compound of Formula I is present and between 10 g/L and 100 g/L of sweet tastant is present. For example, a composition could contain 0.1 mg/L, 1 mg/L, or 10/L mg of the compound of Formula I for 10 mg/L of the tastant. Alternatively, the composition could contain 0.5 mg/L, 5 mg/L or 50 mg/L of the compound of Formula I for 50 mg/L of the tastant. In other embodiments, the composition contains 1 mg/L, 10 mg/L or 100 mg/L of the compound of Formula I for 100 g/L of the tastant.

In certain embodiments, the improved food product such as the cola beverage, e.g., COKE® or PEPSI,® will contain a reduced amount of sugar compared to the prior art cola beverage. The method may be performed such that the amount of sugar required to maintain the desired sweetness of the cola beverage is reduced by at least about 10%, 20%, 30%, 40%, 50%, 60%, 70%, 80%, 90%, or 95%, or from about 60% to about 99%, or alternatively from about 20% to about 50%. Thus, in a more specific embodiment, the cola beverage comprising a sweet tastant and one or more compounds according to Formula I, contains one or more compounds according to Formula I in an amount sufficient to reduce the amount of sugar required to maintain the desired sweetness of the beverage is reduced by 10%, 20%, 30%, 40%, 50%, 60%, 70%, 80%, 90%, or 95%, or from about 60% to about 99%, or alternatively from about 30% to about 70%. Of course, in other embodiments, the amount of sugar required may be decreased to differing extents.

Additionally, the invention is directed to a process of preparing an improved food product, wherein the improvement comprises adding one or more compounds according to Formula I, or any of the specific subgroups, subclasses, or specific compounds described above, to a food product. In certain embodiments, the one or more compounds according to Formula I, or any of the specific subgroups, subclasses, or specific compounds described above, are added to the food product in an amount of about 1% to about 25%, about 1% to about 10%, or about 5%, 10%, or 15%, by weight. In other embodiments, the improved food product will contain a reduced amount of sweet tastant, e.g., sucrose.

In another embodiment, the present invention is directed to an animal food product comprising one or more compounds according to Formula I, or any of the specific subgroups, subclasses, or specific compounds described above. The one or more compounds are preferably in an amount sufficient to enhance one or more sweet tastes associated with the animal food product. Animal food products are well known in the art, see, e.g., U.S. Pat. No. 6,403,142, and include dog food, cat food, rabbit food, and the like. The animal food product may also be food products useful for feeding livestock, such as cattle, bison, pigs, chicken, and the like. In another embodiment, the animal food composition of the present invention is a solid hypoallergenic pet food comprising a component that contains protein or protein fragments wherein all of said component is partially hydrolyzed and further comprises one or more compounds according to Formula I, or any of the specific subgroups, subclasses, or specific compounds described above.

Additionally, the invention is directed to a process of preparing an improved animal food product, wherein the improvement comprises adding one or more compounds according to Formula I, or any of the specific subgroups, subclasses, or specific compounds described above, to an animal food product. In certain embodiments, the one or more compounds according to Formula I, or any of the specific subgroups, subclasses, or specific compounds described above, are added to an animal food product in an amount of about 1% to about 25%, about 1% to about 10%, or about 5%, 10%, or 15%, by weight.

In one embodiment, the pharmaceutical composition comprises one sweet tastant. In another embodiment, the pharmaceutical composition comprises more than one sweet tastant. In certain embodiments, the pharmaceutical composition comprises sucrose and corn syrup, or sucrose and aspartame, or saccharin and sucralose as sweet tastants. In another embodiment, the pharmaceutical composition contains a sweet tastant selected from sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®.

In each of the embodiments of the compositions described herein, a compound of Formula I, or any of the specific subgroups, subclasses, or specific compounds described above, may be used in varying ratios to the agent that is believed to cause the sweet taste. The compound according to Formula I, or any of the specific subgroups, subclasses, or specific compounds described above, can be typically present in an amount ranging from about 0.001% to about 50% by weight, preferably about 0.1% to about 10% by weight, or alternatively, from 0.1% to about 1% by weight. The present invention also contemplates an amount of about 1% to about 20%, preferably about 1% to about 5%, about 1%, 3%, or 4%, by weight, of the food product.

The compound according to Formula I, or any of the specific subgroups, subclasses, or specific compounds described above, can be typically present in an amount ranging from about 0.00001% to about 50% by weight, preferably about 0.0001% to about 2% by weight, or alternatively, from 0.0001% to about 0.1% by weight. The present invention also contemplates an amount of about 0.0001% to about 1%, preferably about, 0.0005%, 0.001%, 0.002%, 0.005%, 0.01%, 0.05%, 0.1%, 0.3%, 0.8%, 1.5%, by weight, of the food product.

In each of the embodiments of the methods described herein, a compound of Formula I, or any of the specific subgroups, subclasses, or specific compounds described above, may be used in varying ratios to the tastant, i.e. the agent that is believed to cause the sweet taste. For example, a composition of the invention may comprise a compound of Formula I in a molar ratio of about 0.001:1 to about 10:1, or alternatively administered in a molar ratio of about 0.01:1, about 0.02:1, about 0.05:1, about 0.1:1, or about 0.5:1, relative to the tastant. As will be appreciated, the various ranges and amounts of the compound of Formula I can be used, with modifications if preferred, in each of the embodiments described herein.

The compound according to Formula I, or any of the specific subgroups, subclasses, or specific compounds described above, can be typically present in the food product in an amount ranging from about 0.001 mg to about 10 g per serving, preferably about 0.01 mg to about 5 g per serving, or alternatively, from 0.05 mg to about 1 g per serving. The present invention also contemplates food products with amounts of the compound of Formula I of about 0.05 mg, 0.1 mg, 0.5 mg, 1 mg, 5 mg, 10 mg, 25 mg, 50 mg, 100 mg, 500 mg, 1 g, 2 g, 5 g and 8 g per serving.

The sweet taste of the food product may be enhanced by the compound of Formula I is enhanced by at least about 10%, 20%, 30%, 40%, 50%, 60%, 70%, 80%, 90%, or 95%, or from about 60% to about 99%, or alternatively from about 20% to about 50%. Thus, in a more specific embodiment, composition comprising a food product comprising a sweet tastant, one or more food ingredients, and one or more compounds according to Formula I, wherein the one or more compounds according to Formula I are present in an amount sufficient to enhance a sweet taste, produced by the food product, by at least about 10%, 20%, 30%, 40%, 50%, 60%, 70%, 80%, 90%, or 95%, or from about 60% to about 99%, or alternatively from about 30% to about 70%. Of course, in other embodiments, the sweetness may be enhanced to differing extents.

Any amount of the compound of Formula I that provides the desired degree of sweetness enhancement can be used. For example, a compound of Formula I may be used at a concentration of about 0.1 µM to about 5,000 µM to enhance a sweet taste. Alternatively, concentrations of about 1 µM, 100 µM, or 500 µM of a compound of Formula I may be used to enhance a sweet taste.

In one aspect, the present invention is directed to a pharmaceutical composition comprising a compound of Formula I, as defined above, including any of the specific embodiments, subclasses, or species described above, and one or more pharmaceutically acceptable carriers. Preferred compositions of the present invention are pharmaceutical compositions comprising a compound selected from one or more embodiments listed above, and one or more pharmaceutically acceptable excipients. Pharmaceutical compositions that comprise one or more compounds of Formula I, or any of the specific subgroups, subclasses, or specific compounds described above, may be used to formulate pharmaceutical drugs containing one or more active agents that exert a biological effect other than sweetness enhancement.

In one embodiment, the pharmaceutical composition comprises one sweet tastant. In another embodiment, the pharmaceutical composition comprises more than one sweet tastant. In certain embodiments, the pharmaceutical composition comprises sucrose and corn syrup, or sucrose and aspartame, or saccharin and sucralose as sweet tastants. In another embodiment, the pharmaceutical composition contains a sweet tastant selected from sugar, (sucrose), dextrose, maltose, dextrin, dried invert sugar, fructose, levulose, lactose, galactose, corn syrup, malodextrin, honey, sugar alcohols such as sorbitol, mannitol, xylitol, lactitol, malitol, hydrogenated starch hydrolysates, maltitol and the like, thaumatin, aspartame, acesulfame K, saccharin, sucralose, glycyrrhizin, alitame, cyclamate, stevioside, dihydrochalcones, zinc gluconate, ethyl maltol, glycine, isomalt, spray dried licorice root, glycyrrhizin, sodium gluconate, glucono-delta-lactone, ethyl vanillin, vanillin, SPLENDA®, EQUAL®, SWEET'N LOW®, and NUTRASWEET®.

The pharmaceutical composition preferably further comprises one or more active agents that exert a biological effect. Such active agents includes pharmaceutical and biological agents that have an activity other than taste enhancement. Such active agents are well known in the art. See, e.g., The Physician's Desk Reference. Such compositions can be prepared according to procedures known in the art, for example, as described in Remington's Pharmaceutical Sciences, Mack Publishing Co., Easton, Pa., USA. In one embodiment, such an active agent includes bronchodilators, anorexiants, antihistamines, nutritional supplements, laxatives, analgesics, anesthetics, antacids, $H_2$-receptor antagonists, anticholinergics, antidiarrheals, demulcents, antitussives, antinauseants, antimicrobials, antibacterials, antifungals, antivirals, expectorants, anti-inflammatory agents, antipyretics, and mixtures thereof. The pharmaceutical composition according to the present invention may comprise one or more compounds according to Formula I, as described above, or any of the specific subgroups, subclasses, or specific compounds described above; an active agent that has a bitter taste; and optionally one or more pharmaceutically acceptable carriers.

In another embodiment, the active agent is selected from the group consisting of antipyretics and analgesics, e.g., ibuprofen, acetaminophen, or aspirin; laxatives, e.g., phenolphthalein dioctyl sodium sulfosuccinate; appetite depressants, e.g., amphetamines, phenylpropanolamine, phenylpropanolamine hydrochloride, or caffeine; antacidics, e.g., calcium carbonate; antiasthmatics, e.g., theophylline; antidiuretics, e.g., diphenoxylate hydrochloride; agents active against flatulence, e.g., simethecon; migraine agents, e.g., ergotaminetartrate; psychopharmacological agents, e.g., haloperidol; spasmolytics or sedatives, e.g., phenobarbitol; antihyperkinetics, e.g., methyldopa or methylphenidate; tranquilizers, e.g., benzodiazepines, hydroxinmeprobramates or phenothiazines; antihistaminics, e.g., astemizol, chlorpheniramine maleate, pyridamine maleate, doxlamine succinate, bromopheniramine maleate, phenyltoloxamine citrate, chlorocyclizine hydrochloride, pheniramine maleate, and phenindamine tartrate; decongestants, e.g., phenylpropanolamine hydrochloride, phenylephrine hydrochloride, pseudoephedrine hydrochloride, pseudoephedrine sulfate, phenylpropanolamine bitartrate, and ephedrine; beta-receptor blockers, e.g., propanolol; agents for alcohol withdrawal, e.g., disulfuram; antitussives, e.g., benzocaine, dextromethorphan, dextromethorphan hydrobromide, noscapine, carbetapentane citrate, and chlophedianol hydrochloride; fluorine supplements, e.g., sodium fluoride; local antibiotics, e.g., tetracycline or cleocine; corticosteroid supplements, e.g., prednisone or prednisolone; agents against goiter formation, e.g., colchicine or allopurinol; antiepileptics, e.g., phenyloine sodium; agents against dehydration, e.g., electrolyte supplements; antiseptics, e.g., cetylpyridinium chloride; NSAIDs, e.g., acetaminophen, ibuprofen, naproxen, or salts thereof; gastrointestinal active agents, e.g., loperamide and famotidine; various alkaloids, e.g., codeine phosphate, codeine sulfate, or morphine; supplements for trace elements, e.g., sodium chloride, zinc chloride, calcium carbonate, magnesium oxide, and other alkali metal salts and alkali earth metal salts; vitamins; ion-exchange resins, e.g., cholestyramine; cholesterol-depressant and lipid-lowering substances; antiarrhythmics, e.g., N-acetylprocainamide; and expectorants, e.g., guaifenesin.

Active substances which have a particularly unpleasant taste include antibacterial agents such as ciprofloxacin, ofloxacin, and pefloxacin; antiepileptics such as zonisamide; macrolide antibiotics such as erythromycin; beta-lactam antibiotics such as penicillins and cephalosporins; psychotropic active substances such as chlorpromazine; active substances such as sulpyrine; and agents active against ulcers, such as cimetidine.

In another embodiment, the pharmaceutical composition comprises one or more compounds according to Formula I, or any of the specific subgroups, subclasses, or specific compounds described above, and at least one amino acid selected from the group consisting of glycine, L-alanine, L-arginine, L-aspartic acid, L-cystine, L-glutamic acid, L-glutamine, L-histidine, L-isoleucine, L-leucine, L-lysine, L-methionine, L-ornithine, L-phenylalanine, L-proline, L-serine, L-threonine, L-tryptophan, L-tyrosine, L-valine, creatine, and mixtures thereof.

In another embodiment, the pharmaceutical composition comprises one or more compounds according to Formula I, or any of the specific subgroups, subclasses, or specific compounds described above; a biologically active agent that exhibits an activity other than sweetness enhancement; and at least one amino acid, such as one selected from the group consisting of glycine, L-alanine, L-arginine, L-aspartic acid, L-cystine, L-glutamic acid, L-glutamine, L-histidine, L-isoleucine, L-leucine, L-lysine, L-methionine, L-ornithine, L-phenylalanine, L-proline, L-serine, L-threonine, L-tryptophan, L-tyrosine, L-valine, creatine, and mixtures thereof.

The pharmaceutical compositions of the present invention can be in any form suitable to achieve their intended purpose. Preferably, however, the composition is one which can be administered buccally or orally. Alternatively, the pharmaceutical composition may be an oral or nasal spray.

The pharmaceutical compositions of the invention can be in any form suitable for administration to any animal that can experience the beneficial effects of one or more compounds according to Formula I, or any of the specific subgroups, subclasses, or specific compounds described above. Foremost among such animals are humans, although the invention is not intended to be so limited. Other suitable animals include canines, felines, dogs, cats, livestock, horses, cattle, sheep, and the like. A veterinary composition, as used herein, refers to a pharmaceutical composition that suitable for non-human animals. Such veterinary compositions are known in the art.

The pharmaceutical preparations of the present invention can be manufactured using known methods, for example, by means of conventional mixing, granulating, dragée-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragée cores.

Pharmaceutical excipients are well known in the art. Suitable excipients include fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragée cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

In a further embodiment, the invention is directed to a chewable tablet comprising a sweet tastant and one or more compounds according to Formula I and one or more biologically active agents. Chewable tablets are known in the art. See, e.g., U.S. Pat. Nos. 4,684,534 and 6,060,078, each of which is incorporated by reference in its entirety. Any kind of medicament may be contained in the chewable tablet, preferably a medicament of bitter taste, natural plant extracts or other organic compounds. More preferably, vitamins such as vitamin A, vitamin B, vitamin $B_1$, vitamin $B_2$, vitamin $B_6$, vitamin C, vitamin E and vitamin K; natural plant extracts such as Sohgunjung-tang extracts, Sipchundaebo-tang extracts and *Eleutherococcus senticosus* extracts; organic compounds such as dimenhydrinate, meclazine, acetaminophen, aspirin, phenylpropanolamine, and cetylpyridinium chloride; or gastrointestinal agents such as dried aluminum hydroxide gel, domperidone, soluble azulene, L-glutamine and hydrotalcite may be contained in the core.

In another embodiment, the present invention is directed to an orally disintegrating composition wherein said orally disintegrating composition comprises a sweet tastant and one or more compounds according to Formula I, or any of the specific subgroups, subclasses, or specific compounds described above. Orally disintegrating tablets are known in the art. See, e.g., U.S. Pat. Nos. 6,368,625 and 6,316,029, each of which is hereby incorporated by reference in its entirety.

In another embodiment, the present invention is further directed to a nasal composition comprising a sweet tastant and one or more compounds according to Formula I, or any of the specific subgroups, subclasses, or specific compounds described above. Nasal sprays are known in the art. See, e.g., U.S. Pat. No. 6,187,332. Addition of one or more compounds according to Formula I to a nasal spray can reduce the experience of an unpleasant taste associated with the composition of the nasal spray. By way of a nonlimiting example, a nasal spray composition according to the present invention comprises water (such as 95-98 weight percent), a citrate (such as 0.02 M citrate anion to 0.06 M citrate anion), a compound according to Formula I, and optionally phosphate (such as 0.03 M phosphate to 0.09 M phosphate).

In another embodiment, the present invention is directed to a solid dosage form comprising a sweet tastant and a water and/or saliva activated effervescent granule, such as one having a controllable rate of effervescence, and a compound according to Formula I, or any of the specific subgroups, subclasses, or specific compounds described above. The effervescent composition may further comprise a pharmaceutically active compound. Effervescent pharmaceutical compositions are known in the art. See, e.g., U.S. Pat. No. 6,649,186, which is incorporated by reference in its entirety. The effervescent composition can be used in pharmaceutical, veterinary, horticultural, household, food, culinary, pesticidal, agricultural, cosmetic, herbicidal, industrial, cleansing, confectionery and flavoring applications. Formulations incorporating the effervescent composition comprising a compound according to Formula I can further include one or more additional adjuvants and/or active ingredients which can be chosen from those known in the art including flavors, diluents, colors, binders, filler, surfactant, disintegrant, stabilizer, compaction vehicles, and non-effervescent disintegrants.

In another embodiment, the present invention is directed to a film-shaped or wafer-shaped pharmaceutical composition that comprises a sweet tastant and a compound according to Formula I, or any of the specific subgroups, subclasses, or specific compounds described above, and is capable of disintegrating. Such a film-shaped or wafer-shaped pharmaceutical composition can be configured, for example, as quickly disintegrating administration forms, e.g., administration forms disintegrating within a period of 1 second up to 3 minutes, or as slowly disintegrating administration forms, e.g., administration forms disintegrating within a period of 3 to 15 minutes.

The indicated disintegration times can be set to the above-mentioned ranges by using, for example, matrix-forming polymers which have different disintegrating, or solubility, characteristics. Thus, by mixing the corresponding polymer components, the disintegration time can be adjusted. In addition, disintegrants are known which "draw" water into the matrix and cause the matrix to burst open from within. As a consequence, certain embodiments of the invention include such disintegrants for the purpose of adjusting the disintegration time.

Suitable are polymers for use in the film-shaped or wafer-shaped pharmaceutical composition include cellulose derivatives, polyvinyl alcohol (e.g. MOWIOL™), polyacrylates, polyvinyl pyrrolidone, cellulose ethers, such as ethyl cellulose, as well as polyvinyl alcohol, polyurethane, polymethacrylates, polymethyl methacrylates and derivatives and copolymerisates of the aforementioned polymers.

In certain embodiments, the total thickness of the film-shaped or wafer-shaped pharmaceutical composition according to the invention is preferably 5 µm up to 10 mm, preferably 30 µm to 2 mm, and with particular preference 0.1 mm to 1 mm. The pharmaceutical preparations may round, oval, elliptic, triangular, quadrangular or polygonal shape, but they may also have any rounded shape.

In another embodiment, the present invention is directed to a composition comprising a sweet tastant, a medicament or agent contained in a coating that surrounds a gum base formulation and a sweetness-enhancing amount of a compound according to Formula I, or any of the specific subgroups, subclasses, or specific compounds described above. Preferably, the coating comprises at least 50% by weight of the entire product. As the center is chewed, the medicament or agent is released into the saliva. For example, U.S. Pat. No. 6,773,716, which is incorporated herein by reference in its entirety, discloses a suitable medicament or agent contained in a coating that surrounds a gum base formulation. One or more compounds according to Formula I, or any of the specific subgroups, subclasses, or specific compounds described above, can be used in preparing the coating. Optionally, the composition may further comprise high-intensity sweeteners and appropriate flavors. It has been found that with respect to certain medicaments or agents that may have an astringent or bitter taste that by adding a sweetener enhancing agent to the formulation, that a much more palatable formulation, including the medicament, can be provided. In this regard, even though the medicament in, for example, its powder form may be bitter or have an offensive taste, the matrix used as the coating of the present invention, including the enhancing agent, will afford a product having acceptable medicinal properties. The compound according to Formula I, or any of the specific subgroups, subclasses, or specific compounds described above, can be typically present in an amount ranging from about 0.001% to about 50% by weight, preferably about 0.1% to about 10% by weight, or alternatively, from 0.1% to about 1% by weight. The present invention also contemplates an amount of about 1% to about 20%, preferably about 1% to about 5%, about 1%, 3%, or 4%, by weight, of the pharmaceutical composition.

The compound according to Formula I, or any of the specific subgroups, subclasses, or specific compounds described above, can be typically present in an amount ranging from about 0.00001% to about 50% by weight, preferably about 0.0001% to about 2% by weight, or alternatively, from 0.0001% to about 0.1% by weight. The present invention also contemplates an amount of about 0.0001% to about 1%, preferably about, 0.0005%, 0.001%, 0.002%, 0.005%, 0.01%, 0.05%, 0.1%, 0.3%, 0.8%, 1.5%, by weight, of the pharmaceutical composition.

In yet another embodiment, the present invention is directed to a process of preparing an improved composition comprising a medicament or agent contained in a coating that surrounds a gum base formulation, wherein the improvement comprises adding a compound according to Formula I, or any of the specific subgroups, subclasses, or specific compounds described above, to the coating that surrounds the gum base formulation. The compound according to Formula I may be added in varying amounts, such as about 30% 50%, 75%, 80%, or 90%, or from about 10% to about 90%. In other embodiments, the compound according to Formula I is present in about 1% to about 30%.

In a further embodiment, the invention is directed to a pharmaceutical composition suitable for aerosol administration, comprising a sweet tastant and a compound according to Formula I, or any of the specific subgroups, subclasses, or specific compounds described above, and a suitable carrier. The aerosol composition may further comprises pharmaceutically active agent. Aerosol compositions are known in the art. See, e.g., U.S. Pat. No. 5,011,678, which is hereby incorporated by reference in its entirety. As a nonlimiting example, an aerosol composition according to the present invention may comprise a medically effective amount of a pharmaceutically active substance, one or more compounds according to Formula I, or any of the specific subgroups, subclasses, or specific compounds described above, and a biocompatible propellant, such as a (hydro/fluoro)carbon propellant.

In certain embodiments, the pharmaceutical compositions of the invention comprise from about 0.001 mg to about 1000 mg of a compound of Formula I, or any of the specific subgroups, subclasses, or specific compounds described above. In another embodiment, the compositions of the invention comprise from about 0.01 mg to about 10 mg of a compound of Formula I, or any of the specific subgroups, subclasses, or specific compounds described above.

In another embodiment, the composition of the invention comprises a compound of Formula I, or any of the specific subgroups, subclasses, or specific compounds described above, in an amount sufficient to enhance the sweet taste of a modulating protein. By way of example, the present invention is pharmaceutical or veterinary composition, comprising a compound of Formula I, or any of the specific subclasses and specific compounds listed above, in an amount sufficient to enhance the taste modulating protein by at least about 10%, 20%, 30%, 40%, 50%, 60%, 70%, 80%, 90%, or 95%, or from about 50% to about 99%, or alternatively from about 10% to about 40%. In another embodiment, the present invention is directed to a method of enhancing a sweet taste modulating protein, comprising contacting said taste modulating protein with a compound of Formula I, or any of the specific subclasses and specific compounds listed above, and inhibiting the protein by at least about 10%, 20%, 30%, 40%, 50%, 60%, 70%, 80%, 90%, or 95%, or from about 50% to about 99%, or alternatively from about 20% to about 60%, and wherein said taste modulating protein is a naturally occurring taste modulating protein. In another embodiment, the present invention is directed to a method of enhancing a taste modulating protein, comprising contacting said protein with a compound of Formula I, or any of the specific subclasses and specific compounds listed above, and inhibiting the protein by at least about 10%, 20%, 30%, 40%, 50%, 60%, 70%, 80%, 90%, or 95%, or from about 50% to about 99%, or alternatively from about 20% to about 40%, and wherein said protein is a naturally occurring human taste modulating protein.

In another embodiment, the present invention is directed to a nutritional composition comprising one or more nutritional, one or more compounds according to Formula I, or any of the specific subgroups, subclasses, or specific compounds described above, and optionally one or more carriers. Examples of nutritional compositions having an undesirable taste include, but are not necessarily limited to, enteral nutrition products for treatment of nutritional deficit, trauma, surgery, Crohn's disease, renal disease, hypertension, obesity and the like, to promote athletic performance, muscle enhancement or general well being or inborn errors of metabolism such as phenylketonuria. In particular, such nutritional formulations may contain one or more amino acids which have a bitter or metallic taste or aftertaste. Such amino acids include, but are not limited to, an essential amino acids selected from the group consisting of L isomers of leucine, isoleucine, histidine, lysine, methionine, phenylalanine, threonine, tryptophan, tyrosine, and valine. Additionally, the invention is directed to a process of preparing an improved nutritional composition, wherein the improvement comprises adding one or more compounds according to Formula I, or any of the specific subgroups, subclasses, or specific compounds described above, to a nutritional composition. In certain embodiments, the one or more compounds according to Formula I, or any of the specific subgroups, subclasses, or specific compounds described above, are added to a nutritional composition in an amount of about 1% to about 50%, or about 5%, 10%, or 15%, by weight.

In another embodiment, the present invention is directed to a dental hygienic composition comprising one or more compounds according to Formula I, or any of the specific subgroups, subclasses, or specific compounds described above. Dental hygienic compositions are known in the art and include but are not necessarily limited to toothpaste, mouthwash, plaque rinse, dental floss, dental pain relievers (such as Anbesol™), and the like.

Additionally, the invention is directed to a process of preparing an improved dental hygienic composition, wherein the improvement comprises adding one or more compounds according to Formula I, or any of the specific subgroups, subclasses, or specific compounds described above, to a dental bleaching composition. In certain embodiments, the one or more compounds according to Formula I are added to a dental hygienic composition in an amount of about 0.001% to about 50% by weight, preferably about 0.1% to about 10% by weight, or preferably, from 0.1% to about 1% by weight.

The compound according to Formula I, or any of the specific subgroups, subclasses, or specific compounds described above, can be typically present in an amount ranging from about 0.00001% to about 50% by weight, preferably about 0.0001% to about 2% by weight, or alternatively, from 0.0001% to about 0.1% by weight. The present invention also contemplates an amount of about 0.0001% to about 1%, preferably about, 0.0005%, 0.001%, 0.002%, 0.005%, 0.01%, 0.05%, 0.1%, 0.3%, 0.8%, 1.5%, by weight, of the dental hygienic composition.

In another embodiment, the present invention is directed to a cosmetic product comprising one or more compounds according to Formula I, or any of the specific subgroups, subclasses, or specific compounds described above. For example, but not by way of limitation, the cosmetic product comprising a compound according to Formula I, or any of the specific subgroups, subclasses, or specific compounds described above, may be a face cream, lipstick, lip gloss, and the like. Other suitable compositions of the invention include lip balm, such as CHAPSTICK® or BURT'S BEESWAX® Lip Balm, further comprising one or more compounds according to Formula I, or any of the specific subgroups, subclasses, or specific compounds described above.

Additionally, the invention is directed to a process of preparing an improved cosmetic product, wherein the improvement comprises adding one or more compounds according to Formula I, or any of the specific subgroups, subclasses, or specific compounds described above, to a cosmetic product. In certain embodiments, the one or more compounds according to Formula I, or any of the specific subgroups, subclasses, or specific compounds described above, are added to a cosmetic product in an amount of about 1% to about 20%, preferably about 1% to about 5%, or about 1%, 2%, or 3%, by weight.

The compound according to Formula I, or any of the specific subgroups, subclasses, or specific compounds described above, can be typically present in an amount ranging from about 0.00001% to about 50% by weight, preferably about 0.0001% to about 2% by weight, or alternatively, from 0.0001% to about 0.1% by weight. The present invention also contemplates an amount of about 0.0001% to about 1%, preferably about, 0.0005%, 0.001%, 0.002%, 0.005%, 0.01%, 0.05%, 0.1%, 0.3%, 0.8%, 1.5%, by weight, of the cosmetic product.

The activity of a compound according to Formula I, or any of the specific subgroups, subclasses, or specific compounds described above can be determined by testing said compound using a number of methods known in the art. For example, one can evaluate the ability of a compound to enhance a sweet taste by using an in vivo taste assay.

The activity of a compound according to Formula I, or any of the specific subgroups, subclasses, or specific compounds described above, can also be determined by means of the assay described below.

Methods of Preparation of Compounds

A compound according to Formula I can be synthesized according to methods outlined in the following descriptions. The compounds for use in the present invention can be synthesized using procedures known in the art.

The following general schemes illustrate synthetic methods that can be used to prepare compounds of the present invention. In one process, a compound of Formula I can be prepared by condensing a suitable optionally substituted thiophene, pyrrole, imidazole or thiazole halide with a suitable hydroxypyridine or thiopyridine in a suitable organic solvent, as shown in Scheme 1 (wherein $G^1$ is N or S; X is halogen, such as a bromo group; A is S or O; n is between 0 and 4; $R^4$ is selected from $NO_2$, halogen, $C_{1-6}$ alkyl, $C_{1-6}$ hydroxyalkyl; and $G^3$, $R^1$, $R^2$, and $R^3$ are defined as above).

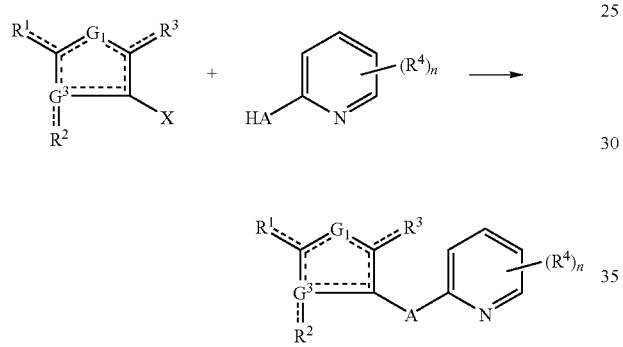

For instance, this reaction can be used to prepare the compound of Example 3 by reacting methyl 3-bromothiophene-2-carboxylate with 2-hydroxy-5-nitropyridine according to Scheme 2.

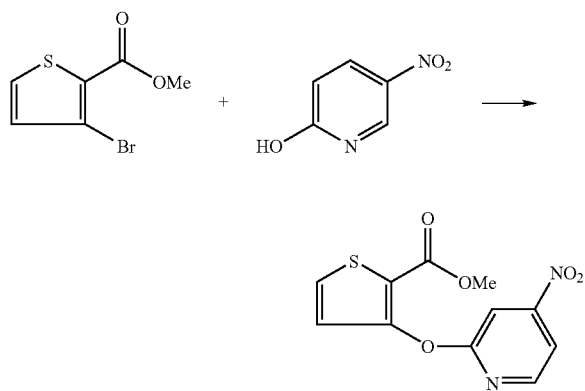

The compound of Example 8 can be prepared by reacting 1-ethyl-2-methyl,4-nitro-5-bromoimidazole and 2-thio-5-chloropyridine according to Scheme 3.

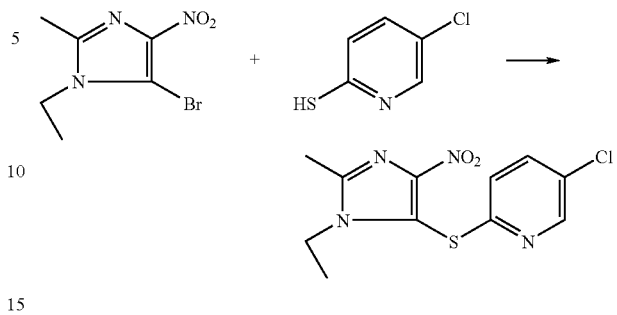

As a further example, compounds of Formula I, wherein $R^1$ and $R^2$ together with $G_3$ and the carbon atom to which $R^1$ is attached form a heterocycle, can be prepared by a direct condensation of an alpha-halo aldehyde or ketone with an amino heterocycle in a reaction medium containing a suitable solvent according to Scheme 4 (wherein $G_1$, $G_2$, $G_3$, $R^2$, $R^3$, $R^4$ are as defined above; $R^5$ is selected from H, $C_{1-6}$ alkyl, and optionally substituted phenyl; $R^6$ is selected from H and $C_{1-6}$ alkyl; and X is a halogen, preferably bromine).

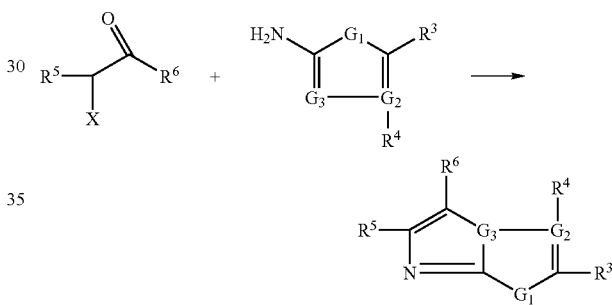

For example, the compound of Example 5 can be prepared by reacting 2-aminothiadiazole with bromo-benzaldehyde according to Scheme 5.

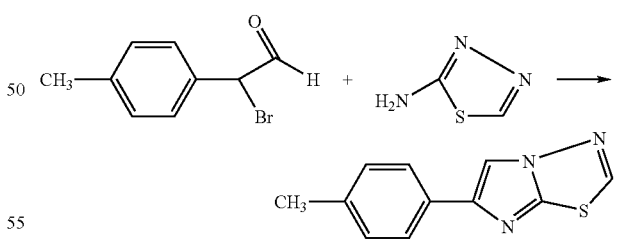

As a further example, the Compounds of Formula I wherein $R^3$ is an ether or thioether can be prepared by reacting suitable optionally substituted thiophene, pyrrole, imidazole or thiazole with an appropriate alkyl halide in a suitable organic solvent according to Scheme 6 (wherein $G_1$, $G_2$, $G_3$, $R^1$, $R^2$, $R^4$, $R^5$ and $R^6$ are as defined above; and X is a halogen, preferably bromine; $Q_1$ and $Q_2$ are independently selected from S or O; n is 0 to 4; $R^7$ is H, $C_{1-6}$ alkyl, $C_{1-6}$ alkenyl, or optionally substituted phenyl). The reaction mixture is heated and filtered to give the desired product.

Scheme 6.

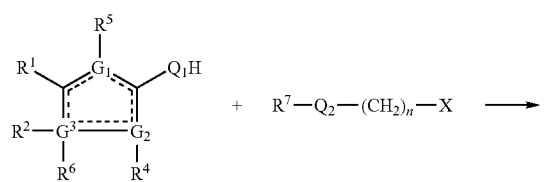

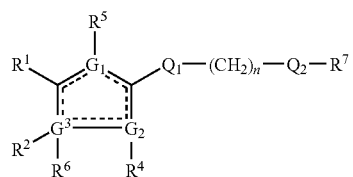

For example, the compound of Example 2 can be prepared by according to Scheme 7 in one step by a direct condensation of 2-thiol-aminobenzodithione in a 1:1 reaction medium.

Scheme 7.

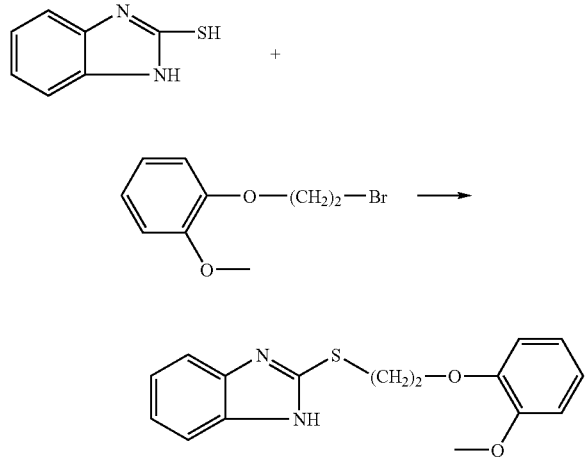

The compound of Example 7 can also be prepared by this method as Scheme 8 illustrates.

Scheme 8.

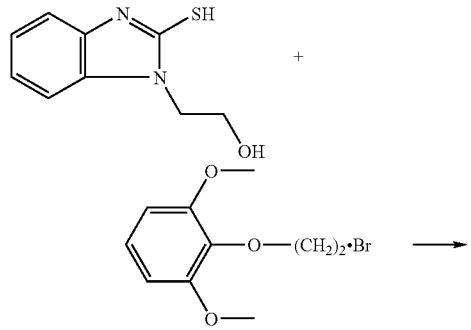

-continued

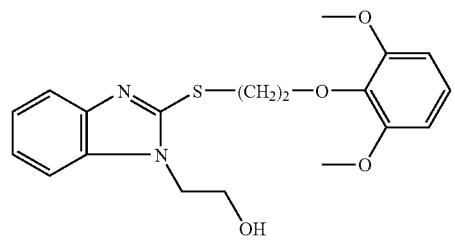

Compounds of Formula I wherein $R^3$ is =N—$CH_2$—(C=Q)-$R^7$, wherein Q is selected from S or O; and $R^7$ is H, $C_{1-6}$ alkyl or $C_{1-6}$ alkenyl, can be prepared by reacting an isothiocyanate or isocyanate with an imine in a suitable organic solvent, according to Scheme 9. The mixture is kept under reduced pressure, and the desired product is precipitated out of the reaction mixture. It is then filtered off and dried to give an off-white solid.

Scheme 9.

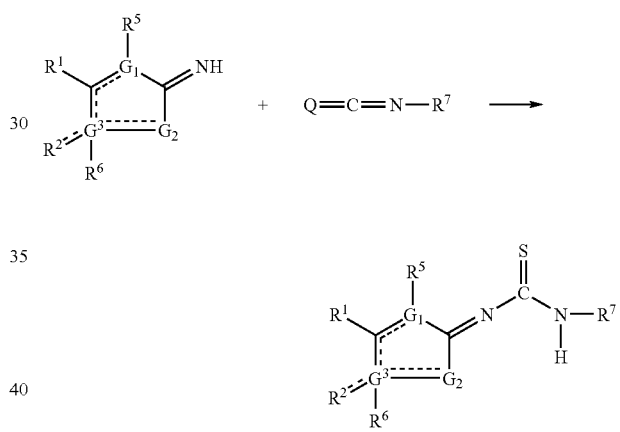

In particular, the compound of Example 10 is prepared from allyisothiocyanate and 1-imino-compound according to Scheme 10.

Scheme 10.

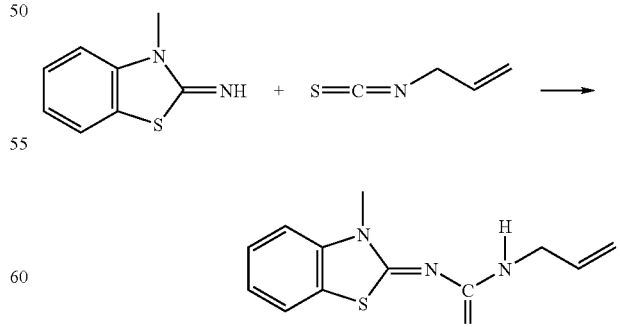

The compounds of Formula I, wherein $R^3$ is =N—$(CH_2)_n$—(C=O)—$OR^7$ (wherein n is 0 to 4; and $R^7$ is $C_{1-6}$ alkyl, or $C_{1-6}$ alkenyl) can be prepared according to Scheme 11.

Scheme 11.

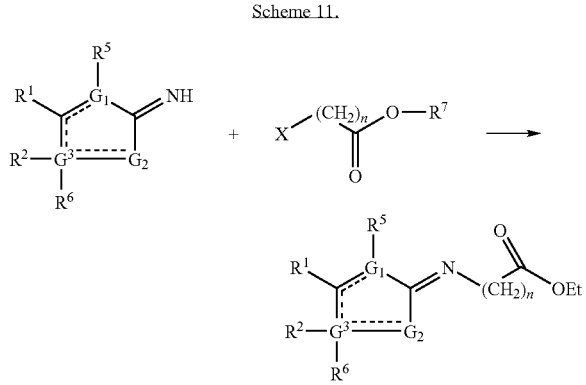

The iminio compound and haloalkyl ester are heated together in a suitable organic solvent for a brief period of time. The contents are then allowed to cool down, and the material is allowed to settle down. The cooled down material is then filtered.

This method can be used to prepare the Compound of Example 1 by reacting ethyl 2-bromoacetate with an iminio-thiomethyl compound according to Scheme 12.

Scheme 12.

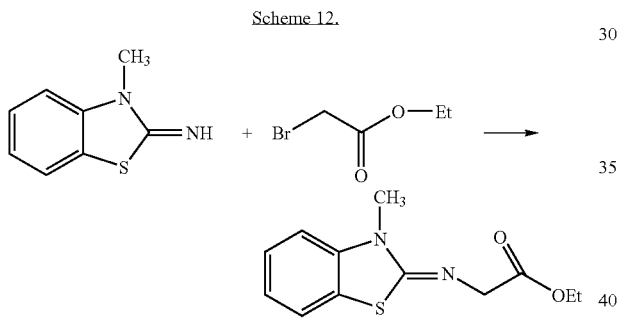

Similarly other compounds of this invention can be obtained from commercial sources and prepared by those skilled in the art. Starting materials are commercially available or they can be prepared by ordinary persons trained in the art.

The following examples are illustrative, but not limiting, of the method, compounds, and compositions of the present invention. Each of the compounds listed below was obtained from commercially available catalog companies, such as Aldrich RarechemLib, Aldrich Sigma, AsInEx, Bionet, Biotech Corp., Brandon/Berlex, Calbiochem, ChemBridge, Comgenex West, Foks H, G. & J. Research, IBS, ICN Biochemicals, Institute for Chemotherapy, IF Ltd., Kodak, Lederle Labs, Ligand-CGX, Maybridge PRI, Menai Organics, Menai/Neurocrine, MicroSource, MPA Chemists, Mybrgd/ONYX, PRI-Peakdale, RADIAN, Receptor Research, RGI, Rhone-Poulenc, SPECS/BioSPECS/SYNTHESIA, T. Glinka, Tripos Modern, VWR, Zaleska, Zelinksy/Berlex, Aeros, and Chemica. The compounds were purified using conventional purification procedures, such as HPLC. The identity of the compound was confirmed using HPLC and mass spectrometry. Other suitable modifications and adaptations of the variety of conditions and parameters normally encountered and obvious to those skilled in the art are within the spirit and scope of the invention.

EXAMPLES

Example 1

Ethyl 2-(3-Methylbenzo[d]thiazol-2(3H)-ylidene-amino)acetate

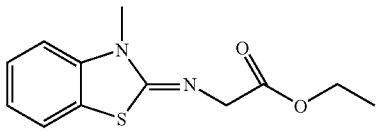

Molecular Formula: $C_{12}H_{14}N_2O_2S$; m/z: 251 (M+H, found), 250 (calculated).

Example 2

2-(2-(2-Methoxyphenoxy)ethylthio)-1H-benzimidazole

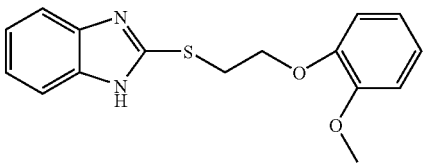

Molecular Formula: $C_{16}H_{15}N_2O_2S$; m/z: 301, (M+H, found), 300 (calculated).

Example 3

Methyl 3-(5-nitropyridin-2-yloxy)thiophene-2-carboxylate)

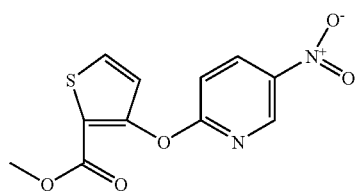

Molecular Formula: $C_{11}H_8O_5N_2S$; m/z: 281 (M+H, found), 280 (calculated).

Example 4

6-(4-Chloro-3-nitrophenyl)-3-ethyl-5H-[1,2,4]triazolo[4,3-b][1,2,4]triazole

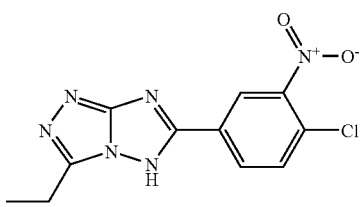

Molecular Formula: $C_{11}H_9N_6O_2Cl$; m/z: 292 (calculated).

Example 5

6-p-Tolylimidazo[2,1-b][1,3,4]thiadiazole

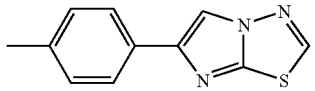

Molecular Formula: $C_{11}H_9N_3S$; m/z: 216 (M+H, found), 215 (calculated).

Example 6

N-Phenyl-4-(3-phenyl-1,2,4-thiadiazol-5-yl)-1,4-diazepane-1-carboxamide

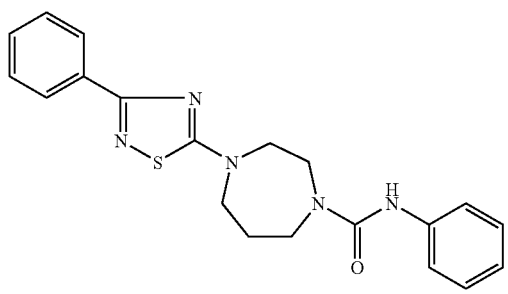

Molecular Formula: $C_{20}H_{21}ON_5S$; m/z: 379 (calculated).

Example 7

2-(2-(2-(2,6-Dimethoxyphenoxy)ethylthio)-1H-benzimidazol-1-yl)ethanol

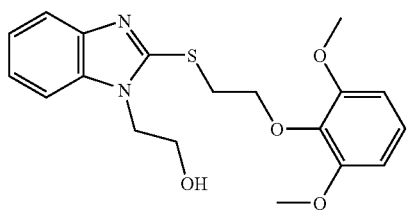

Molecular Formula: $C_{19}H_{22}O_2N_4S$; m/z: 374 (calculated).

Example 8

1-Ethyl-2-methyl-4-nitro-5-(5-chloropyridin-2-ylthio)imidazole

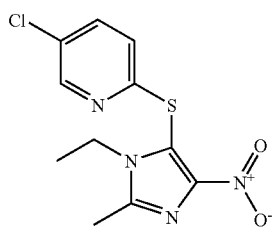

Molecular Formula: $C_{11}H_{11}O_2ClS$; m/z: 298 (calculated), 299 (M+H, found).

Example 9

2,4-Diphenyl-5,5-dimethylimidazole-1-oxide

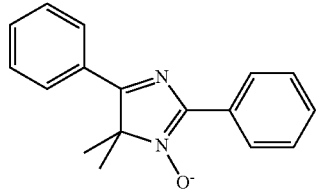

Molecular Formula: $C_{17}H_{16}N_2O$; m/z: 264 (calculated).

Example 10

1-Allyl-3-(3-methylbenzo[d]thiazol-2-(3H)-ylidene)thiourea

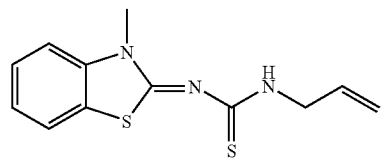

Molecular Formula: $C_{12}H_{13}N_3S_2$; m/z: 264 (M+H, found), 263 (calculated).

Example 11

2-(2-Iminothiazol-3(2H)-yl)-1-(3-nitrophenyl)ethanone

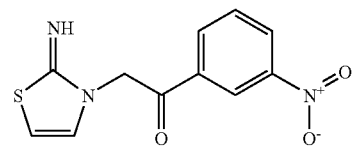

Molecular Formula: $C_{11}H_9N_3O_3$; m/z: 263 (calculated).

Example 12

4-Phenyl-2-(pyrrolidin-1-ylmethyl)phthalazin-1(2H)-one

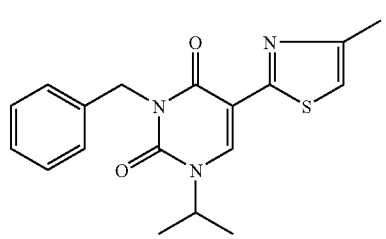

Molecular Formula: $C_{18}H_{19}N_3O_2S$; m/z: 341 (calculated).

Example 13

2-(3-Chloro-2-methoxyphenyl)imidazo[1,2-a]pyridine

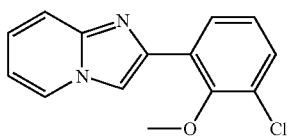

Molecular Formula: $C_{14}H_{11}N_2OCl$; m/z: 258 (calculated).

Example 14

N-(4-(4-Ethylphenyl)thiazol-2-yl)-3,5-dimethoxybenzamide

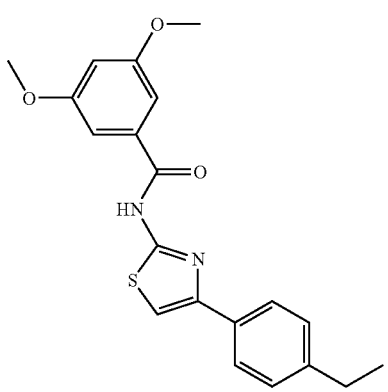

Molecular Formula: $C_{20}H_{20}N_2O_3S$; m/z: 368 (calculated).

Example 15

1-Phenylthiochromeno[4,3-d]imidazol-4(1H)-one

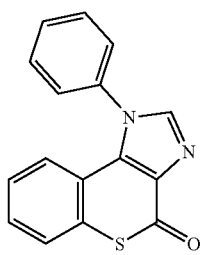

Molecular Formula: $C_{16}H_{10}N_2OS$; m/z: 278 (calculated).

Example 16

N-(4-(4-Chlorophenyl)thiazol-2-yl)-2-(dimethylamino)acetamide

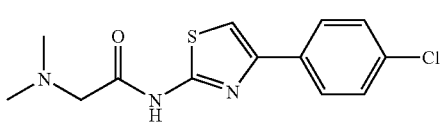

Molecular Formula: $C_{13}H_{14}N_3OSCl$; m/z: 295 (calculated).

Example 17

5-Chloro-1-methyl-3-(trifluoromethyl)-N-(4-(trifluoromethyl)phenyl)-1H-pyrazole-4-carboxamide

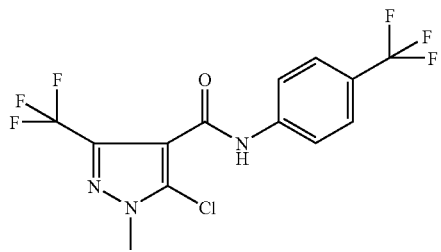

Molecular Formula: $C_{13}H_8F_6N_3OCl$; m/z: 371 (calculated).

Example 18

N-(4-(((2,6-Dimethoxypyrimidin-4-yl)amino)sulfonyl)phenyl)-4-nitrobenzamide

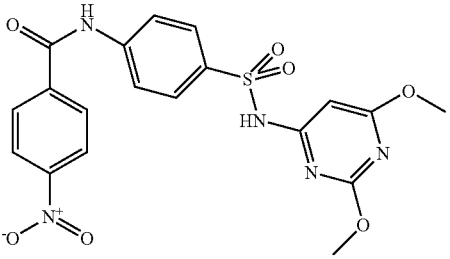

Molecular Formula: $C_{19}H_{17}N_5O_7S$; m/z: 461 (found), 459 (calculated).

Example 19

4-Phenyl-2-(pyrrolidin-1-ylmethyl)phthalazin-1(2H)-one

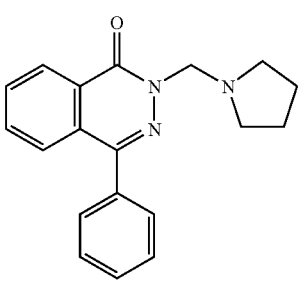

Molecular Formula: $C_{19}H_{19}N_3O$; m/z: 305 (calculated).

Example 20

5-(Perfluorophenoxy)isophthalic Acid

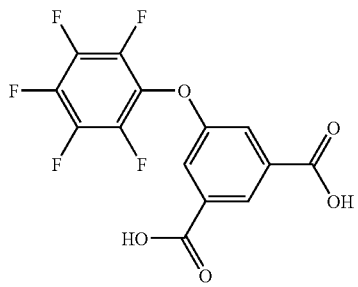

Molecular Formula: $C_{14}H_5F_5O_5$; m/z: 348 (calculated).

Example 21

2-(Dibenzylamino)acetic Acid

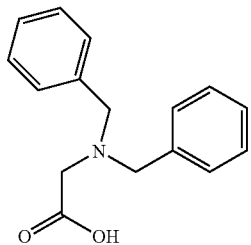

Molecular Formula: $C_{15}H_{17}O_2N$; m/z: 255 (calculated).

Example 22

Ethyl 2-cyano-2-(phenyldiazenyl)acetate

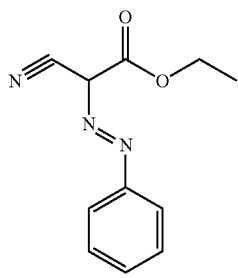

Molecular Formula: $C_{11}H_{11}N_3O_2$; m/z: 217 (calculated).

Activity of Selected Compounds

TRPM5 is an ion channel that is a part of the taste-perception machinery. This ion channel has been shown to be essential for taste transduction. Perez et al., *Nature Neuroscience* 5:1169-1176 (2002); Zhang et al., *Cell* 112:293-301 (2003). Because TRPM5 is a necessary part of the taste-perception machinery, enhancement of its activity could enhance the sensation of particular tastes.

Taste is the ability to respond to dissolved molecules and ions called tastants. Humans detect taste with taste receptor cells, which are clustered in taste buds. (Kinnamon, S. C. *TINS* 11:491-496 (1988)). Tastants bind specific receptors on the cell membrane of a taste receptor cell, leading to a voltage change across the cell membrane. A change in voltage across the cell membrane depolarizes, or changes the electric potential of the cell. This leads to a signal being sent to a sensory neuron leading back to the brain.

TRPM5 is a member of the transient receptor potential (TRP) family of ion channels. Ion channels are transmembrane proteins that form pores in a cell membrane and allow ions to pass from one side to the other (reviewed in B. Hille (Ed), 1992, *Ionic Channels of Excitable Membranes* 2nd ed., Sinauer, Sunderland, Mass.). Many channels have "gates" that open in response to a specific stimulus. As examples, voltage-gated channels respond to a change in the electric potential across the membrane, mechanically-gated channels respond to mechanical stimulation of the membrane, and ligand-gated channels respond to the binding of specific molecules. Various ligand-gated channels can open in response to extracellular factors, such as a neurotransmitters (transmitter-gated channels), or intracellular factors, such as ions (ion-gated channels), or nucleotides (nucleotide-gated channels). Still other ion channels are modulated by interactions with other proteins, such as G-proteins (G-protein coupled receptors or GPCRs).

Most ion channels mediate the permeation of one predominant ionic species. For example, sodium ($Na^+$), potassium ($K^+$), chloride ($Cl^-$), and calcium ($Ca^{2+}$) channels have been identified. While TRPM5 has been characterized as a non-selective monovalent cation channel, Prawitt et al., *Proc. Nat. Acad. Sci. USA* 100:15166-71 (2003), physiologically it is thought to primarily conduct sodium, the most abundant cation in extracellular fluids.

TRPM5 is believed to be activated by stimulation of a receptor pathway coupled to phospholipase C and by IP3-mediated $Ca^{2+}$ release. The opening of this channel is dependent on a rise in $Ca^{2+}$ levels. Hofmann et al., *Current Biol.* 13:1153-1158 (2003). The activation of this channel leads to depolarization of the TRC, which in turn leads to transmitter release and excitation of primary gustatory nerve fibers. Huang, et al., *Proc. Nat. Acad. Sci. USA* 104: 6436-6441 (2007).

Figure 1:
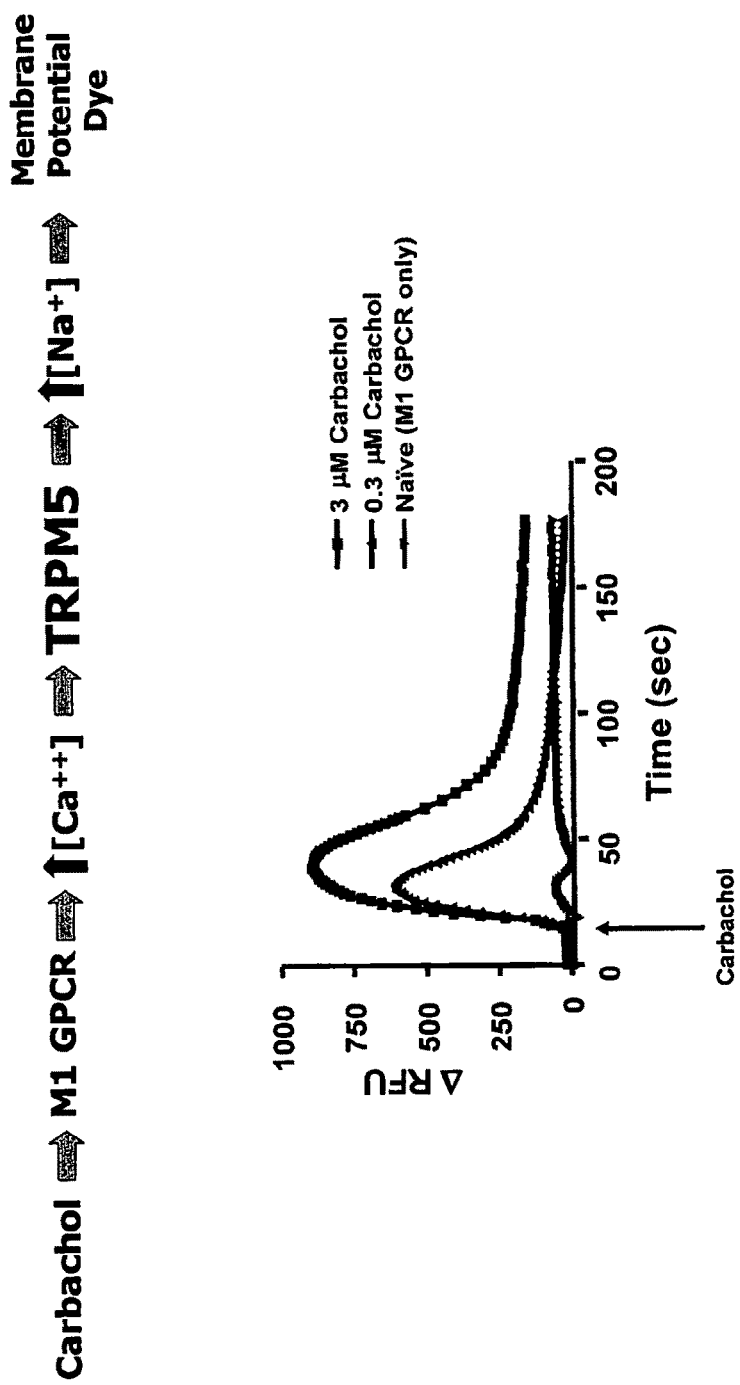
FIG. 1 illustrates the generation of the TRPM5 membrane potential dye fluorescent response in transfected HEK 293 cells. It utilizes a fluorescence Intensity Plate Reader (FLIPR) and carbachol to cause a Ca++ response and trigger TRPM5.
Figure 2:
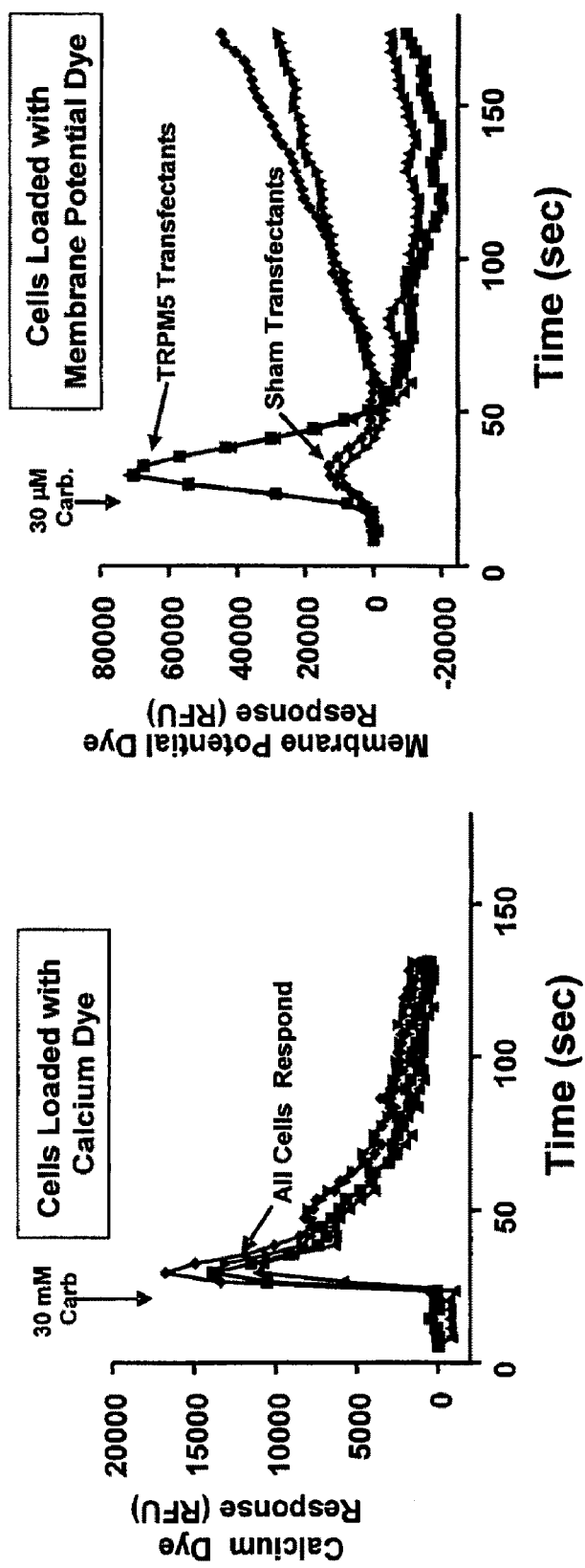
FIG. 2 illustrates a cell-based assay utilizing cloned mTRPM5 for detecting active compounds.

The activity of human TRPM5 ion channel was measured in live cells on a fluorescent imaging plate reader (FLIPR). The basis of the assay (shown in FIG. 1) is the calcium-dependent activation of the ion channel which occurs via by activation of a G-protein coupled receptor (GPCR). GPCR activation by an appropriate agonist causes a transient increase in intercellular $Ca^{2+}$ ion concentration which in turn causes the ion channel to open, letting in $Na^+$ ions. This influx causes a change in the membrane potential of the cell which can be monitored as a change in the fluorescent signal from voltage-dependent (membrane potential) fluorescent dyes. A demonstration of the assay is shown in FIG. 2, where traces of fluorescent response (Ex 530 nm/Em565 nm) versus time are shown for cells containing the plasmid and sham plasmid controls. While all cells gave a $Ca^{2+}$ response to the endogenous muscarinic GPCR agonist carbachol (left panel), only cells containing the plasmid showed a sharp peak for the membrane potential dye response (right panel).

For the screening assay, the human TRPM5 gene was cloned, put into HEK293 cells, and a stable, high expression clone was used for screening. Cells were grown in standard media at 37° C. The day before screening, the cells were removed from flasks and added to 384 well clear bottom plates (8K cells in 20 μL/well). On the assay day, 20 μL of membrane potential dye (Part No. R8123, Molecular Devices Corp.) was added to the cells and dye was allowed to be taken up, i.e., load, into the cells for 1 hr at 37° C. The dye-loaded cell plate was placed in the FLIPR along with a second 384 well plate containing test compounds as well as positive (fully inhibited) and negative (non-inhibited) controls. The assay was started by addition of 10 μL of solution from the compound plate into the cell plate. During this process, continuous fluorescent recordings were made simultaneously for all wells. After addition of the compound solution, the tips were automatically washed and a stimulation solution of 3 μM ATP to activate TRPM5 (an agonist for an endogenous purinurgic GPCR), was added to all wells of the cell plate. The height of the response was calculated and percent inhibition or enhancement values, versus negative control wells, was calculated for the test samples. Exemplary results are shown in the upper left graph of FIG. 3.

Two counterscreen assays were run on separate cell plates utilizing the same cells as described above. In the calcium counterscreen, the cells were loaded with a calcium sensitive dye (Calcium3 Dye, Part no. 8090, Molecular Devices Corp.) and stimulated by ATP to check for compounds that block the GPCR-mediated calcium activation step. Exemplary results of this assay are shown in the lower left graph of FIG. 3. In the KCl counterscreen, cells are stimulated with 10 mM KCl instead of ATP to check for compounds that inhibit the membrane potential response by virtue of being non-specific ion channel blockers or enhancers. Exemplary results are shown in FIGS. 3-5. The selective enhancement TRPM5 activity by the compounds of Examples 1-3, 5, 10 and 18 at low concentration of ATP, the G-protein coupled receptor ligand is illustrated in FIG. 4. The left graph of FIG. 4 shows the enhancement effect of the addition of a compound of the invention at 30 micromolar on the ATP concentration-effect function for membrane potential in hTRPM5-HEK293 cells, as measured by the fluorescent assay described herein. The right graph shows the lack of effect of the addition of a compound of the invention at 30 micromolar on ATP concentration-effect function for intracellular calcium in hTRPM5-HEK293 cells, as measured in the fluorescent assays described herein.

FIG. 5 illustrates the selective enhancement of TRPM5 activity by the compounds of Examples 1-3, 5, 10, and 18. In particular, enhancement is most pronounced at low ATP concentrations.

Unless otherwise indicated, the data in the table below were determined using the three assays described above, providing percent inhibition data at 10 μM. Stimulation or enhancement is seen as negative inhibition.

| Example No. | TRPM5 Activity | Calcium Counterscreen | KCl Counterscreen |
|---|---|---|---|
| 1 | −139 | −18 | 10 |
| 2 | −136 | 19 | −3 |
| 3 | −113 | 11 | 17 |
| 4 | −101 | 13 | −32 |
| 5 | −100 | 23 | 7 |
| 6 | −98 | −69 | 16 |
| 7 | −95 | −15 | −4 |
| 8 | −76 | −22 | 7 |
| 9 | −73 | −15 | 17 |
| 10 | −73 | 0 | 1 |
| 11 | −68 | −12 | 21 |
| 12 | −62 | −5 | 3 |
| 13 | −57 | 9 | −10 |
| 14 | −55 | 10 | −101 |
| 15 | −48 | −22 | −9 |
| 16 | −23 | −25 | −9 |
| 17 | −16 | 4 | −25 |

Example 23

Electrophysiological Results

Standard whole-cell recordings were obtained from HEK 393 cells stably transfected with human TRPM5. Internal solution contained 135 mM CsGlutamate, 10 mM HEPES, 2 mM MgATP, 5 mM CaCl$_2$ and 10 mM EGTA. External solution was HBSS (Gibco) buffered with 20 mM HEPES to pH 7.2. Currents were recorded with Multiclamp 700B amplifier using PClamp software; filtered at 1 kHz, sampled at 5 kHz. Holding potential was −80 mV. TRPM5 current in a single was activated by intracellular calcium dialysis (free calcium) and sampled with 200 ms ramps from −80 to 80 mV at 1 Hz. Current amplitudes were measured at −80 and 80 mV and plotted versus time. FIG. 6 shows stimulation of TRPM5 current when TRPM5 transfected cells are treated with 10 μM of the compound of Example 10 applied in a flow-through chamber such that exposure of the cell to the compound can be quickly turned on and off. The left graph of FIG. 6 shows no current activation by compound application in the absence of calcium. The central graph of FIG. 6 shows a large >5 nA current (+80 mV) in response to compound at an otherwise suboptimal calcium concentration of 300 nm. The far right graph shows a current activated by compound exposures at 30 μm calcium. While there is further stimulation of the TRPM5 current by compound at 30 uM, it is not as dramatic as at 300 nn Ca++. In essence, it appears that the compound makes the TRPM5 responsive lower or weaker Ca++ signals than is normally the case. Note that no significant current was seen in non-transfected, sham HEK cells (not shown).

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A method of enhancing a sweet taste, comprising administering to a subject a sweet tastant and a compound of Formula I:

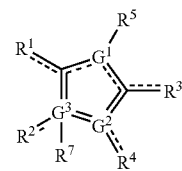

or a physiologically acceptable salt thereof, wherein $G^1$, $G^2$, and $G^3$ are independently selected from N, S, and C;

$R^1$ and $R^2$ are independently absent or selected from the group consisting of $C_{1-6}$ alkoxycarbonyl, hydrogen, $C_{1-6}$ alkyl, halogen, nitro, optionally substituted $C_{6-14}$ aryl, optionally substituted 5-14 membered heteroaryl, Ar-Q, optionally substituted $(CH_2)_nC(=O)—O—R^{2a}$, and optionally substituted $(CH_2)_nC(=O)$aryl, or $R^1$ and $R^2$, together with the $G^3$ and the carbon atom to which $R^1$ is attached, form a $C_{6-14}$ aryl or 5- to 14-membered heterocycle, each of which is optionally substituted with 1-3 substitutents independently selected from the group consisting of amino, hydroxy, nitro, halogen, cyano, thiol, oxo, $C_{1-6}$ alkyl, $C_{2-6}$ alkenyl, $C_{1-6}$ haloalkyl, $C_{1-6}$ alkoxy, $C_{1-6}$ alkenyloxy, optionally substituted $C_{6-14}$ aryl; or if the bond to $R^1$ and/or $R^2$ is a double bond, then $R^1$ and $R^2$ are independently selected from =NH and =O;

$R^3$ is selected from the group consisting of H, $C_{1-6}$ haloalkyl, $C_{1-6}$ alkyl, oxo, =NH, optionally substituted $C_{6-14}$ aryl, optionally substituted 5-14 membered heterocycle, and $L^1$-$R^{31}$;

$R^4$ is absent or is selected from the group consisting of H, $C_{1-6}$ alkyl, $C_{1-6}$ alkenyl, $C_{1-6}$ alkoxy, $C_{1-6}$ hydroxyalkyl, optionally substituted $C_{6-14}$ aryl, and optionally substituted $(CH_2)_nC(=O)$aryl, or when the bond to $R^4$ is a double bond, $R^4$ is =O;

$R^5$ is either absent or is selected from the group consisting of hydrogen, $C_{1-6}$ alkyl, and optionally substituted phenyl amide;

$R^7$ is either absent or selected from the group consisting of H and $C_{1-6}$ alkyl;

$R^{2a}$ is $C_{1-6}$ alkyl;

$R^{31}$ is H, $C_{1-6}$ alkyl, $C_{1-6}$ alkenyl, optionally substituted phenyl, amino, $C_{1-6}$ alkylamino, or $C_{1-6}$ dialkylamino;

$L^1$ is a linker selected from the group consisting of =$Z^1$-$(CH_2)_n$-$Z^2$-, -(Het)-C(O)—NH—, =N—$(CH_2)_n$—C$(=Z^3)$-$Z^4$-, —NH—C(=O)—$(CH_2)_n$-

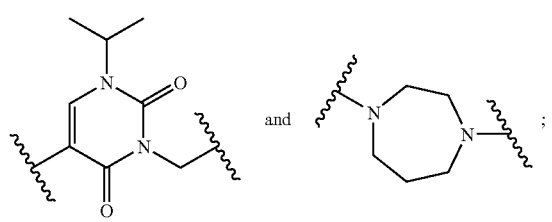

and $Z^1$ is selected from the group consisting of =N, —NH, O, and S;

$Z^2$ is absent, O, S, C(=O), C(=S), —C(=O)—O, C(=S)—O, —C(=O)—NH— or —C(=S)—NH;

$Z^3$ is O or S;

$Z^4$ is O, S, or NH;

Het is a 5- to 7-membered nitrogen-containing heterocycle;

Q is $CH_2$, O, NH, or S;

Ar is optionally substituted aryl or optionally substituted heteroaryl; and n is 0 to 10.

2. The method according to claim 1, wherein the compound of Formula I is

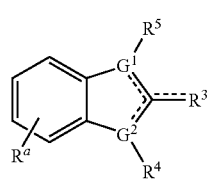

or a physiologically acceptable salt thereof,
wherein $R^3$ is $L^1$-$R^{31}$;
$R^4$ is absent, H, $C_{1-6}$ alkyl, or $C_{1-6}$ hydroxyalkyl;
$R^5$ is absent, H, or $C_{1-6}$ alkyl;
$R^a$ is H or $C_{1-6}$ alkyl; and
$G^1$ and $G^2$ are independently C, N, or S.

3. The method according to claim 2, wherein the compound is

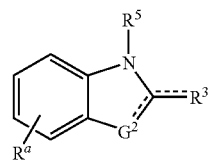

or a physiologically acceptable salt thereof,
wherein $R^3$ is $L^1$-$R^{31}$;
$R^5$ is H or $C_{1-6}$ alkyl;
G is N or S; and
$R^a$ is H or $C_{1-6}$ alkyl.

4. The method according to claim 2, wherein the compound of Formula I is

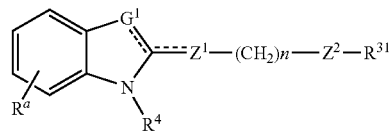

or a physiologically acceptable salt thereof,
wherein $G^1$ is S or N;
$R^4$ is H, $C_{1-6}$ alkyl, or $C_{1-6}$ hydroxyalkyl;
$R^{31}$ is H, $C_{1-6}$ alkyl, $C_{1-6}$ alkenyl, or optionally substituted phenyl;
$R^a$ is H or $C_{1-6}$ alkyl;
$Z^1$ is S or N;
$Z^2$ is —C(=O)—O, —C(=S)—O—, —O—, —S—, —C(=O)—NH—, or —C(=S)—NH—; and
n is 0 to 4.

5. The method according to claim 4, wherein the compound of Formula I is

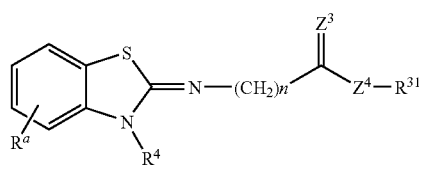

or a physiologically acceptable salt thereof,
wherein $R^4$ is H, $C_{1-6}$ alkyl, or $C_{1-6}$ hydroxyalkyl;
$R^a$ is H or $C_{1-6}$ alkyl;
$R^{31}$ is selected from the group consisting of H, $C_{1-6}$ alkyl, and $C_{1-6}$ alkenyl;
$Z^3$ is O or S;
$Z^4$ is O, S, or NH; and
n is 0 to 3.

6. The method according to claim 4, wherein the compound is

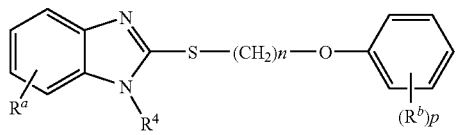

or a physiologically acceptable salt thereof, wherein $R^4$ is selected from the group consisting of H, $C_{1-6}$ alkyl, and $C_{1-6}$ hydroxyalkyl;
$R^a$ is H or $C_{1-6}$ alkyl;
$R^b$ is $C_{1-6}$ alkyl, $C_{1-6}$ alkyloxy, or hydroxy;
n is 0 to 3; and
p is 0 to 5.

7. The method according to claim 1, wherein the compound of Formula I is

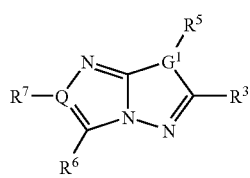

or a physiologically acceptable salt thereof,
wherein $G^1$ is N or S;
Q is N or C;
$R^3$ is H or optionally substituted phenyl;
$R^5$ is H when $G^1$ is N, or otherwise is absent;
$R^6$ is selected from the group consisting of H and $C_{1-6}$ alkyl; and
$R^7$ is selected from the group consisting of H, $C_{1-6}$ alkyl, and optionally substituted phenyl, or, when Q is N, $R^7$ is absent.

8. The method according to claim 7, wherein the compound is

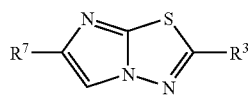

or a physiologically acceptable salt thereof,
wherein $R^3$ is H, $C_{1-6}$ alkyl, or optionally substituted phenyl; and
$R^7$ is selected from the group consisting of H, $C_{1-6}$ alkyl, and optionally substituted phenyl.

9. The method according to claim 1, wherein the compound according to Formula I is

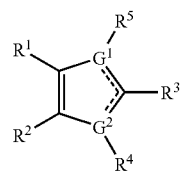

or a physiologically acceptable salt thereof,
wherein $R^1$ and $R^2$ are independently selected from the group consisting of H, $C_{1-6}$ alkyl, $C_{1-6}$ alkoxycarbonyl, and Ar-Q, wherein Q is O, NH, S, or $CH_2$, and Ar is an optionally substituted aryl or optionally substituted heteroaryl;
$R^3$ is H or $C_{1-6}$ alkyl;
$R^4$ is absent, H, or $C_{1-6}$ alkyl;
$R^5$ is absent, H, or $C_{1-6}$ alkyl;
$G^1$ is C or N; and
$G^2$ is N or S.

10. The method according to claim 9, wherein the compound is

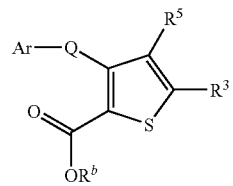

or a physiologically acceptable salt thereof,
wherein $R^3$ is H or $C_{1-6}$ alkyl;
$R^5$ is H or $C_{1-6}$ alkyl;
Ar is a 5- to 10-membered aryl or heteroaryl group optionally substituted with one or more groups independently selected from the group consisting of $NO_2$, halogen, $C_{1-6}$ alkyl, and $C_{1-6}$ hydroxyalkyl;
Q is O or NH;
$R^b$ is H or $C_{1-6}$ alkyl; and
n is 0 to 3.

11. The method according to claim 10, wherein the compound is

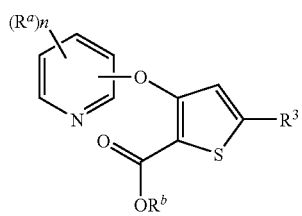

or a physiologically acceptable salt thereof,
wherein $R^3$ is H or $C_{1-6}$ alkyl;
each occurrence of $R^a$ is independently selected from the group consisting of $NO_2$, halogen, $C_{1-6}$ alkyl, or $C_{1-6}$ hydroxyalkyl;
$R^b$ is H or $C_{1-6}$ alkyl; and
n is 0 to 3.

12. The method according to claim 9, wherein the compound is:

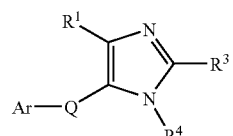

or a physiologically acceptable salt thereof,
wherein $R^1$ is H, $C_{1-6}$ alkyl, halogen, or $NO_2$;
$R^3$ and $R^4$ are independently H or $C_{1-6}$ alkyl;
Q is S, N, or O; and
Ar is a 5- to 6-membered heteroaryl optionally substituted with one or more substituents independently selected from the group consisting of nitro and halogen.

13. The method according to claim 1, wherein the compound of Formula I is:

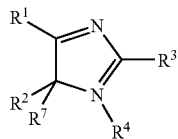

or a physiologically acceptable salt thereof,
wherein $R^1$ and $R^3$ are independently optionally substituted phenyl;
$R^4$ is absent or $C_{1-6}$ alkyl; and
$R^2$ and $R^7$ are independently $C_{1-6}$ alkyl.

14. The method according to claim 1, wherein the compound is:

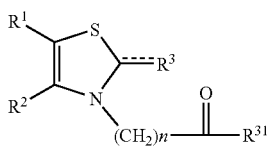

or a physiologically acceptable salt thereof,
wherein $R^1$ is H or $C_{1-6}$ alkyl;
$R^2$ is H;
$R^3$ is $C_{1-6}$ alkyl, H, oxo, or =NH;
$R^{31}$ is optionally substituted phenyl; and
n is 0 to 3.

15. The method according to claim 1, wherein the compound is:

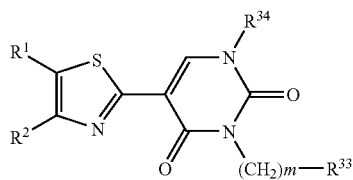

or a physiologically acceptable salt thereof,
wherein $R^1$ is H or $C_{1-6}$ alkyl;
$R^2$ is H or $C_{1-6}$ alkyl;
$R^{33}$ is optionally substituted phenyl;
$R^{34}$ is H or $C_{1-6}$ alkyl; and
m is 1.

16. The method according to claim 1, wherein the compound is selected from the group consisting of
ethyl 2-(3-methylbenzo[d]thiazol-2(3H)-ylideneamino) acetate;
2-(2-(2-methoxyphenoxy)ethylthio)-1H-benzo[d]imidazole;
methyl 3-(5-nitropyridin-2-yloxy)thiophene-2-carboxylate;
6-(4-chloro-3-nitrophenyl)-3-ethyl-5H-[1,2,4]triazolo[4,3-b][1,2,4]triazole;
6-p-tolylimidazo[2,1-b][1,3,4]thiadiazole;
N-phenyl-4-(3-phenyl-1,2,4-thiadiazol-5-yl)-1,4-diazepane-1-carboxamide;
2(2-(2-(2,6-dimethoxyphenoxy)ethylthio)-1H-benzimidazol-1-yl)ethanol;
1-ethyl-2-methyl-4-nitro-5-(5-chloropyridin-2-ylthio) imidazole;
2,4-diphenyl-5,5-dimethylimidazole-1-oxide;
1-allyl-3-(3-methylbenzo[d]thiazol-2-(3H)-ylidene)thiourea;
2-(2-iminothiazol-3(2H)-yl)-1-(3-nitrophenyl)ethanone;
3-benzyl-1-isopropyl-5-(4-methylthiazol-2-yl)pyrimidine-2,4(1H,3H)-dione;
2-(3-chloro-2-methoxyphenyl)imidazo[1,2-a]pyridine;
N-(4-(4-ethylphenyl)thiazol-2-yl)-3,5-dimethoxybenzamide;
1-phenylthiochromeno[4,3-d]imidazol-4(1H)-one;
N-(4-(4-chlorophenyl)thiazol-2-yl)-2-(dimethylamino) acetamide;
5-chloro-1-methyl-3-(trifluoromethyl)-N-(4-trifluoromethyl)phenyl-1H-pyrazole-4-carboxamide; and
physiologically acceptable salts thereof.

17. The method according to claim 1, wherein the sweet tastant is selected from the group consisting of sucrose, fructose, and mixtures thereof; and wherein the sweet tastant and the compound of Formula I are administered in a food product.

18. The method according to claim 17, wherein the food product is a beverage.

19. The method according to claim 18, wherein the compound according to Formula I and the sweet tastant are in a ratio from about $1:10^6$ to about $1:10^3$.

20. The method according to claim 1, wherein Ar-Q is an optionally substituted 5-14 membered heteroaryloxy or optionally substituted 5-14 membered heteroarylthio.

* * * * *